United States Patent [19]

Mooradian

[11] 4,062,864

[45] Dec. 13, 1977

[54] 3-HYDROXY CARBAZOLE DERIVATIVES

[75] Inventor: Aram Mooradian, Schodack, N.Y.

[73] Assignee: Sterling Drug Inc., New York, N.Y.

[21] Appl. No.: 579,157

[22] Filed: May 20, 1975

Related U.S. Application Data

[63] Continuation-in-part of Ser. No. 425,205, Dec. 17, 1973, Pat. No. 3,959,309, which is a continuation-in-part of Ser. No. 465,238, April 29, 1974, abandoned, which is a continuation-in-part of Ser. No. 172,206, Aug. 16, 1971, abandoned, which is a continuation-in-part of Ser. No. 793,545, Jan. 23, 1969, abandoned, which is a continuation-in-part of Ser. No. 659,606, Aug. 10, 1967, Pat. No. 3,642,816.

[30] Foreign Application Priority Data

Jan. 24, 1968 Canada .................................. 10686

[51] Int. Cl.$^2$ .......................................... C07D 209/88
[52] U.S. Cl. .................................................... 260/315
[58] Field of Search ........................................ 260/315

[56] References Cited

U.S. PATENT DOCUMENTS 3,592,824   7/1971   Schut ................................... 260/315
3,642,816   2/1972   Mooradian ........................... 260/315

OTHER PUBLICATIONS

Teuber et al., "Chem Abstracts" vol. 66 (1967), No. 37796c.

Primary Examiner—Henry R. Jiles
Assistant Examiner—R. W. Ramsuer
Attorney, Agent, or Firm—Frederik W. Stonner; B. Woodrow Wyatt

[57] ABSTRACT 3-(Substituted-amino)-1,2,3,4-tetrahydrocarbazoles are prepared by reacting appropriate 4-substituted-aminocyclohexanones with a phenylhydrazine, by reacting a 3-(sulfonyloxy)-1,2,3,4-tetrahydrocarbazole with an appropriate substituted amine, or by reduction of an appropriate 3-(acylamino)-1,2,3,4-tetrahydrocarbazole. The 3-(substituted-amino)-1,2,3,4-tetrahydrocarbazoles of this invention have analgetic and psychotropic activities. Moreover, certain of these compounds also have antihistaminic activity.

8 Claims, No Drawings

3-HYDROXY CARBAZOLE DERIVATIVES

This application is a continuation-in-part of copending application Ser. No. 425,205, filed Dec. 17, 1973, now U.S. Pat. No. 3,959,309, issued May 25, 1976 (of which application Ser. No. 465,238, filed Apr. 29, 1974, now abandoned, is also a continuation-in-part), in turn a continuation-in-part of copending application Ser. No. 172,206, filed Aug. 16, 1971, now abandoned, in turn a continuation-in-part of copending application Ser. No. 739,545, filed Jan. 23, 1969, now abandoned, in turn a continuation-in-part of copending application Ser. No. 659,606, filed Aug. 10, 1967, now U.S. Pat. No. 3,642,816, issued Feb. 15, 1972.

This invention relates to a class of chemical compounds known in the art of chemistry as 1,2,3,4-tetrahydrocarbazoles, to the preparation thereof, and to intermediates therefor.

In one aspect of this invention there are provided novel 3-(N=B)-9-R-1,2,3,4-tetrahydrocarbazoles having the structural formula

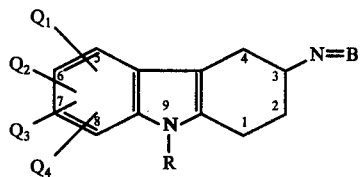

I where N=B is NHR', NR'R" or NR'''-Y-NR'R", where R' and R" are lower-alkyl or Ar-lower-alkyl, or R' and R" taken together with the nitrogen form a heterocyclic ring selected from 4-morpholinyl, 4-thiomorpholinyl, 1-piperidinyl, 1-pyrrolidinyl, 1-piperazinyl, 4-lower-alkyl-1-piperazinyl and 4-AR-1-piperazinyl, R''' is hydrogen or lower-alkyl and Y is lower-alkylene; R is hydrogen, lower-alkyl, Ar-lower-alkyl, lower-alkenyl, hydroxy-lower-alkyl, lower alkanoyloxy-lower-alkyl, Ar-carbonyloxy-lower-alkyl, carboxy-lower-alkyl, lower-alkoxy-carbonyl-lower-alkyl or Ar-lower-alkoxycarbonyl-lower-alkyl, or R is Y-NR'R", where Y, R' and R" have the same meaning given above; $Q_1$ is selected from the substituents of the groups designated (1), (3) and (4) below; $Q_2$ is selected from the substituents of the groups designated (2), (3) and (4) below; $Q_3$ is selected from the substituents of the groups designated (3) and (4) below; $Q_4$ is selected from the substituents of the groups designated (2) and (4) below, where the substituents of the groups designated (1), (2), (3) and (4) are respectively: (1) Ar-lower-alkyl, Ar—O, Ar, cyano, formyl, —CH$_2$OH,

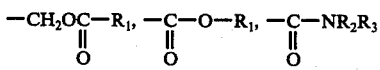

and —CH$_2$NR$_2$R$_3$, where R$_1$ is hydrogen, lower-alkyl, Ar or —CH$_2$Ar, and R$_2$ and R$_3$ are hydrogen or lower-alkyl, or R$_2$ and R$_3$ taken together with the nitrogen form a heterocyclic ring selected from 4-morpholinyl, 4-thiomorpholinyl, 1-piperidinyl, 1-pyrrolidinyl, 1-piperazinyl, 4-AR-1-piperazinyl and 4-lower-alkyl-1-piperazinyl, (2) tertiary-lower-alkyl, Ar-lower-alkoxy, hydroxy, trihalomethyl, nitro, amino, lower-alkylamino, di(lower-alkyl)amino and lower-alkanoylamino, (3) lower-alkylthio, lower alkyl-sulfinyl and lower-alkyl-sulfonyl, and (4) hydrogen, non-tertiary-lower-alkyl, lower-alkoxy and halo, provided that when $Q_2$ and $Q_4$ are selected from the substituents of the group designated (2) they are non-adjacent and when $Q_1$ and $Q_2$ or $Q_1$, $Q_2$ and $Q_3$ are substituents selected from the group designated (3) they are identical; and Ar is phenyl or phenyl substituted by from one to three of the same or different substituents selected from non-tertiary-lower-alkyl, non-adjacent tertiary-lower-alkyl, lower-alkoxy, non-adjacent trihalomethyl, non-adjacent nitro and halo; where lower-alkyl, lower-alkoxy and lower-alkanoyl, every occurrence, have from one to six carbon atoms, lower-alkenyl has from three to six carbon atoms and lower-alkylene has from two to four carbon atoms.

A preferred group of compounds of this invention are the compounds of formula I where R is hydrogen or lower-alkyl, $Q_1$ is selected from hydrogen, lower-alkyl, halo, Ar-O and Ar and $Q_2$, $Q_3$ and $Q_4$ are selected from hydrogen, lower-alkyl and halo.

A more preferred group of compounds of this invention are the compounds of formula I where N=B is NHR' or NR'R", where R' and R" are lower-alkyl, R is hydrogen or lower-alkyl, $Q_1$ is selected from hydrogen, lower-alkyl, halo, Ar-O and Ar and $Q_2$, $Q_3$ and $Q_4$ are selected from hydrogen, lower-alkyl and halo.

A more particularly preferred group of compounds of this invention are the compounds of formula I where N=B is methylamino or dimethylamino, R is hydrogen and $Q_1$, $Q_2$, $Q_3$ and $Q_4$ are selected from hydrogen, lower-alkyl and halo.

Two especially preferred groups of compounds of this invention are the compounds of formula I where N=B is methylamino or dimethylamino, R is hydrogen, $Q_1$ and $Q_2$ are hydrogen and $Q_3$ and $Q_4$ either are selected from hydrogen and fluoro or from hydrogen and methyl.

In another aspect of this invention there is provided 3-(dimethylamino)-6-fluoro-9-(4-fluorophenyl)-1,2,3,4-tetrahydrocarbazole having the structural formula

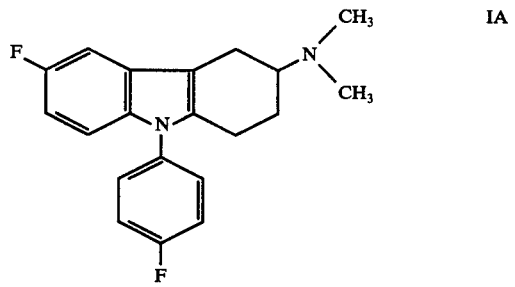

IA

By virtue of possessing an asymetric carbon atom, that is, the carbon atom at the 3-position of the 1,2,3,4-tetrahydrocarbazole ring, each of the compounds within the scope of formulas I and the compound of formula IA can exist as optical isomers, that is, in two stereoisomeric forms (enantiomers), whose molecular structures are mirror images of each other. Therefore, within the purview of this invention are the dextrorotatory isomers and levorotatory isomers, hereinafter the the d- and l-isomers, and the d,l-mixtures thereof, hereinafter racemic mixtures, of the compounds of formulas I and IA. The racemic mixture of any paricular compound within the scope of formulas I and IA, obtained directly by the synthetic procedures described hereinbelow, is separated into the d-isomer and l-isomer, using standard resolution procedures. Thus the racemic mixture is converted to a mixture of two diastereomeric acid-addition salts by reaction, using standard procedures, with a suitable optically active acid, e.g., d-tartaric acid, l-malic acid, l-mandelic acid, d-camphor-10-sulfonic acid, dibenzoyl l-tartaric acid and the like and the resulting two diastereomeric salts in the mixture, which are no longer identical or mirror images and therefore possess different physical properties, are separated by conventional physical procedures such as crystallization. The two separated diastereomeric salts so obtained can then be converted by standard procedures, e.g., by treatment with base, to the corresponding d-isomer and l-isomer.

In a further aspect of this invention there are provided novel 3-(NR'''-CO-$R_5$)-1,2,3,4,-tetrahydrocarbazoles having the structural formula

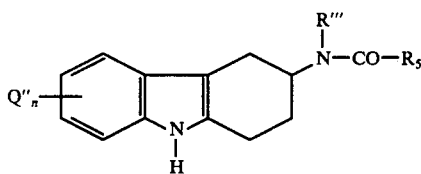

where $R_5$ is hydrogen, lower-alkyl or Ar; R''' is hydrogen or lower-alkyl; Q'' is fluoro; n is an integer from 1 to 4; and Ar is phenyl or phenyl substituted by from one to three of the same or different substituents selected from non-tertiary-lower-alkyl, non-adjacent tertiary-lower-alkyl, lower-alkoxy, non-adjacent trihalomethyl, non-adjacent nitro and halo; where lower-alkyl and lower-alkoxy, every occurrence, have from one to six carbon atoms.

In still another aspect of this invention there are provided novel 3-(OZ)-9-$R_4$-1,2,3,4-tetrahydrocarbazoles having the structural formula

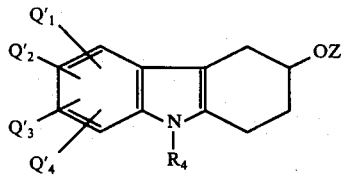

where Z is hydrogen or

$R_4$ is hydrogen, lower-alkyl, Ar-lower-alkyl, lower-alkenyl, carboxy-lower-alkyl or lower-alkoxycarbonyl-lower-alkyl, or $R_4$ is Y-NR'R'', where R' and R'' are lower-alkyl or Ar-lower-alkyl, or R' and R'' taken together with the nitrogen form a heterocyclic ring selected from 4-morpholinyl, 4-thiomorpholinyl, 1-piperidinyl, 1-pyrrolidinyl, 1-piperazinyl, 4-lower-alkyl-1-piperazinyl and 4-Ar-1-piperazinyl and Y is lower-alkylene; $Q'_1$ is selected from the substituents of the groups designated (1), (3) and (4) below; $Q'_2$ is selected from the substituents of the groups designated (2), (3) and (4) below; $Q'_3$ is selected from the substituents of the groups designated (3) and (4) below; $Q'_4$ is selected from the substituents of the groups designated (2) and (4) below, where the substituents of the groups designated (1), (2), (3), and (4) are respectively: (1) Ar-lower-alkyl, Ar-O and Ar, (2) tertiary-lower-alkyl, Ar-lower-alkoxy, trihalomethyl, nitro, di(lower-alkyl)amino and lower-alkanoylamino, (3) lower-alkylthio, lower-alkyl-sulfinyl and lower-alkyl-sulfonyl, and (4) hydrogen, non-tertiary-lower-alkyl, lower-alkoxy and halo, provided that when Z is hydrogen then $R_4$ cannot be lower-alkoxycarbonyl-lower-alkyl, when $R_4$ is hydrogen or lower-alkyl at least one of $Q'_1$, $Q'_2$, $Q'_3$ and $Q'_4$ is other than hydrogen or lower-alkyl, when $Q'_2$ and $Q'_4$ are selected from the substituents of the group designated (2) they are non-adjacent and when $Q'_1$ and $Q'_2$ or $Q'_1$, $Q'_2$ and $Q'_3$ are selected from the substituents of the group designated (3) they are identical; and Ar is phenyl or phenyl substituted by from one to three of the same of different substituents selected from non-tertiary-lower-alkyl, non-adjacent tertiary-lower-alkyl, lower-alkoxy, non-adjacent trihalomethyl, non-adjacent nitro and halo; where lower-alkyl, lower-alkoxy and lower-alkanoyl, every occurrence, have from one to six carbon atoms, lower-alkenyl has from three to six carbon atoms and lower-alkylene has from two to four carbon atoms.

In yet another aspect of this invention there are provided novel 3-(O$Z_1$)-9-$R'_4$-1,2,3,4-tetrahydrocarbazoles having the structural formula

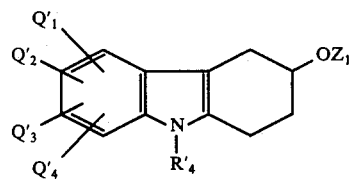

where $Z_1$ is Ar—$SO_2$—, Ar-lower-alkyl-$SO_2$-, or lower-alkyl—$SO_2$—; $R'_4$ is hydrogen, lower-alkyl, Ar-lower-alkyl, lower-alkenyl or carboxy-lower-alkyl, or $R'_4$ is Y-NR'R'', where R' and R'' are lower-alkyl or Ar-lower-alkyl, or R' and R'' taken together with the nitrogen form a heterocyclic ring selected from 4-morpholinyl, 4-thiomorpholinyl, 1-piperidinyl, 1-pyrrolidinyl, 1-piperazinyl, 4-lower-alkyl-1-piperazinyl and 4-Ar-1-piperazinyl and Y is lower-alkylene; $Q'_1$ is selected from the substituents of the groups designated (1), (3) and (4) below; $Q'_2$ is selected from the substituents of the groups designated (2), (3) and (4) below; $Q'_3$ is selected from the substituents of the groups designated (3) and (4) below; $Q'_4$ is selected from the substituents of the groups designated (2) and (4) below, where the substituents of the groups designated (1), (2), (3) and (4) are respectively: (1) Ar-lower-alkyl, Ar-O and Ar, (2) tertiary-lower-alkyl, Ar-lower-alkoxy, trihalomethyl, nitro, di(lower-alkyl)amino and lower-alkanoylamino, (3) lower-alkylthio, lower-alkyl-sulfinyl and lower-alkyl-sulfonyl, and (4) hydrogen, non-tertiary-lower-alkyl, lower-alkoxy and halo, provided that when $Q'_2$ and $Q'_4$ are selected from the substituents of the group designated (2) they are non-adjacent and when $Q'_1$ and $Q'_2$ or $Q'_1$, $Q'_2$ and $Q'_3$ are selected from the substituents of the group designated (3) they are identical; and Ar is phenyl or phenyl substituted by from one to three of the same or different substituents selected from non-tertiary-lower-alkyl, non-adjacent tertiary-lower-alkyl, lower-alkoxy, non-adjacent trihalomethyl, non-adjacent nitro and halo; where lower-alkyl, lower-alkoxy and lower-alkanoyl, every occurrence, have from one to six carbon atoms, lower-alkenyl has from three to six carbon atoms and lower-alkylene has from two to four carbon atoms.

The compounds of this invention having the formula I were found to be therapeutically active substances which possess useful pharmacodynamic properties as determined by test procedures more fully disclosed hereinbelow. Thus, they possess analgetic and psychotropic activities and are indicated for use as analgetic and psychotherapeutic agents. Moreover, certain of these compounds also possess antihistaminic activity and are indicated for use as antihistamines. The compound of formula IA possesses analgetic activity and is indicated for use as an analgetic agent.

Compounds having the formulas II, IIA and IIB are useful as intermediates in the preparation of the novel compounds of formula I.

Here and throughout the specification it will be understood that when Ar bears substituents, as defined hereinbefore, such substituents can be attached to any of the available positions of the Ar ring and when there are two or three such substituents they can be the same or different and they can be in any of the various position combinations relative to each other except as otherwise defined hereinbefore. Similarly it will be understood that substituents represented by $Q_1$, $Q_2$, $Q_3$ and $Q_4$ (hereinafter $Q_{1-4}$), $Q'_1$, $Q'_2$, $Q'_3$ and $Q'_4$ (hereinafter $Q'_{1-4}$) and $Q''$, defined hereinbefore, may be attached to any of the available positions, i.e., the 5,6,7 and 8 positions, of the 1,2,3,4-tetrahydrocarbazole ring and corresponding positions of the phenyl ring of the phenylhydrazine starting materials (IV and IVA below) and where there are more than one such substituents they can be in any of the various position combinations relative to each other except as otherwise defined hereinbefore.

It will also be understood that as used throughout this specification, $N\!=\!B$, R, Ar, $Q_{1-4}$, $R_4$, $R'_4$, $Q'_{1-4}$, $Q''$, Z and $Z_1$ each have the meaning hereinbefore defined except where otherwise specifically defined hereinbelow.

As used throughout this specification, the term "halo" includes chloro, bromo, iodo and fluoro; the terms "lower-alkyl, " "lower-alkanoyl, " and "lower-alkoxy" mean such groups preferably containing from one to six carbon atoms which can be arranged as straight or branched chains, and, without limiting the generality of the foregoing, are illustrated by methyl, ethyl, propyl, isopropyl, butyl, sec.-butyl, amyl, hexyl and the like for lower-alkyl, acetyl, propionyl, trimethylacetyl hexanoyl and the like for lower-alkanoyl, and methoxy, ethoxy, isobutoxy, tert-butoxy, hexoxy and the like for lower-alkoxy; the term "lower-alkylene" means a group preferably containing from two or four carbon atoms with its connecting linkages on different carbon atoms, and without limiting the generality of the foregoing, is illustrated by 1,2-ethylene, 1,3-propylene, 1,2-(1-methylethylene), 1,4-butylene, and the like; and the term "lower-alkenyl" means a group preferably containing from three to six carbon atoms which can be arranged in straight or branched chains, and, without limiting the generality of the foregoing, is illustrated by allyl, 2-butenyl, 3-methyl-2-butenyl, and the like.

The novel 1,2,3,4-tetrahydrocarbazole finel products of the instant invention are the compounds of formulas I and IA and the acid-addition and quaternary ammonium salts thereof. The compounds of formulas I and IA, in free base form, are converted to the acid-addition salt form by interaction of the base with an acid. Conversely, the free bases can be regenerated from the acid-addition salt form in a conventional manner, that is, by treating the salts with strong aqueous bases, for example alkali metal hydroxides, alkali metal carbonates, and alkali metal bicarbonates. The bases thus regenerated can then be interacted with the same or a different acid to give back the same or a different acid-addition salt. Thus the novel bases and all of their acid-addition salts are readily inter-convertible.

It will thus be appreciated that Formula I not only represents the structural configuration of the bases of Formula I but is also representative of the structural entity which is common to all of my compounds of Formula I, whether in the form of the free bases or in the form of the acid-addition salts of the bases. I have found that by virtue of this common structural entity, the bases and their acid-addition salts have inherent pharmacodynamic activity of a type more fully described hereinbelow. This inherent pharmacodynamic activity can be enjoyed in useful form for pharmaceutical purposes by employing the free bases themselves or the acid-addition salts formed from pharmaceutically-acceptable acids, that is, acids whose anions are innocuous to the animal organism in effective doses of the salts so that beneficial properties inherent in the common structural entity represented by the free bases are not vitiated by side-effects ascribable to the anions.

In utilizing this pharmacodynamic activity of the salts of the invention, I prefer of course to use pharmaceutically-acceptable salts. Although water-insolubility, high toxicity, or lack of crystalline character may make some particular salt species unsuitable or less desirable for use as such in a given pharmaceutical application, the water-insoluble or toxic salts can be converted to the corresponding pharmaceutically-acceptable bases by decomposition of the salt with aqueous base as explained above, or alternatively, they can be converted to any desired pharmaceutically-acceptable acid-addition salt by double decomposition reactions involving the anion, for example, by ion-exchange procedures.

Moreover, apart from their usefulness in pharmaceutical applications, my salts are useful as characterizing or identifying derivatives of the free bases or isolation or purification procedures. Like all of the acid-addition salts, such characterizing or purification salt derivatives can, if desired, be used in regenerate the pharmaceutically-acceptable free bases by reaction of the salts with aqueous base, or alternatively can be converted to a pharmaceutically-acceptable acid-addition salt by, for example, ion-exchange procedures.

It will be appreciated from the foregoing that all of the acid-addition salts of my new bases are useful and valuable compounds, regardless of considerations of solubility, toxicity, physical form, and the like, and are accordingly within the purview of the instant invention.

The novel feature of the compounds of the invention, then, resides in the concept of the bases and cationic forms of the new 3-($N\!=\!B$)-9-R-1,2,3,4-tetrahydrocarbazoles and not in any particular acid moiety or acid anion associated with the salt forms of my compounds; rather, the acid moieties or anions which can be associated in the salt forms are in themselves neither novel nor critical and therefore can be any acid anion or acid-like substance capable of salt formation with bases. In fact, in aqueous solutions, the base form or water-soluble acid-addition salt form of the compounds of the invention both possess a common protonated cation or ammonium ion.

Thus the acid-addition salts discussed above and claimed herein are prepared from any organic acid, inorganic acid (including organic acids having an inorganic group therein), or organo-metallic acid as exemplified by organic mono- and polycarboxylic acids, such as found, for example, in Beilstein's Organische Chemie, 4th ed., Volumes III, IV, IX, X, XIV, XVII, XIX, XXI, XXII, and XXV; organic mono- and polysulfonic and -sulfinic acids, such as found, for example, in Beilstein Volumes VI, XI, XVI, and XXII; organic phosphonic and phosphinic acids, such as found, for example, in Beilstein Volumes XI and XVI; organic acids of arsenic and antimony, such as found, for example, in Beilstein Volume XVI; organic heterocyclic, carboxylic, sulfonic, and sulfinic acids, such as found, for example, in Beilstein Volumes XVIII, XXII, and XXV; acidic ion-exchange resins; and inorganic acids of any acid forming element or combination of elements, such as found in Mellor, Comprehensive Treatise on Inorganic and Theoretical Chemistry, Longman's, Green and Co., New York, N.Y. Volumes I-XVI. In addition, other salt-forming compounds which are acidic in their chemical properties but which are not generally considered as acids in the same sense as carboxylic or sulfonic acids are also considered to be among the numerous acids which can be used to prepare acid-addition salts of the compounds of the invention. Thus there is also comprehended acidic phenolic compounds, such as found, for example, in Volume VI of Beilstein, acidic compounds having "activated" or acid hydrogen atoms, as for example, picrolonic acid, or barbituric acid derivatives having an acidic proton, such as found, for example in Cox et al. Medicinal Chemistry, Vol. IV, John Wiley and Sons, Inc., New York, N.Y. (1959). Also comprehended as salt forming agents are so-called Lewis acids which lack a pair of electrons in the outer "electron shell" and react with basic compounds having an unshared pair of electrons to form salts, for example boron trifluoride.

Representative acids for the formation of the acid-addition salts include formic acid, acetic acid, trifluoroacetic acid, isobutyric acid, alpha-mercaptopropionic acid, malic acid, fumaric acid, oxalic acid, succinic acid, succinamic acid, glutamic acid, tartaric acid, citric acid, pamoic acid, lactic acid, glycolic acid, gluconic acid, saccharic acid, ascorbic acid, penicillin, benzoic acid, 4-methoxybenzoic acid, phthalic acid, salicylic acid, acetylsalicylic acid, anthranilic acid, 1-naphthalenecarboxylic acid, cinnamic acid, cyclohexanecarboxylic acid, mandelic acid, tropic acid, crotonic acid, acetylene dicarboxylic acid, sorbic acid, pyromucic acid, cholic acid, pyrenecarboxylic acid, 2-pyridinecarboxylic acid, 3-indoleacetic acid, quinic acid, sulfamic acid, methanesulfonic acid, ethanesulfonic acid, isethionic acid, benzenesulfonic acid, p-toluenesulfonic acid, benzenesulfinic acid, butylarsonic acid, diethylphosphinic acid, p-aminophenylarsinic acid, phenylstibnic acid, phenylphosphinous acid, methanephosphonic acid, phenylphosphinic acid, acidic resins, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

The acid-addition salts are prepared either by dissolving the free base in an aqueous solution containing the appropriate acid and isolating the salt by evaporating the solution, or by reacting the free base and acid in an organic solvent, in which case the salt separates directly or can be obtained by concentration of the solution.

The quaternary ammonium salts of the compounds of Formula I are obtained by the addition of esters of strong acids to the free base form of the compounds, said esters having a molecular weight less than about 300. A preferred class of esters comprises alkyl, alkenyl, and phenyl-lower-alkyl esters of strong inorganic acids or organic sulfonic acids, including such compounds as methyl chloride, methyl bromide, methyl iodide, ethyl bromide, propyl chloride, allyl chloride, allyl bromide, methyl sulfate, methyl benzenesulfonate, methyl p-toluenesulfonate, benzyl chloride, benzyl bromide, and substituted benzyl halides, for example p-chlorobenzyl chloride, 3,4-dichlorobenzyl chloride, 2,3,4,5,6-pentachlorobenzyl chloride, 4-nitrobenzyl chloride, 4-methoxybenzyl choride, and the like.

The quaternary ammonium salts are prepared by mixing the free base and ester of a strong acid in an inert solvent. Heating may be used to facilitate the reaction, although salt formation usually takes place readily at room temperature. The quaternary ammonium salt separates directly or can be obtained by concentration of the solution.

As in the case of the acid-addition salts, water-insolubility, high toxicity, or lack of crystalline character may make some quaternary ammonium salt species unsuitable or less desirable for use as such in a given pharmaceutical application, the water-insoluble or toxic salts can be converted to the corresponding pharmaceutically-acceptable salts by double decomposition reactions involving the anion, for example, by ion-exchange procedures. Alternatively, if the anion of the original quaternary salt forms a water-insoluble silver salt, the quaternary salt will react with silver oxide in aqueous medium to form the corresponding quaternary ammonium hydroxide, the original anion being removed as a precipitate. The quaternary ammonium hydroxide solution can then be neutralized with any desired acid, weak or strong, to produce a new quaternary ammonium salt in which the anion is different from that of the original salt. In this way quaternary ammonium salts in which the anion is derived from a weak acid are formed.

Where the compounds of formula I bear more than one basic substituent, mono- or multiple salts may be obtained by the general procedures described above depending on the relative basicity of such substituents and the relative quantities of the reactants and particular reaction conditions employed in preparing such salts. Thus, for example, where $Q_2$ is an amino substituent and N=B is NHR' or NR'R", or where N=B is NR"'-Y-NR'R", a mono- or di-salt may be formed, and whether a mono- or di-salt is obtained is readily determinable by standard analytical procedures.

The compounds of this invention having the formulas I and IA can be prepared for therapeutic use of dissolving under sterile conditions a salt form of the compounds in water (or an equivalent amount of a non-toxic acid if the free base is used), or in a physiologically compatible aqueous medium such as saline, and stored in ampoules for intramuscular injection. Alternatively, they can be incorporated in unit dosage form as tablets or capsules for oral administration either along or in combination with suitable adjuvants such as calcium carbonate, starch, lactose, talc, magnesium stearate, gum acacia, and the like. Still further the compounds can be formulated for oral administration in aqueous alcohol, glycol, or oil solutions or oil-water emulsions in the same manner as conventional medicinal substances are prepared.

The actual determination of the numerical biological data definitive for a particular compound, for each type of activity, is readily determined by standard test procedures by technicians having ordinary skill in pharmacological test procedures, without the need for any extensive experimentation.

The molecular structures of the compounds of this invention were assigned on the basis of the method of their synthesis and study of their infrared and nuclear magnetic resonance spectra, and confirmed by the correspondence between calculated and found values for the elementary analysis for representative examples.

The novel compounds of this invention of formula I are prepared by one or more of several processes described below.

In one process certain of the compounds of formula I are prepared by displacing the $(OZ_1)$ group of a 3-$(OZ_1)$-9-$R'_4$-1,2,3,4-tetrahydrocarbazole, having the formula IIB above, with an amine of the general formula $HN=B$ (III). The displacement reaction can advantageously be carried out at elevated temperatures ranging from about 60° C. to about 200° C. for about one hour to about 24 hours. The pressure of the system may be varied over a wide range from normal atmospheric pressure to about 600 pounds per square inch gauge (psig). Generally, the reactants are charged into a pressure reaction vessel and heated under autogenous pressure. The reaction is conveniently carried out by heating a 3-$(OZ_1)$-9-$R'_4$-1,2,3,4-tetrahydrocarbazole (IIB) with the amine III in a pressure reaction vessel at a temperature of 90° C. to 150° C. for 20 hours.

The following reaction sequence illustrates the above method of synthesis:

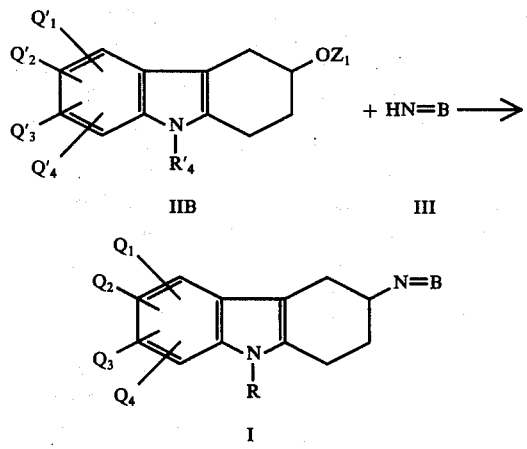

where R and $Q_{1-4}$ are limited to the substituents defined hereinbefore for $R'_4$ and $Q'_{1-4}$.

The intermediate 3-$(OZ_1)$-9-$R'_4$-1,2,3,4-tetrahydrocarbazoles (IIB) are prepared from the corresponding 3-(OH)-9-$R'_4$-1,2,3,4-tetrahydrocarbazoles (VII below) by conventional acid chloride esterification procedures, that is by reaction in a suitable solvent, e.g., pyridine, with an appropriate sulfonyl chloride having the formula $Z_1Cl$ ($Z_1 \neq H$).

The intermediate 3-(OH)-9-$R'_4$-1,2,3,4-tetrahydrocarbazoles (VII) are prepared from the corresponding

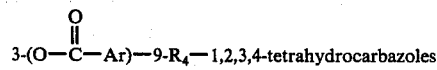

(VI below) by conventional ester hydrolysis procedures, for example, by heating the ester VI in a suitable solvent, e.g., aqueous ethyl alcohol, in the presence of at least one equivalent of a suitable base, e.g., sodium hydroxide or potassium hydroxide. Where $R_4$ of compound VI is lower-alkoxycarbonyl-lower-alkyl, the corresponding compound VII, where $R_4$ is carboxy-lower-alkyl, is obtained.

The intermediate

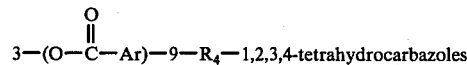

(VI) are prepared by means of the Fischer indole synthesis. Thus, they are obtained by reacting an appropriate phenylhydrazine (IV below) with a

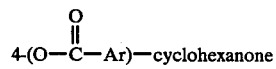

(V below) in an acidic medium, at elevated temperatures, for from about one-half hour to 24 hours. Acids which may be employed as cyclizing agents are inorganic acids such as hydrochloric acid or hydrobromic acid, mineral acids such as sulfuric acid or phosphoric acid, and organic acids such as acetic acid and methanesulfonic acid as well as Lewis acids such as boron trifluoride. The acidic agent should be present in at least one mole excess per mole of the phenylhydrazine. The reaction is conveniently carried out by heating the reactants in acetic acid or in ethanolic hydrochloric acid at reflux temperature for one hour. The reaction proceeds via the corresponding 4-benzoyloxycyclohexanone phenylhydrazone precursor which can be isolated, if desired, if excess acid is avoided, e.g., if the amount of acid employed is not in excess of one equivalent the amount of phenylhydrazine employed. Subsequent treatment of the phenylhydrazone precursor under acidic conditions, as described above, will effect cyclization to the corresponding tetrahydrocarbazole VI.

The following reaction sequence illustrates the above method of synthesis:

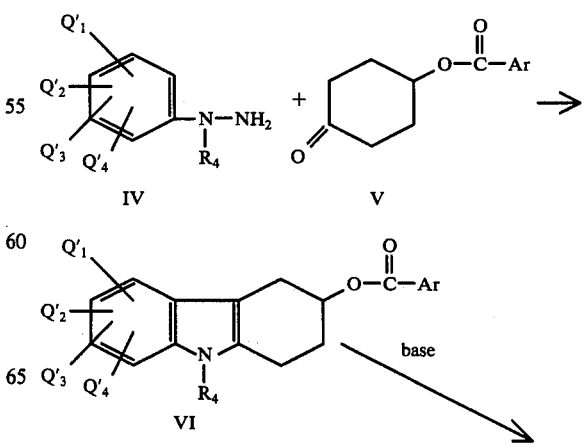

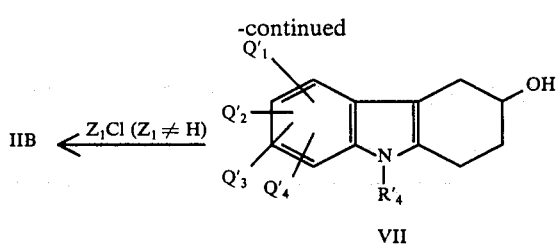

The cyclohexanone starting materials (V) are prepared from 4-hydroxy-cyclohexanone by conventional esterification procedures using known acids or their corresponding acid chlorides.

The sulfonyl chlorides ($Z_1CL$; $Z_1 \neq H$) belong to a well known class of compounds and can be prepared by standard procedures, e.g., by treatment of the corresponding sulfonic acids with a suitable chlorinating agent such as thionyl chloride, phosphorus pentachloride or phosphorus oxychloride.

In a second process certain compounds of formula I are prepared by means of the Fischer indole synthesis, that is, by reacting a 1-R-1-($Q_{1-4}$)-phenylhydrazine (IVA) with a 4-(N=B)-cyclohexanone (VIII) and, if desired, isolating and subsequently cyclizing, the corresponding 4-(N=B)-cyclohexanone phenylhydrazone precursor, using procedures similar to that described hereinbefore for the preparation of the tetrahydrocarbazoles having formula VI. However, the phenylhydrazines (IVA) utilized in this method, and hence compounds of formula I prepared by this method, cannot bear certain substituents represented by $Q_1$, $Q_2$ and $Q_4$ which interfere with or will not survive, the reaction conditions of the Fischer indole synthesis and such substituents are introduced subsequent to the cyclization procedure as described hereinbelow. The following reaction sequence illustrates the synthetic method:

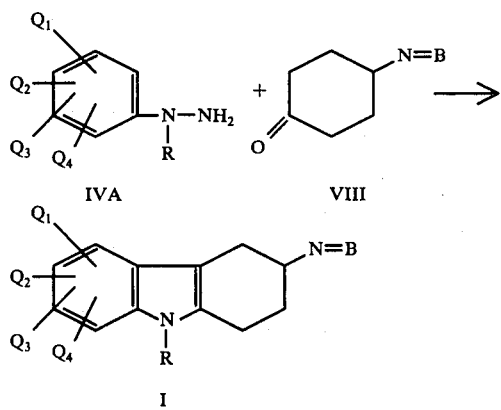

In either of the two above-described processes for the preparation of the compounds of formula I, when the phenylhydrazine (IV or IVA) is unsymmetrically substituted by one or two $Q'_{1-4}$ or $Q_{1-4}$ substituents respectively and bears a hydrogen atom on each α-position of the phenyl ring, cyclization can occur at either of the α-positions and thus generally two isomeric tetrahydrocarbazoles are obtained. The relative amounts of the two isomers so obtained will vary depending on the degree of substitution and the nature of the substituents. The isomers can be separated by means of conventional isolation and purification procedures. The formation of two isomers can be avoided, if desired, by utilizing in the cyclization reaction an appropriately substituted phenylhydrazine additionally bearing an α-bromo or α-chloro substituent on the phenyl ring. The corresponding 8-bromo or 8-chloro substituent of the compound of formula I thus obtained by either of the above-described procedures is then reductively removed by catalytic hydrogenation. The hydrogenation can be carried out at room temperature in a suitable solvent, e.g., ethyl or methyl alcohol, in the presence of palladium on charcoal catalyst at atmospheric or elevated pressure. The hydrogenation can be performed under neutral conditions but is preferably carried out in the presence of at least an equivalent amount of an acidacceptor such as potassium hydroxide.

The compound of formula IA can be prepared by the above-described Fischer indole procedure by reaction of the known 1,1-bis(4-fluorophenyl)hydrazine with 3-dimethylaminocyclohexanone.

The 4-(N=B)-cyclohexanone starting materials (VIII) are prepared from 4-(p-toluenesulfonyloxy)-cyclohexanone by displacement of the p-toluenesulfonyloxy group with the amine HN=B (III), using the procedure described hereinabove, followed by conventional acid hydrolysis of the resulting 4-(N=B)-cyclohexanone enamine, or are prepared from 4-hydroxycyclohexanone by reaction with the amine HN=B (III), using conventional procedures, to obtain the corresponding 4-hydroxycyclohexanone enamine, catalytic reduction of the latter, e.g., over 10% palladium on charcoal, and finally oxidation of the resulting 4-(N=B)-cyclohexanol, using conventional oxidation procedures, e.g., with chromium trioxide in acetic acid or in acetone-sulfuric acid, to give the corresponding 4-(N=B)-cyclohexanone.

The phenylhydrazine starting materials (IV and IVA) belong to a class of compounds well known in the art of organic chemistry and can be prepared by well known methods of synthesis, for example, by reaction of the corresponding ($Q_{1-4}$)-NR- and ($Q'_{1-4}$)-NR$_4$- anilines, where $Q_1$, $Q_2$ and $Q_4$ cannot represent certain substituents as described hereinbelow, with sodium nitrite in water in the presence of hydrochloric acid and subsequent reduction of the diazonium chloride or N-nitroso intermediate so obtained with an appropriate reducing agent, e.g., stannous chloride ($SnCl_2$) or lithium aluminum hydride. The hydrochlorides of the resulting hydrazines are prepared by conventional methods.

The HN=B (III) starting materials are well known in the art of organic chemistry and are generally available or can be prepared by conventional processes. For example, diamines represented by the formula HN=B, where N=B is NR'''-Y-NR'R'', can be prepared by reacting an appropriate amine, for example, a 1-phenyl-piperazine, with a halo-lower-alkyl-nitrile, for example, chloroacetonitrile, to give an amino-lower-alkyl-nitrile, for example, a (4-phenyl-1-piperazinyl)-acetonitrile, which can then be reduced by conventional methods to the corresponding diamine (R'''=H), for example, a 2-(4-phenyl-1-piperazinyl)-ethylamine. The diamines where R''' is lower-alkyl can be prepared from the corresponding diamines where R''' is hydrogen by conventional acylation procedures, e.g., by reaction with formic acid or formamide or an appropriate lower-alkanoic acid halide, followed by conventional chemical reduction of the corresponding amides so obtained, e.g., with lithium aluminum hydride. The lower-alkanoic acid halides are known compounds or are readily prepared by conventional procedures from the known acids. In a similar manner compounds of formula I where N=B is NHR' or NR'R", where R' and R" are lower-alkyl or Ar-lower-alkyl, or N=B is NR'''-Y-NR'R", where R''' is lower-alkyl are prepared from the corresponding 3(NH₂)- or 3-(N=B)-1,2,3,4-tetrahydrocarbazoles where N=B is NHR' or NH-Y-NR'R" respectively, by reaction with formamide or an appropriate carboxylic acid halide followed by chemical reduction of the corresponding 3-amido-1,2,3,4-tetrahydrocarbazole so obtained. Where R of formula I is hydrogen, the acylation step is preferably carried out with formamide or under aqueous conditions, that is, by reacting the appropriate amino compound with an appropriate loweralkanoic acid halide in dilute aqueous alkali, e.g., dilute sodium hydroxide solution, in order to avoid acylation of the unsubstituted tetrahydrocarbazole nitrogen atom (position 9). Alternatively, the 3-amido-1,2,3,4-tetrahydrocarbazole intermediates can be obtained directly by means of the Fischer indole synthesis by employing an appropriate 4-amidocyclohexanone. The latter can be prepared from the corresponding 4-(NH₂)- or 4-(N=B)-cyclohexanone (IX), where N=B is NHR' or NH-Y-NR'R", by the conventional N-acylation methods disclosed above.

Compounds of formula I where $Q_2$ and/or $Q_4$ are lower-alkanoylamino or lower-alkylamino can be prepared from the corresponding compounds where $Q_2$ and/or $Q_4$ are amino using the conventional N-acylation and chemical reductive methods disclosed above.

The compounds of formula I and formula VI when prepared by the processes described above, can be substituted at the 9-position by hydrogen (R and $R_4$=H respectively) or by other substituents as hereinbefore defined for R and $R_4$. When R and $R_4$ are hydrogen, then appropriate substituents, if desired, can be introduced at the 9-position be reacting these compounds with a compound of the formula RX or $R_4$X (R and $R_4$ ≠ H) respectively wherein X is chlorine, bromine or iodine, in a suitable solvent at elevated temperatures and in the presence of a strong base for about one-half hour to eight hours. The reaction is preferably carried out in dimethylformamide in the presence of sodium hydride at 75° C. to 90° C for about two hours. Where R and $R_4$ are carboxy-lower-alkyl or lower-alkoxycarbonyl-lower-alkyl or R is Ar-lower-alkoxycarbonyl-lower-alkyl, such substituents can also be introduced by reacting the corresponding compounds where R and $R_4$ are hydrogen with acrylonitrile or an appropriate acrylic acid ester to give the corresponding cyanoethyl or carboxyethyl ester compounds, and in the case of the former compound, further treating that compound under aqueous hydrolysis conditions, e.g., in aqueous ethanolic potassium hydroxide under reflux for several hours, to give the corresponding carboxyethyl compound.

The RX and $R_4$X(R and $R_4$ ≠ H) starting materials are generally well known in the art of organic chemistry and can be prepared readily by conventional processes, for example, by reaction of the corresponding alcohols in a suitable solvent with a suitable acid halide, e.g., thionyl chloride, in the presence of a base, e.g., pyridine. The acrylic acid esters are generally known compounds.

Compounds of formula I, where $Q_2$ and $Q_4$ are selected from amino and hydroxy substituents, or where $Q_1$ is selected from the substituents of the group designated (I), defined hereinabove, excluding Ar-lower-alkyl, Ar-O, Ar and

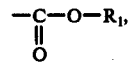

are not prepared directly by the Fischer indole procedure described hereinabove but can be prepared by the methods described as follows:

The compounds of formula I where $Q_2$ and $Q_4$ are selected from amino and hydroxy substituents can be prepared by well known catalytic hydrogenation procedures from the corresponding compounds where $Q_2$ and $Q_4$ are selected from nitro and benzyloxy substituents, whereby said substituents are converted to amino and/or hydroxy substituents. The hydrogeneration can be carried out at room temperature in an inert solvent, e.g., ethyl alcohol, under essentially neutral conditions in the presence of a suitable catalyst, e.g., Raney nickel or palladium on charcoal, at atmospheric or elevated pressures, the hydrogenation being stopped after a shoichiometric amount of hydrogen has reacted.

The compounds of formula I where $Q_1$ is formyl,

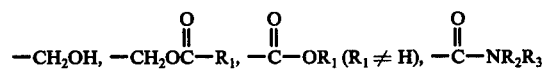

and —CH₂NR₂R₃ can be prepared from the corresponding compound, where $Q_1$ is carboxy, by conventional procedures, more fully described hereinbelow, well known in the art of organic chemistry.

Compounds of formula I wherein $Q_1$ is

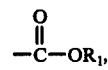

wherein $R_1$ is lower-alkyl, Ar or —CH₂—Ar, can be prepared from the corresponding compounds where $Q_1$ is carboxy by conversion of said carboxy compound to the acid chloride using conventional procedures, for example, reaction in a suitable solvent with thionyl chloride, and reaction of the acid chloride so obtained with an alcohol of the formula R₁OH (R₁ ≠ H), both reaction steps being carried out in the presence of a suitable acid acceptor, e.g., pyridine or triethylamine. However, when a carboxyphenylhydrazine, is employed in the Fischer indole synthesis and the reaction is carried out in an appropriate alcohol, e.g., ethyl alcohol, in the presence of excess acid, the corresponding ester, e.g., ethyl ester, is obtained directly.

Compounds of formula I wherein $Q_1$ is

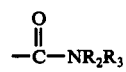

can be prepared from the corresponding acid chlorides described hereinabove by reaction with an amine having the formula R₂R₃NH in the presence of a suitable acid acceptor, e.g., pyridine or triethylamine.

Compounds of formula I wherein $Q_1$ is —CH₂OH or —CH₂NR₂R₃ can be prepared by reduction of the corresponding esters or amides, i.e., corresponding compounds where $Q_1$ is

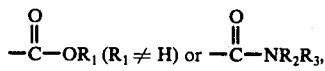

respectively using conventional reduction procedures. A preferred procedure is chemical reduction of the ester or amide. Conveniently the ester or amide, in a suitable solvent, e.g., ether or tetrahydrofuran, is treated with lithium aluminum hydride (LAH) for from about one to about twenty hours and the resulting alcoholate is decomposed with acid, e.g., dilute hydrochloric acid. The reaction is generally carried out at temperatures ranging from about 20° C. to about 60° C.

The compounds of formula I wherein $Q_1$ is

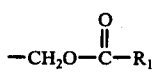

can be prepared from the correspondig compounds wherein $Q_1$ is $-CH_2OH$ by reaction with an acid chloride having the formula

or equivalent acid halides, by the conventional procedure for reacting an acid chloride and an alcohol as described hereinabove.

The acid chlorides

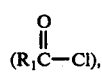

the amines ($R_2R_3NH$) and the alcohols ($R_1OH$, $R_1 \neq H$) used in the above-described methods of synthesis belong to well-known classes of compounds and are readily available or prepared from readily available starting materials using well-known procedures.

The compounds of formula I wherein $Q_1$ is formyl

can be prepared from the corresponding compounds where $Q_1$ is $-CH_2OH$ by a conventional oxidation procedure, i.e., by manganese dioxide ($MnO_2$) oxidation. The reaction is conveniently carried out by treating a solution of the alcohol ($Q_1= -CH_2OH$) in a suitable solvent, e.g., acetone, with an excess of manganese dioxide at about 20° C. to about 50° C. for from one to twenty hours.

The compounds of formula I where $Q_1$ is cyano are prepared from the corresponding compounds where $Q_1$ is bromo or chloro by reaction with cuprous cyanide in a suitable solvent at elevated temperatures. The reaction is conveniently performed in dimethylformamide at reflux temperature for about four hours.

The following reaction sequences illustrate the above-described methods of synthesis.

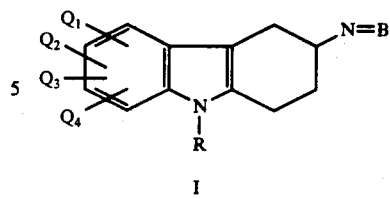

I where $Q_1$ is Cl or Br

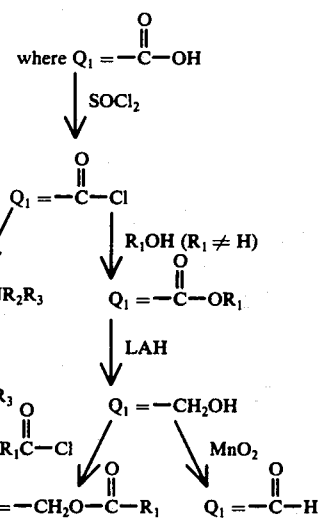

Psychotropic activity of the compounds of this invention was determined in the test procedures described hereinbelow.

1a. RESERPINE PTOSIS PREVENTION IN MICE

Unfasted male mice, grouped in cages of eight animals each, were injected intraperitoneally (IP) with the test agent. Two hours later the mice were injected IP with 2 mg./kg. of reserpine. Three hours after the administration of reserpine the degree of eyelid ptosis was scored. If the test agent was significantly active, the minimal dose at which activity was noted was determined.

1b. RESERPINE PTOSIS REVERSAL IN MICE

This test is similar to Test 1a described above, except the mice first received reserpine, and three hours later, when ptosis was evident, they were challenged with the test agent. Each mouse was scored one-half hour after the drug injection.

2. OVERT BEHAVIORAL EFFECTS IN MONKEYS AND CATS

The animals were medicated orally (PO) with the test agent and observed for changes in behavior. The pretest agent scored overt behavioral profile was compared to the post-test agent overt behavioral profile at various intervals.

3. SPONTANEOUS PSYCHOMOTOR ACTIVITY OF MICE

The effect of the test agent on the spontaneous activity of mice was determined in a photocell-counter activity cage. Thirty minutes before being placed in the activity cage, groups of four mice each were medicated orally (PO) with graded doses of the test agent. Activity (phychomotor stimulation or depression) was measured by means of a digital counter recording the number of times a beam of light impinging on a photocell was broken during a thirty-minute period.

4. HEXOBARBITAL POTENTIATION

Groups of ten male mice were medicated orally (PO) and intraperitoneally (IP) with the test agent at 100 mg./kg. and 10 mg./kg. both forty and ninety minutes prior to a subhypnotic dose of sodium hexobarbital (40 mg./kg.) injected IP. The mice were tested for loss of righting reflux ten, fifteen, and twenty minutes following the sodium hexobarbital injection. The test was considered positive if the mice lost their righting reflex for one minute.

5. MAXIMAL ELECTROSHOCK

Groups of ten male mice were medicated orally (PO) and intraperitoneally (IP) with the test agent at 100 mg./kg. and 10 mg./kg. both thirty and ninety minutes prior to the application of an electroshock of fifty milliamps of A.C. current for three-tenths of a second through Spiegal Corneal electrodes. The test was considered positive if the mice failed to exhibit the tonic hind-leg extension phase of the seizure.

6. PENTYLANETETRAZOL ANTAGONISM

Groups of ten male mice were medicated orally (PO) and intraperitoneally (IP) with the test agent at 100 mg./kg. and 10 mg./kg. both thirty and ninety minutes prior to a rapid intravenous injection of pentylenetetrazol (50 mg./kg.). The test was considered positive if the tonic hind-leg extension phase of the seizure was blocked.

The antihistaminic activity of the compounds of this invention having Formula I was determined by the following test procedure:

7. ANTIHISTAMINE TEST PROCEDURE

The test agents, made up to appropriate concentrations in distilled water or as suspensions in 1% gum tragacanth, were injected subcutaneously (SC) 30 minutes prior to the intravenous administration of a challenging dose of 0.57 mg./kg. (as base) of histamine diphosphate into albino guinea pigs separated into groups of three pigs each. Two groups of five pigs each served as controls and these pigs received subcutaneous injections of 1 ml./kg. of 1% gum tragacanth and distilled water, respectively, thirty minutes prior to the challenging dose of the histamine. All of the control animals died. The doses at which fifty-percent of the pigs were protected by the active test agents were recorded as $ED_{50}\pm$ standard error.

The analgetic activity of the compounds of this invention having Formula I was determined by the following test procedure:

8. ANALGETIC TEST PROCEDURE

Inhibition of Phenylquinone - Induced Writhing in Mice

The test agent was administered subcutaneously prior to intraperitoneal injection of phenyl-p-quinone (PPQ). After PPQ treatment the mice are observed, and the total number of writhes for each mouse during specified intervals is recorded. More than 98% of the control mice writhe at least 3 times during the observation period. Any animal writhing $\leq 0\ 2$ times is considered protected. The percent of mice protected is plotted against dose (30 animals per dose) for determination of the $ED_{50}$. ($ED_{50}$ is the dose at which 50% of the mice were protected).

The novel compounds of this invention having Formula I were found to have useful analgetic activity when administered subcutaneously to mice in the dose range of 3 mg./kg. to 100 mg./kg.

For purposes of comparison, the known compound, 3-amino-1,2,3,4-tetrahydrocarbazole hydrochloride was prepared by heating 18.8 g. of 3-p-toluenesulfonyloxy-1,2,3,4-tetrahydrocarbazole with 300 ml. of a solution of ethyl alcohol saturated with ammonia, in a pressure reaction vessel, at 100° C. to 119° C. for twelve hours. The mixture was evaporated to dryness and the residue was treated with 10% sodium hydroxide solution. The resulting free base was collected by filtration and on treatment with ethanolic hydrogen chloride was converted to 3-amino-1,2,3,4-tetrahydrocarbazole hydrochloride which was collected by filtration and which melted at 298°–299° C. (corr.).

The known 3-amino-1,2,3,4-tetrahydrocarbazole was completely inactive in the antihistamine test procedure (7).

Test procedure 1a: active at 30 mg./kg.
Test procedure 1b: active at 10 mg./kg.
Test procedure 3: active at 8 mg./kg.

My invention is illustrated by the following examples without, however, being limited thereto.

EXAMPLE 1

3-(Dimethylamino)-1,2,3,4-tetrahydrocarbazole

To a refluxing solution of 9.2 g. of 4-dimethylaminocyclohexanone in 23.5 g. of glacial acetic acid was added dropwise 7.1 g. of phenylhydrazine and the mixture refluxed for one hours. The solvent was removed by distillation under reduced pressure, the residue made basic with dilute sodium hydroxide solution and extracted with ehter. The ether extracts were dried and the ether evaporated to give an orange solution which crystallized upon cooling. The solid was collected by filtration then recrystallized from methanol to give 4 g. of 3-(dimethylamino)-1,2,3,4-tetrahydrocarbazole which melted at 138°–142° C. (corr.).

Treatment of an absolute alcohol solution of the free base with alcoholic hydrochloric acid gave a white solid which was collected by filtration. There was thus obtained 3-(dimethylamino)-1,2,3,4-tetrahydrocarbazole hydrochloride which melted at 253°–255° C. (uncorr.).

Test procedure 1a: active at 10 mg./kg.
Test procedure 1b: active at 10 mg./kg.
Test procedure 2: taming in monkeys at 4 mg./kg.
Test procedure 4: active at 50 mg./kg. (IP)
This compound was active as an antihistamine at 0.6 $\pm$ 0.1mg./kg. in test procedure 7.

EXAMPLE 2

3-Acetamido-1,2,3,4-tetrahydrocarbazole

Following the procedure given in Example 1 and using 30 g. of 4-acetamidocyclohexanone and excess phenylhydrazine there was obtained 3 g. of 3-acetamido-1,2,3,4-tetrahydrocarbazole which melted at 165°–167° C. (corr.).

EXAMPLE 3

3-(Dimethylamino)-6-methoxy-1,2,3,4-tetrahydrocarbazole

A mixture of 4-dimethylaminocyclohexanone hydrochloride, prepared from 19.8 g. of 4-dimethylaminocyclohexanone, in alcoholic hydrogen chloride and 24.6 g. of p-methoxyphenylhydrazine hydrochloride in ethanol was warmed on a steam bath for one hour. The ammonium chloride which precipitated was removed by filtration and the filtrate evaporated in vacuo. The solid residue was taken up in water, made basic with dilute sodium hydroxide and extracted with ether. Evaporation of the ether extracts gave an oil which crystallized upon cooling. Recrystallization from ethyl acetate gave 22.4 g. of 3-(dimethylamino)-6-methoxy-1,2,3,4-tetrahydrocarbazole which melted at 126°–128° C. (corr.).

Test procedure 3: active at 100 mg./kg.
Test procedure 4: active at 50 mg./kg. (IP)
Test procedure 7: active at 36.5 ± 7.3 mg./kg.

Alternatively, 3-(dimethylamino)-6-methoxy-1,2,3,4-tetrahydrocarbazole can be prepared by following the procedure given in Example 18 below and using 3-(p-toluenesulfonyloxy)-6-methoxy-1,2,3,4-tetrahydrocarbazole and dimethylamine.

The 3-(p-toluenesulfonyloxy)-6-methoxy-1,2,3,4-tetrahydrocarbazole can be prepared from 3-hydroxy-6-methoxy-1,2,3,4-tetrahydrocarbazole and tosyl chloride by following a procedure similar to that described in Example 18.

The 3-hydroxy-6-methoxy-1,2,3,4-tetrahydrocarbazole, was prepared as follows:

A suspension of 25.6 g. of 3-benzoyloxy-6-methoxy-1,2,3,4-tetrahydrocarbazole in 250 ml. ethyl alcohol was treated with 50 ml. of an aqueous solution containing 6.5 g. potassium hydroxide and heated on a steam bath for one and one-half hours. The alcohol was distilled under reduced pressure and the residue was treated with ethyl alcohol - water. The resulting precipitate was collected and recrystallized from ethylene dichloride to give 12.3 g. 3-hydroxy-6-methoxy-1,2,3,4-tetrahydrocarbazole; m.p. 119°–122° C.

The 3-benzoyloxy-6-methoxy-1,2,3,4-tetrahydrocarbazole was prepared as follows:

To a suspension of 4-methoxyphenylhydrazine hydrochloride in 200 ml. ethyl alcohol was added 21.8 g. of 4-benzolyoxycyclohexanone and the mixture was heated under reflux for one and one-half hours. The mixture was filtered and the filtrate was evaporated to dryness under reduced pressure; the residue was slurried in water and the resulting 3-benzoyloxy-6-methoxy-1,2,3,4-tetrahydrocarbazole, m.p. 135°–141° C., was collected by filtration.

By following the procedure described in Example 3, substituting for p-methoxyphenylhydrazine hydrochloride an equivalent amount of an acid-addition salt of:
a. 2-ethylphenylhydrazine
b. 4-benzylphenylhydrazine
c. 5-ethoxy-2-nitrophenylhydrazine
d. 4-propoxyphenylhydrazine
e. 4-methylthiophenylhydrazine
f. 4-methylsulfinylphenylhydrazine
g. 4-methylsulfonylphenylhydrazine
h. 4-chloro-2-(trifluoromethyl)-phenylhydrazine
i. 4-(diethylamino)-phenylhydrazine
j. 4-acetamidophenylhydrazine
k. 2-benzyloxyphenylhydrazine
l. 2-chloro-5-methoxyphenylhydrazine
m. 5-chloro-4-methyl-2-nitrophenylhydrazine there can be obtained respectively, according to this invention:
a. 3-(dimethylamino)-8-ethyl-1,2,3,4-tetrahydrocarbazole
b. 3-(dimethylamino)-6-benzyl-1,2,3,4-tetrahydrocarbazole
c. 3-(dimethylamino)-5-ethoxy-8-nitro-1,2,3,4-tetrahydrocarbazole
d. 3-(dimethylamino)-6-propoxy-1,2,3,4-tetrahydrocarbazole
e. 3-(dimethylamino)-6-methylthio-1,2,3,4-tetrahydrocarbzole
f. 3-(dimethylamino)-6-methylsulfinyl-1,2,3,4-tetrahydrocarbazole
g. 3-(dimethylamino)-6-methylsulfonyl-1,2,3,4-tetrahydrocarbazole
h. 3-(dimethylamino)-6-chloro-8-(trifluoromethyl)-1,2,3,4-tetrahydrocarbazole
i. 3-(dimethylamino)-6-(diethylamino)-1,2,3,4-tetrahydrocarbazole
j. 3-(dimethylamino)-6-acetamido-1,2,3,4-tetrahydrocarbazole
k. 3-(dimethylamino)-8-benzyloxy-1,2,3,4-tetrahydrocarbazole
l. 3-(dimethylamino)-8-chloro-5-methoxy-1,2,3,4-tetrahydrocarbazole
m. 3-(dimethylamino)-5-chloro-6-methyl-8-nitro-1,2,3,4-tetrahydrocarbazole

EXAMPLE 4

3-(Dimethylamino)-6,7-dimethoxy-1,2,3,4-tetrahydrocarbazole

Following the procedure given in Example 3 and using 14.8 g. of 4-dimethylaminocyclohexanone and 21.5 g. of 3,4-dimethoxyphenylhydrazine hydrochloride there was obtained 3 g. of 3-(dimethylamino)-6,7-dimethoxy-1,2,3,4-tetrahydrocarbazole which melted at 167°–169° C. (corr.).

Test procedure 3: active at 100 mg./kg.

Alternatively, 3-(dimethylamino)-6,7-dimethoxy-1,2,3,4-tetrahydrocarbazole can be prepared by following a procedure similar to that described in Example 18 below and using 3-(p-toluenesulfonyloxy)-6,7-dimethoxy-1,2,3,4-tetra-hydrocarbazole and dimethylamine.

The 3-(p-toluenesulfonyloxy)-6,7-dimethoxy-1,2,3,4-tetrahydrocarbazole can be prepared from 3-hydroxy-6,7-dimethoxy-1,2,3,4-tetrahydrocarbazole and tosyl chloride by following a procedure similar to that described in Example 18.

The 3-hydroxy-6,7-dimethoxy-1,2,3,4-tetrahydrocarbazole, m.p. 197°–199° C., was prepared from the corresponding 3-benzoyloxy derivative by potassium hydroxide hydrolysis following a procedure similar to that described in Example 3.

The 3-benzoyloxy-6,7-dimethoxy-1,2,3,4-tetrahydrocarbazole, m.p. 123°–125° C., was prepared from 102 g. of 3,4-dimethoxyphenylhydrazine and 109 g. of 4-benzoyloxycyclohexanone by following a procedure similar to that described in Example 3.

EXAMPLE 5

6-(Benzyloxy)-3-(dimethylamino)-1,2,3,4-tetrahydrocarbazole

Following the procedure given in Example 3 and using 6.7 g. of 4-dimethylaminocyclohexanone and 11.9 g. of p-benzyloxyphenylhydrazine hydrochloride there was obtained 6-(benzyloxy)-3-(dimethylamino)-1,2,3,4-tetrahydrocarbazole which upon treatment with alcoholic hydrochloric acid gave 8.2 g. of 6-(benzyloxy)-3-(dimethylamino)-1,2,3,4-tetrahydrocarbazole hydrochloride which melted at 209°–212° C. (corr.).

Preparation of 4-benzyloxyphenylhydrazine hydrochloride: To a stirred slurry of 12.5 g. of 4-benzyloxyaniline hydrochloride in 30 ml. concentrated hydrochloric acid and 30 ml. of water, cooled to −5° C., was added dropwise a solution of 4 g. sodium nitrite in 5 ml. of water. With continued cooling at 0° to −5° C. there was added 35 g. of stannous chloride in 90 ml. of concentrated hydrochloric acid and the mixture was allowed to stand with ice-bath cooling for 3 hours. The solid was collected, slurried in ethyl alcohol and filtered to give 11.9 g. of 4-benzyloxyphenylhydrazine hydrochloride; m.p. 185°–187° C. (aqueous ethyl alcohol).

EXAMPLE 6

3-(Dimethylamino)-6-hydroxy-1,2,3,4-tetrahydrocarbazole

The free base of Example 5, 6-(benzoyloxy)-3-(dimethylamino)-1,2,3,4-tetrahydrocarbazole (20 g.), was hydrogenated for one hour over palladium on charcoal. The catalyst was removed by filtration and the filtrate evaporated to give an off-white solid. Recrystallization from ethyl acetate gave 7.4 g. of 3-(dimethylamino)-6-hydroxy-1,2,3,4-tetrahydrocarbazole which melted at 202°–204° C. (corr.).

Test procedure 1a: active at 50 mg./kg.
Test procedure 1b: active at 30 mg./kg.
Test procedure 7: active at 4.8 ± 1.8 mg./kg.

EXAMPLE 7

3-(Dimethylamino)-8-methyl-1,2,3,4-tetrahydrocarbazole

Following the procedure give in Example 3 and using 10 g. of 4-dimethylaminocyclohexane and 11.2 g. of o-tolylhydrazine hydrochloride there was obtained 4.7 g. of 3-(dimethylamino)-8-methyl-1,2,3,4-tetrahydrocarbazole in the form of its hydrochloride which melted at 285°–287° C. (corr.).

Test procedure 7: active at 4.8 ± 1.4 mg./kg.

EXAMPLE 8

8-Chloro-3-(dimethylamino)-1,2,3,4-tetrahydrocarbazole

Following the procedure given in Example 3 and using 7.05 g. of 4-dimethylaminocyclohexanone and 8.95 g. of o-chlorophenylhydrazine hydrochloride therewas obtained 4.9 g. of 8-chloro-3-(dimethylamino)-1,2,3,4-tetrahydrocarbazole which melted at 154°–157° C. (corr.).

Test procedure 1b: active at 50 mg./kg.
Test procedure 5: active at 100 mg./kg. (IP)
Test procedure 7: active at 33.5 ± 6.5 mg./kg.

EXAMPLE 9

5,8-Dichloro-3-(dimethylamino)-1,2,3,4-tetrahydrocarbazole

Following the procedure given in Example 3 and using 7.05 g. of 4-dimethylaminocyclohexanone and 10.7 g. of 2,5-dichlorophenylhydrazine hydrochloride there was obtained 4.1 g. of 5,8-dichloro-3-(dimethylamino)-1,2,3,4-tetrahydrocarbazole which melted at 206°–209° C. (corr.).

Test procedure 1a: active at 30 mg./kg.
Test procedure 1b: active at 30 mg./kg.
Test procedure 4: active at 100 mg./kg. (IP)

EXAMPLE 10

3-(Dimethylamino)-6-nitro-1,2,3,4-tetrahydrocarbazole

Following the procedure given in Example 3 and using 10 g. of 4-dimethylaminocyclohexanone and 10.8 g. of p-nitro-phenylhydrazine hydrochloride there was obtained 2.2 g. of 3-(dimethylamino)-6-nitro-1,2,3,4-tetrahydrocarbazole which melted at 226°–229° C. (corr.).

Test procedure 3: active at 128 mg./kg.

EXAMPLE 11

9-(p-Chlorobenzyl)-3-(dimethylamino)-1,2,3,4-tetrahydrocarbazole

A mixture of 6.7 g. of 3-(dimethylamino)-1,2,3,4-tetrahydrocarbazole and 1.35 g. of sodium hydride in 75 ml. of dimethylformamide was heated on a steam bath and 5 g. of p-chlorobenzyl chloride in 10 ml. of dimethylformamide added dropwise. Heating was continued for two hours, after which the mixture was cooled and diluted with water. The oil which remained after decantation of the water was dissolved in hexane and chromatographed on an aluminum oxide column. Elution of the column with equal amounts of an ether-hexane mixture gave a solid which was collected by filtration. Recrystallization from an ether-hexane mixture gave 4.9 g. of 9-(p-chlorobenzyl)-3-(dimethylamino)-1,2,3,4-tetrahydrocarbazole which melted at 107°–108° C. (corr.).

Test procedure 3: active at 300 mg./kg.

Alterntively, 9-(p-chlorobenzyl)-3-(dimethylamino)-1,2,3,4-tetrahydrocarbazole can be prepared by following a procedure similar to that described in Example 18 below and using 3-(p-toluenesulfonyloxy)-9-(p-chlorobenzyl)-1,2,3,4-tetrahydrocarbazole and dimethylamine.

The 3-(p-toluenesulfonyloxy)-9-(p-chlorobenzyl)-1,2,3,4-tetrahydrocarbazole can be prepared from 3-hydroxy-9-(p-chlorobenzyl)-1,2,3,4-tetrahydrocarbazole and tosyl chloride by following a procedure similar to that described in Example 18.

The 3-hydroxy-9-(p-chlorobenzyl)-1,2,3,4-tetrahydrocarbazole, m.p. 85°–95° C., was prepared from the corresponding 3-benzoyloxy derivative by sodium hydroxide hydrolysis following the procedure described in Example 3. The crude product was purified by recrystallization from ethyl acetate-hexane followed by filtration through alumina ether and ether-ethyl acetate (1:1).

The 3-benzoyloxy-9-(p-chlorobenzyl)-1,2,3,4-tetrahydrocarbazole was prepared as follows:

A mixture of 29.1 g. of 3-benzoyloxy-1,2,3,4-tetrahydrocarbazole and 4.3 g. of sodium hydride (56% in mineral oil) in 200 ml. of dimethylformamide was heated on a steam ba th and 16.1 g. of p-chlorobenzyl chloride in 30 ml. of dimethylformamide was added dropwise. The reaction mixture was heated two hours, cooled, and diluted with water. The resulting oil was washed with water and crystallized from isopropyl alcohol to give 12.7 g. of 3-benzoyloxy-9-(p-chlorobenzyl)-1,2,3,4-tetrahydrocarbazole, m.p. 150°–152° C.

EXAMPLE 12

3-(Dimethylamino)-9-[2-(dimethylamino)ethyl]-1,2,3,4-tetrahydrocarbazole

Following the procedure given in Example 11 and using 6.7 g. of 3-(dimethylamino)-1,2,3,4-tetrahydrocarbazole, 1.35 g. of sodium hydride and 3.37 g. of dimethylaminoethyl chloride in 75 ml. of dimethylformamide there was obtained 5.6 g. of 3-(dimethylamino)-9-[2-(dimethylamino)ethyl]-1,2,3,4-tetrahydrocarbazole in the form of its dihydrochloride salt which melted at 269°–270° C. (dec.) (corr.).

Test procedure 3: active at 16 mg./kg. (SC)
Test procedure 7: active at 30 mg./kg.

Alternatively, 3-(dimethylamino)-9-[2-(dimethylamino)-ethyl]-1,2,3,4-tetrahydrocarbazole can be prepared by following a procedure similar to that described in Example 18 below and using 3-(p-toluenesulfonyloxy)-9-[2-(dimethylamino)ethyl]-1,2,3,4-tetrahydrocarbazole and dimethylamine.

The 3-(p-toluenesulfonyloxy)-9-[2-(dimethylamino)ethyl]-1,2,3,4-tetrahydrocarbazole can be prepared from 3-hydroxy-9-[2-(dimethylamino)ethyl]-1,2,3,4-tetrahydrocarbazole and tosyl chloride by following a procedure similar to that described in Example 18.

The 3-hydroxy-9-[2-(dimethylamino)ethyl]-1,2,3,4-tetrahydrocarbazole can be prepared from the corresponding 3-benzoyloxy derivative at potassium hydroxide hydrolysis following a procedure similar to that described in Example 3.

The 3-benzoyloxy-9-[2-(dimethylamino)ethyl]-1,2,3,4-tetrahydrocarbon was prepared by following an alkylation procedure similar to that described in Example 11 and using 13.1 g. of 3-benzoyloxy-1,2,3,4-tetrahydrocarbazole and 1.93 g. of sodium hydride (50% in mineral oil) in 150 ml. of dimethylformamide, and 4.9 g. of (dimethylamino)ethyl chloride in 10 ml. of benzene. An ethereal solution of the crude product was filtered through alumina and the concentrated ethereal eluate was treated with ethereal hydrogen chloride to give after recrystallization from isopropyl alcohol - ether 5.6 g. of 3-benzoyloxy-9-[2-(dimethylamino)ethyl]-1,2,3,4-tetrahydrocarbazole hydrochloride, m.p. 222°–225° C.

EXAMPLE 13

3-(Dimethylamino)-9-[2-(3,4,5-trimethoxybenzoyloxy)ethyl]-1,2,3,4-tetrahydrocarbazole Following the procedure given in Example 11 and using 6.7 g. of 3-(dimethylamino)-1,2,3,4-tetrahydrocarbazole, 1.35 g. of sodium hydride and 8.65 g. of 2-chloroethyl 3,4,5-trimethoxybenzoate there was obtained after recrystallization from an ethyl acetate-ether mixture 2.4 g. of 3-(dimethylamino)-9-[2-(3,4,5-trimethoxybenzoyloxy)ethyl]-1,2,3,4-tetrahydrocarbazole which melted at 127°–131° C. (corr.)

Test procedure 3: active at 300 mg./kg.

By heating a solution of 3-(dimethylamino)-9-[2-(3,4,5-trimethoxybenzoyloxy)ethyl]-1,2,3,4-tetrahydrocarbazole in aqueous ethyl alcohol with an excess of potassium hydroxide at 70° C. for one hour, there can be obtained, according to this invention, 3-(dimethylamino)-9-(2-hydroxyethyl)-1,2,3,4-tetrahydrocarbazole.

EXAMPLE 14

9-Carbethoxymethyl-3-(dimethylamino)-1,2,3,4-tetrahydrocarbazole

To a mixture of 6.7 g. of 3-(dimethylamino)-1,2,3,4-tetrahydrocarbazole and 1.35 g. of sodium hydride in 75 ml. of dimethylformamide was added 5.2 g. of ethyl bromoacetate and the mixture stirred and heated for one hour on a steam bath. The reaction mixture was cooled, diluted with water and extracted with ether. The ether extracts were dried, the ether evaporated and the residual oil treated with ethereal hydrochloric acid. The solid which precipitated was collected by filtration and recrystallized from isopropanol to give 2.9 g. of 9-carbethoxymethyl-3-(dimethylamino)-1,2,3,4-tetrahydrocarbazole in the form of its hydrochloride which melted at 242°–243° C. (corr.).

Test procedure 1a: active at 10 mg./kg.
Test procedure 3: active at 300 mg./kg.
Test procedure 7: active at 0.03 ± 0.003 mg./kg.

By heating a solution of 9-carbethoxymethyl-3-(dimethylamino)-1,2,3,4-tetrahydrocarbazole in aqueous ethyl alcohol with an excess of potassium hydroxide at 70° C. for one hour, there can be obtained, according to this invention, 9-carboxymethyl-3-(dimethylamino)-1,2,3,4-tetrahydrocarbazole.

EXAMPLE 15

3-(Dimethylamino)-9-ethyl-1,2,3,4-tetrahydrocarbazole

Following the procedure given in Example 11 and using 6.7 g. of 3-(dimethylamino)-1,2,3,4-tetrahydrocarbazole, 1.35 g. of sodium hydride and 5 g. of ethyl iodide there was obtained 7 g. of 3-(dimethylamino)-9-ethyl-1,2,3,4-tetrahydrocarbazole which was isolated in the form of its hydrochloride salt which melted at 292°–293° C. (dec.) (corr.).

Test procedure 1a: active at 30 mg./kg.
Test procedure 1b: active at 50 mg./kg.
Test procedure 7: active at 0.2 ± 0.03 mg./kg.

EXAMPLE 16

9-Allyl-3-(dimethylamino)-1,2,3,4-tetrahydrocarbazole

Following the procedure given in Example 11 and using 6.7 g. of 3-(dimethylamino)-1,2,3,4-tetrahydrocarbazole, 1.35 g. of sodium hydride and 4 g. of allyl bromide there was obtained 4 g. of 9-allyl-3-(dimethylamino)-1,2,3,4-tetrahydrocarbazole in the form of its hydrochloride salt which melted at 277°–279° C. (dec.) (corr.).

Test procedure 7: active at 0.1 ± 0.02 mg./kg.

EXAMPLE 17

3-(Dimethylamino)-9-[3-(dimethylamino)propyl]-1,2,3,4-tetrahydrocarbazole

Following the procedure given in Example 11 and using 6.7 g. of 3-(dimethylamino)-1,2,3,4-tetrahydrocarbazole, 1.35 g. of sodium hydride and 3.6 g. of 3-dimethylaminopropyl chloride there was obtained 8.5 g. of 3-(dimethylamino)-9-[3-(dimethylamino)propyl]-1,2,3,4-tetrahydrocarbazole in the form of its dihydrochloride salt which melted at 302°–305° C. (dec.) (corr.)

Test procedure 1a: active at 30 mg./kg.
Test procedure 1b: active at 30 mg./kg.
Test procedure 7: active at 30 mg./kg.

Alternatively, 3-(dimethylamino)-9-[3-(dimethylamino)-propyl]-1,2,3,4-tetrahydrocarbazole can be prepared by following a procedure similar to that described in Example 18 below and using 3-(p-toluenesulfonyloxy)-9-[3-(dimethylamino)propyl]-1,2,3,4-tetrahydrocarbazole and dimethylamine.

The 3-(p-toluenesulfonyloxy)-9-[3-(dimethylamino)-propyl]-1,2,3,4-tetrahydrocarbazole can be prepared from 3-hydroxy-9-[3-(dimethylamino)propyl]-1,2,3,4-tetrahydrocarbazole and tosyl chloride by following a procedure similar to that described in Example 18.

The 3-hydroxy-9-[3-(dimethylamino)propyl]-1,2,3,4-tetrahydrocarbazole was prepared from the corresponding 3-benzoyloxy derivative by sodium hydroxide hydrolysis by following a procedure similar to that described in Example 3. The free base was converted to the hydrochloride, m.p. 174°–176° C., on treatment in ether with ethereal hydrogen chloride and recrystallization from isopropyl alcohol.

The 3-benzoyloxy-9-[3-(dimethylamino)propyl]-1,2,3,4-tetrahydrocarbazole was prepared by following an alkylation procedure similar to that described in Example 11 and using 29.1 g. of 3-benzoyloxy-1,2,3,4-tetrahydrocarbazole and 4.3 g. of sodium hydride (50% in mineral oil) in 200 ml. of dimethylformamide, and 13 g. of 3-(dimethylamino)propyl chloride. The crude free base was extracted from the water diluted reaction mixture into ether and the ethereal solution was treated with ethereal hydrogen chloride. The resulting precipitate was recrystallized from isopropyl alcohol and ethyl acetate to give 6.2 g. of 3-benzoyloxy-1,2,3,4-tetrahydrocarbazole hydrochloride, m.p. 162°–180° C.

By following the alkylation procedure described in Example 11, substituting for p-chlorobenzyl chloride an equivalent amount of:
a. n-hexyl chloride
b. 2-phenylethyl chloride
c. 3,3-dimethylallyl bromide
d. 2-chloroethyl acetate
e. benzyl bromoacetate
f. 2-dimethylaminopropyl chloride
g. 2-(4-morpholinyl)-ethyl chloride
h. 2-(4-thiomorpholinyl)-ethyl chloride
i. 2-(1-piperidinyl)-ethyl chloride
j. 2-(1-pyrrolidinyl)-ethyl chloride
k. 2-(1-piperazinyl)-ethyl chloride
l. 2-(4-methyl-1-piperazinyl)-ethyl chloride
m. 2-(4-phenyl-1-piperazinyl)-ethyl chloride
n. 2,5-dimethoxy-4-nitrobenzyl chloride
o. 2,6-dichlorobenzyl bromide
p. 1-bromo-3-(3-methoxyphenyl)-propane
q. 2-hydroxy-5-nitrobenzyl bromide
r. 4-methylbenzyl chloride
s. 2,5-dimethylbenzyl chloride
t. 2-chloroethyl 3-(trifluoromethyl)-benzoate
u. 2-chloro-1-methylpropyl 2,3,4-trichlorobenzoate
v. 2-chloroethyl 4-nitrobenzoate
w. 2,6-dichlorobenzyl bromoacetate
x. 3,4,5-trimethoxybenzyl bromoacetate
there can be obtained respectively, according to this invention:
a. 3-(dimethylamino)-9-(n-hexyl)-1,2,3,4-tetrahydrocarbazole
b. 3-(dimethylamino)-9-(2-phenylethyl)-1,2,3,4-tetrahydrocarbazole
c. 3-(dimethylamino)-9-(3,3-dimethylallyl)-1,2,3,4-tetrahydrocarbazole
d. 3-(dimethylamino)-9-(2-acetoxyethyl)-1,2,3,4-tetrahydrocarbazole
e. 3-(dimethylamino)-9-(carbobenzoxymethyl)-1,2,3,4-tetrahydrocarbazole
f. 3-(dimethylamino)-9-(2-dimethylaminopropyl)-1,2,3,4-tetrahydrocarbazole
g. 3-(dimethylamino)-9-[2-(4-morpholinyl)-ethyl]-1,2,3,4-tetrahydrocarbazole
h. 3-(dimethylamino)-9-[2-(4-thiomorpholinyl)-ethyl]-1,2,3,4-tetrahydrocarbazole
i. 3-(dimethylamino)-9-[2-(1-piperidinyl)-ethyl]-1,2,3,4-tetrahydrocarbazole
j. 3-(dimethylamino)-9-[2-(1-pyrrolidinyl)-ethyl]-1,2,3,4-tetrahydrocarbazole
k. 3-(dimethylamino)-9-[2-(1-piperazinyl)-ethyl]-1,2,3,4-tetrahydrocarbazole
l. 3-(dimethylamino)-9-[2-(4-methyl-1-piperazinyl)-ethyl]-1,2,3,4-tetrahydrocarbazole
m. 3-(dimethylamino)-9-[2-(4-phenyl-1-piperazinyl)-ethyl]-1,2,3,4-tetrahydrocarbazole
n. 3-(dimethylamino)-9-(2,5-dimethoxy-4-nitrobenzyl)-1,2,3,4-tetrahydrocarbazole
o. 3-(dimethylamino)-9-(2,6-dichlorobenzyl)-1,2,3,4-tetrahydrocarbazole
p. 3-(dimethylamino)-9-[3-(3-methoxyphenyl)-1-propyl]-1,2,3,4-tetrahydrocarbazole
q. 3-(dimethylamino)-9-(2-hydroxy-5-nitrobenzyl)-1,2,3,4-tetrahydrocarbazole
r. 3-(dimethylamino)-9-(4-methylbenzyl)-1,2,3,4-tetrahydrocarbazole
s. 3-(dimethylamino)-9-(2,5-dimethylbenzyl)-1,2,3,4-tetrahydrocarbazole
t. 2-[3-(dimethylamino)-1,2,3,4-tetrahydrocarbazol-9-yl]-ethyl 3-(trifluoromethyl)-benzoate
u. 2-[3-(dimethylamino)-1,2,3,4-tetrahydrocarbazol-9-yl]-1,2-dimethylethyl 2,3,4-trichlorobenzoate
v. 2-[3-(dimethylamino)-1,2,3,4-tetrahydrocarbazol-9-yl]-ethyl 4-nitrobenzoate
w. 2,6-dichlorobenzyl 3-(dimethylamino)-1,2,3,4-tetrahydrocarbazole-9-acetate
x. 3,4,5-trimethoxybenzyl 3-(dimethylamino)-1,2,3,4-tetrahydrocarbazole-9-acetate The halo starting materials (t), (u), (v), (w), and (x), disclosed above, can be prepared readily by conventional processes, for example, by the reaction of the appropriate alcohols with the appropriate acid halides in the presence of a base.

EXAMPLE 18

3-(Butylamino)-1,2,3,4-tetrahydrocarbazole

A mixture of 25 g. of 3-(p-toluenesulfonyloxy)-1,2,3,4-tetrahydrocarbazole (hereinafter 3-tosyloxy-1,2,3,4-tetrahydrocarbazole) and 125 ml. of n-butylamine was heated in an autoclave at a temperature ranging between 120°–140° C. for twenty hours. The excess amine was removed by distillation in vacuo, the residue made basic with sodium hydroxide solution, and the mixture extracted with ether. The ether extracts were dried and the ether evaporated to give an oil which crystallized upon standing. The crystals were collected by filtration and recrystallized from an ether-pentane mixture. There was thus obtained 8 g. of 3-(butylamino)-1,2,3,4-tetrahydrocarbazole which melted at 110°–111° C. (corr.).

The 3-tosyloxy-1,2,3,4-tetrahydrocarbazole was prepared by warming a mixture of 152 g. of 3-hydroxy-1,2,3,4-tetrahydrocarbazole and 171 g. of tosyl chloride in 410 ml. of pyridine. The solid which separated was collected by filtration, slurried in isopropanol and filtered to give 247 g. of b 3-tosyloxy-1,2,3,4-tetrahydrocarbazole which melted at 148°–151° C.

Test procedure 1b: active at 10 mg./kg.

EXAMPLE 19

3-(Benzylamino)-1,2,3,4-tetrahydrocarbazole

Following the procedure given in Example 18 and using 25 g. of 3-tosyloxy-1,2,3,4-tetrahydrocarbazole and 125 ml. of benzylamine there was obtained 9.4 g. of 3(benzylamino)- 1,2,3,4-tetrahydrocarbazole which melted at 109°–115° C. (corr.).

Test procedure 2: decrease in viciousness and aggressiveness in monkeys at 4 mg./kg.
Test procedure 3: active at 300 mg./kg.

EXAMPLE 20

3-(Propylamino)-1,2,3,4-tetrahydrocarbazole

Following the procedure given in Example18 and using 34 g. of 3-tosyloxy-1,2,3,4-tetrahydrocarbazole and 200 ml. of propylamine there was obtained 9.8 g. of 3-(propylamino)-1,2,3,4-tetrahydrocarbazole which melted at 124°–125° C. (corr.).

EXAMPLE 21

3-(Dimethylamino)-6-methyl-1,2,3,4-tetrahydrocarbazole

Following the procedure given in Example 18 and using 35.5 g. of 6-methyl-3-tosyloxy-1,2,3,4-tetrahydrocarbazole and 200 ml. of dimethylamine there was obtained 1.6 g. of 3-(dimethylamino)-6-methyl-1,2,3,4-tetrahydrocarbazole which melted at 116°–118° C. (corr.).

Test procedure 7: active at 18.5 ± 4.7 mg./kg.

The intermediate 6-methyl-3-tosyloxy-1,2,3,4-tetrahydrocarbazole was prepared from 63.3 g. of 3-hydroxy-6-methyl-1,2,3,4-tetrahydrocarbazole and 66.4 g. of tosyl chloride using the procedure described in Example 18 for the preparation of 3-tosyloxy-1,2,3,4-tetrahydrocarbazole. There was thus obtained 59.7 g. of 6-methyl-3-tosyloxy-1,2,3,4-tetrahydrocarbazole which melted at 125°–127° C.

The 3-hydroxy-6-methyl-1,2,3,4-tetrahydrocarbazole used above was prepared by hydrolysis of 99.4 g. of 3-benzoyloxy-6-methyl-1,2,3,4-tetrahydrocarbazole with 21 g. of potassium hydroxide in 300 ml. of water. The hydrolysis was carried out by refluxing the reaction mixture for 2 hours and collecting the resultant solid by filtration. There was thus obtained 63 g. of 3-hydroxy-6-methyl-1,2,3,4-tetrahydrocarbazole.

The 3-benzoyloxy-6-methyl-1,2,3,4-tetrahydrocarbazole used above was prepared by refluxing 218 g. of 4-benzoyloxycyclohexanone and 110 g. of p-tolylhydrazine in 800 ml. of acetic acid. The solid 3-benzoyloxy-6-methyl-1,2,3,4-tetrahydrocabazole which separated was collected by filtration and dried to give 239 g. which melted at 192°–195° C.

EXAMPLE 22

3-(4-Phenyl-1-piperazinyl)-1,2,3,4-tetrahydrocarbazole

Folllowing the procedure given in Example 18 and using 5.7 g. of 3-tosyloxy-1,2,3,4-tetrahydrocarbazole and 2.5 g. of 4-phenylpiperazine there was obtained 3-(4-phenyl-1-piperazinyl)-1,2,3,4-tetrahydrocarbazole which melted at 230°–232° C. (corr.).

Test procedure 3: active at 300 mg./kg.
Test procedure 4: active at 100 mg./kg. (IP)
Test procedure 6: active at 100 mg./kg.

EXAMPLE 23

3-(Methylamino)-1,2,3,4-tetrahydrocarbazole

A mixture of 17 g. of 3-tosyloxy-1,2,3,4-tetrahydrocarbazole and 25 g. of 40% methylamine in 200 ml. of 2-ethoxyethanol containing 5 g. of sodium bicarbonate was heated on a steam bath for 1 hour then left standing overnight at room temperature. The solvent was removed by distillation and the residue taken up in ether and the mixture filtered. Evaporation of the filtrate gave a residue which crystallized upon trituration with ether. The 3-(methylamino)-1,2,3,4-tetrahydrocarbazole thus obtained melted at 134°–136° C. (corr.).

Test Procedure 1a: active at 30 mg./kg.
Test procedure 1b: active at 10 mg./kg.
Test procedure 2: taming in monkeys at 4 mg./kg.
Test procedure 7: active at 5.2 ± 0.1 mg./kg.

EXAMPLE 24

3-(Ethylamino)-1,2,3,4-tetrahydrocarbazole

Following the procedure given in Example 18 and using 25g. of 3-tosyloxy-1,2,3,4-tetrahydrocarbazole and 90 g. of ethylamine there was obtained 3 g. of 3-(ethylamino)-1,2,3,4-tetrahydrocarbazole which melted at 128°–129° C. (corr.). Alternatively this compound can be prepared by reduction of 3-acetamido-1,2,3,4-tetrahydrocarbazole (Example 2) with lithium aluminum hydride following a procedure similar to that described in Example 260 below.

Test procedure 2: taming in monkeys at 4 mg./kg.
Test procedure 5: active at 100 mg./kg. (PO)
Test procedure 6: active at 40 mg./kg.

EXAMPLE 25

3-(1-Piperidyl)-1,2,3,4-tetrahydrocarbazole

Following the procedure given in Example 18 and using 25 g. of 3-tosyloxy-1,2,3,4-tetrahydrocarbazole and 100 g. of piperidine there was obtained 6.2 g. of 3-(1-piperidyl)-1,2,3,4-tetrahydrocarbazole which melted at 77°–115° C. (corr.).

Test procedure 3: 1 active at 64 mg./kg.
Test procedure 4: active at 100 mg./kg. (IP)
Test procedure 5: active at 100 mg./kg. (IP)
Test procedure 6: active at 100 mg./kg.
Test procedure 7: active at 3.1 ± 0.7 mg./kg.

EXAMPLE 26

3-(4-Morpholinyl)-1,2,3,4-tetrahydrocarbazole

Following the procedure given in Example 18 and using 34 g. of 3-tosyloxy-1,2,3,4-tetrahydrocarbazole and 200 g. of morpholine there was obtained 13 g. of 3-(4-morpholinyl)-1,2,3,4-tetrahydrocarbazole which melted at 131°–134° C. (corr.).

Test procedure 3: active at 64 mg./kg.
Test procedure 4: active at 100 mg./kg. (PO)
Test procedure 5: active at 100 mg./kg. (IP)
Test procedure 6: active at 39 mg./kg.

EXAMPLE 27

3-(1-Pyrrolidinyl)-1,2,3,4-tetrahydrocarbazole

Following the procedure given in Example 18 and using 34 g. of 3-tosyloxy-1,2,3,4-tetrahydrocarbazole and 99 g. of pyrrolidine there was obtained 13 g. of 3-(1-pyrrolidinyl)-1,2,3,4-tetrahydrocarbazole which melted at 200°-205° C. (corr.).

Test procedure 3: active at 300 mg./kg.
Test procedure 7: active at 0.4 ± 0.1 mg./kg.

EXAMPLE 28

6-Chloro-3-(dimethylamino)-1,2,3,4-tetrahydrocarbazole

Following the procedure given in Example 18 and using 38 g. of 6-chloro-3-tosyloxy-1,2,3,4-tetrahydrocarbazole and 250 ml. of dimethylamine there was obtained 8.6 g. of 6-chloro-3-(dimethylamino)-1,2,3,4-tetrahydrocarbazole which melted at 181°-184° C. (corr.).

Test procedure 1a: active at 1 mg./kg.

The 6-chloro-3-tosyloxy-1,2,3,4-tetrahydrocarbazole used above was prepared from 67.7 g. of 6-chloro-3-hydroxy-1,2,3,4-tetrahydrocarbazole and 59 g. of p-tosyl chloride following the procedure described in Example 18. There was thus obtained 101 g. of 6-chloro-3-tosyloxy-1,2,3,4-tetrahydrocarbazole.

The 6-chloro-3-hydroxy-1,2,3,4-tetrahydrocarbazole used above was prepared by hydrolysis of 24.2 g. of 3-benzoyloxy-6-chloro-1,2,3,4-tetrahydrocarbazole with 5 g. of potassium hydroxide in 50 ml. of water using the procedure given in Example 21 for the preparation of the corresponding 6-methyl compound. There was thus obtained 15.4 g. of 6-chloro-3-hydroxy-1,2,3,4-tetrahydrocarbazole which melted at 131°-133° C.

The 3-benzoyloxy-6-chloro-1,2,3,4-tetrahydrocarbazole used above was prepared by the reaction of 14.3 g. of p-chlorophenylhydrazine and 21 g. of 4-benzoyloxycyclohexanone using the procedure described in Example 21 for the preparation of the corresponding 6-methyl compound. There was thus obtained 18 g. of 3-benzoyloxy-6-chloro-1,2,3,4-tetrahydrocarbazole which melted at 158°-160° C.

EXAMPLE 29

3-(Dimethylamino)-9-methyl-1,2,3,4-tetrahydrocarbazole

Following the procedure described in Example 18 and using 36.2 g. of 9-methyl-3-tosyloxy-1,2,3,4-tetrahydrocarbazole and 250 ml. of dimethylamine there was obtained 9.5 g. of 3-(dimethylamino)-9-methyl-1,2,3,4-tetrahydrocarbazole in the form of its hydrochloride salt and which melted at >300° C.

Test procedure 1a: active at 10 mg./kg.
Test procedure 1b: active at 10 mg./kg.
Test procedure 7: active at 0.6 ± 0.1 mg./kg.

The 9-methyl-3-tosyloxy-1,2,3,4-tetrahydrocarbazole was prepared from 49 g. of 3-hydroxy-9-methyl-1,2,3,4-tetrahydrocarbazole and 49 g. of tosyl chloride using the procedure described in Example 21 for the preparation of 6-methyl-3-tosyloxy-1,2,3,4-tetrahydrocarbazole. There was thus obtained 81 g. of 9-methyl-3-tosyloxy-1,2,3,4-tetrahydrocarbazole which melted at 155°-157° C.

The 3-hydroxy-9-methyl-1,2,3,4-tetrahydrocarbazole was prepared by hydrolysis of 9.1 g. of 3-benzoyloxy-9-methyl-1,2,3,4-tetrahydrocarbazole and 1.95 g. of potassium hydroxide in 100 ml. of 50% ethanol using the procedure described in Example 21 for the preparation of 3-hydroxy-6-methyl-1,2,3,4-tetrahydrocarbazole. There was thus obtained 48 g. of 3-hydroxy-9-methyl-1,2,3,4-tetrahydrocarbazole which melted at 104°-106° C.

The 3-benzoyloxy-9-methyl-1,2,3,4-tetrahydrocarbazole was prepared by the reaction of 34.8 g. of 1-phenyl-1-methylhydrazine and 62 g. of 4-benzoyloxycyclohexanone using the procedure described in Example 21 for the preparation of 3-benzoyloxy-6-methyl-1,2,3,4-tetrahydrocarbazole. There was thus obtained 71 g. of 3-benzoyloxy-9-methyl-1,2,3,4-tetrahydrocarbazole which melted at 93°-96° C.

EXAMPLE 30

9-Benzyl-3-(dimethylamino)-1,2,3,4-tetrahydrocarbazole

Following the procedure given in Example 18 and using 25 g. of 9-benzyl-3-tosyloxy-1,2,3,4-tetrahydrocarbazole and 50 ml. of dimethylamine there was obtained 3.2 g. of 9-benzyl-3-(dimethylamino)-1,2,3,4-tetrahydrocarbazole which melted at 81°-83° C. (corr.).

Test procedure 3: active at 32 mg./kg.
Test procedure 7: active at 0.5 ± 0.1 mg./kg.

The 9-benzyl-3-tosyloxy-1,2,3,4-tetrahydrocarbazole, melting point 150°-152° C., was prepared by tosylation of 32 g. of 9-benzyl-3-hydroxy-1,2,3,4-tetrahydrocarbazole, melting point 105°-111° C., which was prepared by hydrolysis of 61 g. of 9-benzyl-3-benzoyloxy-1,2,3,4-tetrahydrocarbazole. The latter, melting point 125°-127° C., was prepared from 23.4 g. of phenylbenzylhydrazine and 2 g. of 4-benzoyloxycyclohexanone.

EXAMPLE 31

3-[2-(Diethylamino)ethylamino]-1,2,3,4-tetrahydrocarbazole

Following the procedure given in Example 18 and using 34 g. of 3-tosyloxy-1,2,3,4-tetrahydrocarbazole and 200 ml. of 3-diethylaminoethylamine there was obtained 11.4 g. of 3-[2-(diethylamino)ethylamino]-1,2,3,4-tetrahydrocarbazole which melted at 106°-107° C. (corr.).

Test procedure 1a: active at 50 mg./kg.
Test procedure 3: active at 32 mg./kg.

By following the procedure described in Example 18, substituting for n-butylamine an equivalent amount of:
a. n-hexylamine
b. 3-phenylpropylamine
c. di-n-hexylamine
d. N-methyl-n-hexylamine
e. dibenzylamine
f. N-benzyl-N-methylamine
g. thiomorpholine
h. piperazine
i. N-methylpiperazine
j. 4-dimethylaminobutylamine
k. 3-dimethylaminobutylamine
l. 2-(4-morpholinyl)-ethylamine
m. 2-(4-thiomorpholinyl)-ethylamine
n. 2-(1-piperidinyl)-ethylamine
o. 2-(1-pyrrolidnyl)-ethylamine
p. 2-(1-piperazinyl)-ethylamine
q. 2-(4-methyl-1-piperazinyl)-ethylamine
r. 2-(4-phenyl-1-piperazinyl)-ethylamine
s. 2-[4-(2,6-dimethylphenyl)-1-piperazinyl]-ethylamine
t. 2-[4-(3-chloro-4-methylphenyl)-1-piperazinyl]-ethylamine
u. 2-[4-(2-methoxy-5-chlorophenyl)-1-piperazinyl]-ethylamine
v. 2-[4-(4-methylthiophenyl)-1-piperazinyl]-ethylamine w. 2-[4-(2-lbutoxyphenyl)-1-piperazinlyl]-ethylamine there can be obtained respectively, according to this invention:

a. 3-(n-hexylamino)-1,2,3,4-tetrahydrocarbazole
b. 3-(3-phenylpropylamino)-1,2,3,4-tetrahydrocarbazole
c. 3-(di-n-hexylamino)-1,2,3,4-tetrahydrocarbazole
d. 3-(N-methyl-n-hexylamino)-1,2,3,4-tetrahydrocarbazole
e. 3-(dibenzylamino)-1,2,3,4-tetrahydrocarbazole
f. 3-(N-benzyl-N-methylamino)-1,2,3,4-tetrahydrocarbazole
g. 3-(4-thiomorpholinyl)-1,2,3,4-tetrahydrocarbazole
h. 3-(1-piperazinyl)-1,2,3,4-tetrahydrocarbazole
i. 3-(4-methyl-1-piperazinyl)-1,2,3,4-tetrahydrocarbazole
j. 3-(4-dimethylaminobutylamino)-1,2,3,4-tetrahydrocarbazole
k. 3-(3-dimethylaminobutylamino)-1,2,3,4-tetrahydrocarbazole
l. 3-[2-(4-morpholinyl)-ethylamino]-1,2,3,4-tetrahydrocarbazole
m. 3-[2-(4-thiomorpholinyl)-ethylamino]-1,2,3,4-tetrahydrocarbazole
n. 3-[2-(1-piperidinyl)-ethylamino[-1,2,3,4-tetrahydrocarbazole
o. 3-[2-(1-pyrrolidinyl)-ethylamino]-1,2,3,4-tetrahydrocarbazole
p. 3-[2-(1-piperazinyl)-ethylamino]-1,2,3,4-tetrahydrocarbazole
q. 3-[2-(4-methyl-1-methyl-1-piperazinyl)-ethylamino]-1,2,3,4-tetrahydrocarbazole
r. 3-[2-(4-phenyl-1-piperazinyl)-ethylamino]-1,2,3,4-tetrahydrocarbazole
s. 3-{2-[4-(2,6-dimethylphenyl)-1-piperazinyl]-ethylamino}-1,2,3,4-tetrahydrocarbazole
t. 3-{2-[4-(3-chloro-4-methylphenyl)-1-piperazinyl]-ethylamino}-1,2,3,4-tetrahydrocarbazole
u. 3-{2-[4-(2-methoxy-5-chlorophenyl)-1-piperazinyl]-ethylamino}-1,2,3,4-tetrahydrocarbazole
v. 3-{2-[4-(4-methylthiophenyl)-1-piperazinyl]-ethylamino}-1,2,3,4-tetrahydrocarbazole
w. 3-{2-[4-(2-butoxyphenyl)-1-piperazinyl]-ethylamino}-1,2,3,4-tetrahydrocarbazole

EXAMPLE 32

3-(Dimethylamino)-6-ethoxy-1,2,3,4-tetrahydrocarbazole can be prepared by following the procedure described in Example 18 but substituting for the tetrahydrocarbazole and n-butylamine used therein an equivalent amount of 3-(p-toluenesulfonyloxy)-6-ethoxy-1,2,3,4-tetrahydrocarbazole and dimethylamine respectively.

The 3-(p-toluenesulfonyloxy)-6-ethoxy-1,2,3,4-tetrahydrocarbazole can be prepared from the corresponding 3-hydroxy derivative and tosyl chloride by following a procedure similar tto that described in Example 18.

The 3-hydroxy-6-ethoxy-1,2,3,4-tetrahydrocarbazole, m.p. 111°-116° C., was obtained from the corresponding 3-benzoyloxy derivative by sodium hydroxide hydrolysis by following a procedure similar to that described in Example 3. The product was crystallized from isopropyl alcohol-heptane.

The 3-benzoyloxy-6-ethoxy-1,2,3,4-tetrahydrocarbazole, m.p. 132°-135° C., was prepared from 60.2 g. of 4-ethoxyphenylhydrazine hydrochloride and 69.7 g. of 4-benzyloxycyclohexanone by following a procedure similar to that described in Example 3.

EXAMPLE 33

3-(Dimethylamino)-6,7-dimethoxy-9-carboxymethyl-1,2,3,4-tetrahydrocarbazole can be prepared by following the procedure described in Example 18 but substituting for the tetrahydrocarbazole and n-butylamine used therein an equivalent amount of 3-(p-toluenesulfonyloxy)-6,7-dimethoxy-9-carboxymethyl-1,2,3,4-tetrahydrocarbazole and dimethylamine respectively.

The 3-(p-toluenesulfonyloxy)-6,7-dimethoxy-9-carboxymethyl-1,2,3,4-tetrahydrocarbazole can be prepared from the corresponding 3-hydroxy derivative and a mole equivalent of tosyl chloride by following a procedure similar to that in Example 18.

The 3-hydroxy-6,7-dimethoxy-9-carboxymethyl-1,2,3,4-tetrahydrocarbazole can be prepared from 3-benzoyloxy-6,7-dimethoxy-9-carbethoxymethyl-1,2,3,4-tetrahydrocarbazole by hydrolysis with at least a two mole equivalent of potassium hydroxide following a procedure similar to that described in Example 3.

The 3-benzoyloxy-6,7-dimethoxy-9-carbethoxymethyl-1,2,3,4-tetrahydrocarbazole was prepared by following an alkylation procedure similar to that described in Example 11 but using 17.6 g. of 3-benzoyloxy-6,7-dimethoxy-1,2,3,4-tetrahydrocarbazole (see Example 4) and 2.14 g. of sodium hydride (56% in mineral oil) in 200 ml. of dimethylformamide, and 8.4 g. of ethyl bromoacetate. The crude product in ethyl acetate was filtered through alumina, the filtrate was evaporated to dryness under reduced pressure and the residue was recrystalized from ethyl acetate to give 3-benzoyloxy-6,7-dimethoxy-9-carbethoxymethyl-1,2,3,4-tetrahydrocarbazole, m.p. 125°-127° C.

EXAMPLE 34

3-(Dimethylamino)-6-fluoro-1,2,3,4-tetrahydrocarbazole

Following the procedure given in Example 3 and using 8.7 g. of 4-dimethylaminocyclohexanone and 10 g. of 4-fluorophenylhydrazine hydrochloride there was obtained 3-(dimethylamino)-6-fluoro-1,2,3,4-tetrahydrocarbazole which on treatment in ether with ethereal hydrogen chloride yielded 10.9 g. of the corresponding hydrochloride salt, m.p. 264°-268° C.

EXAMPLE 35

3-(Dimethylamino)-6,8-dimethyl-1,2,3,4-tetrahydrocarbazole

Following the procedure given in Example 3 and using 9 g. of 4-dimethylaminocyclohexanone and 11 g. of 2,4-dimethylphenylhydrazine hydrochloride there was obtained, after treatment of the free base in ether with ethereal hydrogen chloride, 10.9 g. of 3-(dimethylamino)-6,8-1,2,3,4-tetrahydrocarbazole hydrochloride; m.p. 312°-315° C.

EXAMPLE 36

3-(Dimethylamino)-8-ethyl-1,2,3,4-tetrahydrocarbazole

Following the procedure given in Example 3 and using 9 g. of 4-dimethylaminocyclohexanone and 11 g. of 2-ethylphenylhydrazine hydrochloride there was obtained, after treatment of the free base in ether with ethereal hydrogen chloride, 6.7 g. of 3-(dimethylamino)-8-ethyl-1,2,3,4-tetrahydrocarbazole hydrochloride, m.p. 282°–285° C.

EXAMPLE 37

3-(Dimethylamino)-8-fluoro-1,2,3,4-tetrahydrocarbazole

Following the procedure given in Example 3 and using 7.8 g. of 4-dimethylaminocyclohexanone and 9 g. of 2-fluorophenylhydrazine hydrochloride there was obtained, after treatment of the free base in ether with ethereal hydrogen chloride, 6.5 g. of 3-(dimethylamino)-8-fluoro-1,2,3,4-tetrahydrocarbazole hydrochloride, m.p. 298°–302° C.

EXAMPLE 38

3-(Dimethylamino)-6-amino-1,2,3,4-tetrahydrocarbazole is prepared by dissolving 0.1 mole of 3-(dimethylamino)-6-nitro1,2,3,4-tetrahydrocarbazole (Example 10) in 400 ml. absolute ethyl alcohol and hydrogenating over Raney nickel at about 350 psig and at room temperature until the required amount of hydrogen has reacted. The resulting 3-(dimethylamino)-6-amino-1,2,3,4-tetrahydrocarbazole can be isolated and purified using conventional procedures.

EXAMPLE 39

3-(Dimethylamino)-8-carboxy-1,2,3,4-tetrahydrocarbazole

A solution of 14.1 g. of 4-dimethylaminocyclohexanone and 18.9 g. of 2-carboxyphenylhydrazine hydrochloride in 150 ml. of absolute ethyl alcohol was heated under reflux for six hours, cooled, and the resulting crystalline 4-dimethylaminocyclohexanone 2-carboxyphenylhydrazone hydrochloride was collected by filtration, washed with isopropyl alcohol and ether, suspended in 200 ml. of 2% hydrogen chloride in acetic acid and heated at reflux for eight hours. The mixture was cooled and the solids were collected by filtration, washed with isopropyl alcohol and dissolved in 400 ml. of water. The aqueous solution was treated with alkali until neutral and allowed to stand for two hours. The resulting crystals were filtered to give, on recrystallization from water, 30.3 g. of 3-(dimethylamino)-8-carboxy-1,2,3,4-tetrahydrocarbazole hydrate, m.p. > 300° C. (dec.)

EXAMPLE 40

3-(Dimethylamino)-6-carboxy-1,2,3,4-tetrahydrocarbazole

Following a procedure similar to that described in Example 39 and using 14.1 g. of 4-dimethylaminocyclohexanone, 18.9 g. of 4-carboxyphenylhydrazine hydrochloride and 150 ml. of absolute ethyl alcohol there was obtained, after recrystallization from water, 20 g. of 4-[4-(dimethylamino)-cyclohexylidenehydrazino]benzoic acid hydrochloride (4-dimethylaminocyclohexanone 4-carboxyphenylhydrazone hydrochloride), m.p. 252°–254° C. Following a procedure similar to that described in Example 39 and using 24.7 g. of 4-dimethylaminocyclohexanone 4-carboxyphenylhydrazone hydrochloride in 250 ml. of 2% hydrogen chloride in acetic acid there was obtained 9.2 g. of 3-(dimethylamino)-6-carboxy-1,2,3,4-tetrahydrocarbazole, m.p. 315° C. (dec.).

Following a procedure similar to that described in Example 39 but substituting for 2-carboxyphenylhydrazine hydrochloride an equivalent amount of 3-carboxyphenylhydrazine hydrochloride there is obtained a mixture of 41. 3-(Dimethylamino)-5-carboxy-1,2,3,4-tetrahydrocarbazole and
42. 3-(Dimethylamino)-7-carboxy-1,2,3,4-tetrahydrocarbazole which are separated and purified by standard recrystallization procedures.

EXAMPLE 43

3-(Dimethylamino)-6-ethoxycarbonyl-1,2,3,4-tetrahydrocarbazole

A solution of 15.5 g. of 4-dimethylaminocyclohexanone and 15.2 g. of 4-carboxyphenylhydrazine in 200 ml. of 5-N hydrogen chloride in ethyl alcohol was refluxed for twentyfour hours and the reaction mixture was evaporated to dryness under reduced pressure. The residue was dissolved in water, the aqueous solution was made alkaline with dilute sodium hydroxide and extracted with methylene dichloride and the extract was evaporated to dryness under reduced pressure to give, after recrystallization from isopropyl alcohol, 17.8 g. of 3-(dimethylamino)-6-ethoxycarbonyl-1,2,3,4-tetrahydrocarbazole, m.p. 188°–190° C.

EXAMPLE 44

3-(Dimethylamino)-8-ethoxycarbonyl-1,2,3,4-tetrahydrocarbazole

A solution of 4.5 g. of 3-(dimethylamino)-8-carboxy1,2,3,4-tetrahydrocarbazole (Example 39) in 150 ml. of 5-N hydrogen chloride in ethyl alcohol was heated under reflux for thirty hours. The solution was evaporated to dryness under reduced pressure and the residue was recrystallized from ethanol to give 3 g. of 3-(dimethylamino)-8-ethoxycarbonyl-1,2,3,4-tetrahydrocarbazole hydrochloride, m.p. 263°–264° C.

EXAMPLE 45

A.
3-(Dimethylamino)-5-ethoxycarbonyl-1,2,3,4-tetrahydrocarbazole and (B)
3-(Dimethylamino)-7-ethoxycarbonyl-1,2,3,4-tetrahydrocarbazole Following a procedure similar to that described in Example 43 and using 15.5 g. of 4-dimethylaminocyclohexanone and 13.2 g. of 3-carboxyphenylhydrazine in 200 ml. of 5-N hydrogen chloride in ethyl alcohol there was obtained, on evaporation to dryness of the methylene dichloride extract, a crude mixture which was dissolved in ether and treated with ethereal hydrogen chloride. Isopropyl alcohol was added to the mixture and the ether was evaporated to give a clear solution which on refrigeration and filtration gave 9.8 g. of 3-(dimethylamino)-7-ethoxycarbonyl-1,2,3,4-tetrahydrocarbazole hydrochloride, m.p. 243°–245° C. This salt was treated with dilute sodium hydroxide and the resulting free base was extracted into methylene dichloride, dried, and evaporated to dryness to give 8.1 g. of 3-(dimethylamino)-7-ethoxycarbonyl-1,2,3,4-tetrahydrocarbazole, m.p. 144°–146° C. The isopropyl alcohol filtrate from above was concentrated under reduced pressure, cooled and filtered, and the filtrate was filtered again to yield a total of 12.8 g. of crystals which were recrystallized from ethyl alcohol and then from water to give a solid, m.p. 221°–223° C. A solution of this solid in water was made alkaline with dilute sodium hydroxide and extracted with methylene dichloride, dried, and evaporated to dryness under reduced pressure to give 8.9 g. of 3-(dimethylamino)-5-ethoxycarbonyl-1,2,3,4-tetrahydrocarbazole, m.p. 114°–116° C.

Other compounds which are encompassed by this invention and which are prepared by the conventional procedures described hereinbefore are listed below:

By reaction of the carboxylic acid chlorides, prepared by conventional procedures (see Example 250 below) from the appropriate compounds of Examples 39 to 42 above, with the appropriate alcohols there are obtained:

46. 3-(Dimethylamino)-8-benzyloxycarbonyl-1,2,3,4-tetrahydrocarbazole
47. 3-(Dimethylamino)-5-hexyloxycarbonyl-1,2,3,4-tetrahydrocarbazole
48. 3-(Dimethylamino)-6-isopropyloxycarbonyl-1,2,3,4-tetrahydrocarbazole
49. 3-(Dimethylamino)-6-(4-trifluoromethylbenzyloxy)carbonyl1,2,3,4-tetrahydrocarbazole
50. 3-(Dimethylamino)-8-(4-nitrobenzyloxy)carbonyl-1,2,3,4-tetrahydrocarbazole
51. 3-(Dimethylamino)-8-(4-fluorobenzyloxy)carbonyl-1,2,3,4-tetrahydrocarbazole
52. 3-(Dimethylamino)-8-(3,4,5-trimethoxybenzyloxy)carbonyl-1,2,3,4-tetrahydrocarbazole
53. 3-(Dimethylamino)-7-(4-methylbenzyloxy)carbonyl-1,2,3,4-tetrahydrocarbazole
54. 3-(Dimethylamino)-8-(2-chloro-4-methoxybenzyloxy)carbonyl-1,2,3,4-tetrahydrocarbazole.

EXAMPLE 55

3-(Dimethylamino)-6-hydroxymethyl-1,2,3,4-tetrahydrocarbazole

A solution of 12.8 g. of 3-(dimethylamino)-6-ethoxycarbonyl-1,2,3,4-tetrahydrocarbazole (Example 43) in 350 ml. of dry tetrahydrofuran was added dropwise to a refluxing solution of 3.5 g. of lithium aluminum hydride in 100 ml. of dry tetrahydrofuran and refluxing was continued for one hour after completion of the addition. Ethyl acetate was added followed by water, the mixture was filtered, and the filtrate was evaporated to dryness to give, after recrystallization from ethyl alcohol, 6.4 g. of 3-(dimethylamino)-6-hydroxymethyl1,2,3,4-tetrahydrocarbazole, m.p. 195°–197° C.

EXAMPLE 56

3-(Dimethylamino)-8-hydroxymethyl-1,2,3,4-tetrahydrocarbazole

Following a procedure similar to that described in Example 55 and using 2.4 g. of 3-(dimethylamino)-8-ethoxycarbonyl-1,2,3,4-tetrahydrocarbazole (Example 44), 1.6 g. of lithium aluminum hydride and 150 ml. of dry tetrahydrofuran there was obtained, after successive recrystallizations from isopropyl alcohol and ethyl alcohol, 0.56 g. of 3-(dimethylamino)-8-hydroxymethyl-1,2,3,4-tetrahydrocarbazole, m.p. 227°–230° C.

EXAMPLE 57

3-(Dimethylamino)-5-hydroxymethyl-1,2,3,4-tetrahydrocarbazole

A solution of 3.4 g. of 3-(dimethylamino)-5-ethoxycarbonyl-1,2,3,4-tetrahydrocarbazole (Example 45A) in 40 ml. of benzene was added to 114 ml. of a refluxing solution of sodium bis(2-methoxyethoxy)aluminum hydride, prepared by diluting 14 ml. of a 70% benzene solution of sodium bis(2methoxyethoxy) aluminum hydride with 100 ml. of benzene, and refluxing was continued for three hours. The reaction mixture was cooled, water was added and the resulting white solid was collected by filtration and slurried in water. The slurry was adjusted to pH 4 by addition of 1-N sulfuric acid and filtered. The filtrate was made alkaline with dilute sodium hydroxide and the resulting solid was collected by filtration to give, after crystallization from ethyl alcohol, 2.26 g. of 3-(dimethylamino)5-hydroxymethyl-1,2,3,4-tetrahydrocarbazole, m.p. 245°–248° C.

By conventional esterification procedures using the appropriate carboxylic acid chlorides and hydroxymethyl compounds of Examples 55 and 56 above there are obtained:

58. 3-(Dimethylamino)-6-acetoxymethyl-1,2,3,4-tetrahydrocarbazole
59. 3-(Dimethylamino)-8-hexanoyloxymethyl-1,2,3,4-tetrahydrocarbazole
60. 3-(Dimethylamino)-8-benzoyloxymethyl-1,2,3,4-tetrahydrocarbazole
61. 3-(Dimethylamino)-6-isopropanoyloxymethyl-1,2,3,4-tetrahydrocarbazole
62. 3-(Dimethylamino)-8-(4-trifluoromethylbenzoyloxy)methyl-1,2,3,4-tetrahydrocarbazole
63. 3-(Dimethylamino)-6-(3,4,5-trimethoxybenzoyloxy)methyl-1,2,3,4-tetrahydrocarbazole
64. 3-(Dimethylamino)-6-(2-chloro-4-methoxybenzoyloxy)methyl-1,2,3,4-tetrahydrocarbazole
65. 3-(Dimethylamino)-8-(4-methylbenzoyloxy)methyl-1,2,3,4-tetrahydrocarbazole.

By a conventional oxidation procedure, e.g., oxidation with manganese dioxide there are obtained respectively from the compounds of Examples 55 and 56:

66. 3-(Dimethylamino)-6-formyl-1,2,3,4-tetrahydrocarbazole
67. 3-(Dimethylamino)-8-formyl-1,2,3,4-tetrahydrocarbazole.

By reaction of the appropriate carboxylic acid chlorides, prepared by conventional procedures from compounds 39 and 40 above, with the appropriate amines there are obtained:

68. 3-(Dimethylamino)-8-dimethylaminocarbonyl-1,2,3,4-tetrahydrocarbazole
69. 3-(Dimethylamino)-6-dihexylaminocarbonyl-1,2,3,4-tetrahydrocarbazole
70. 3-(Dimethylamino)-8-(4-morpholinyl)carbonyl-1,2,3,4-tetrahydrocarbazole
71. 3-(Dimethylamino)-6-(1-pyrrolidinyl)carbonyl-1,2,3,4-tetrahydrocarbazole
72. 3-(Dimethylamino)-8-(1-piperazinyl)carbonyl-1,2,3,4-tetrahydrocarbazole
73. 3-(Dimethylamino)-6-(4-methyl-1-piperazinyl)carbonyl-1,2,3,4-tetrahydrocarbazole
74. 3-(Dimethylamino)-6-(4-thiomorpholinyl)carbonyl-1,2,3,4-tetrahydrocarbazole
75. 3-(Dimethylamino)-8-(1-piperidinyl)carbonyl-1,2,3,4-tetrahydrocarbazole
76. 3-(Dimethylamino)-8-(4-phenyl-1-piperazinyl)carbonyl-1,2,3,4-tetrahydrocarbazole
77. 3-(Dimethylamino)-6-[4-(4-trifluoromethylphenyl)-1-piperazinyl]carbonyl-1,2,3,4-tetrahydrocarbazole
78. 3-(Dimethylamino)-8-[4-(2-chloro-4-methoxyphenyl)-1-piperazinyl]carbonyl-1,2,3,4-tetrahydrocarbazole
79. 3-(Dimethylamino)-6-[4-(4-tolyl)-1-piperazinyl]carbonyl-1,2,3,4-tetrahydrocarbazole.

By using conventional reduction procedures there are obtained from compounds 68 to 79 inclusive:
80. 3-(Dimethylamino)-8-dimethylaminomethyl-1,2,3,4-tetrahydrocarbazole
81. 3-(Dimethylamino)-6-dihexylaminomethyl-1,2,3,4-tetrahydrocarbazole
82. 3-(Dimethylamino)-8-(4-morpholinyl)methyl-1,2,3,4-tetrahydrocarbazole
83. 3-(Dimethylamino)-6-(1-pyrrolidinyl)methyl-1,2,3,4-tetrahydrocarbazole
84. 3-(Dimethylamino)-8-(1-piperazinyl)methyl-1,2,3,4-tetrahydrocarbazole
85. 3-(Dimethylamino)-6-(4-methyl-1-piperazinyl)-methyl-1,2,3,4-tetrahydrocarbazole
86. 3-(Dimethylamino)-6-(4-thiomorpholinyl)methyl-1,2,3,4-tetrahydrocarbazole
87. 3-(Dimethylamino)-8-(1-piperidinyl)methyl-1,2,3,4-tetrahydrocarbazole
88. 3-(Dimethylamino)-8-(4-phenyl-1-piperazinyl)-methyl-1,2,3,4-tetrahydrocarbazole
89. 3-(Dimethylamino)-6-[4-(4-trifluoromethylphenyl)-1-piperazinyl]methyl-1,2,3,4-tetrahydrocarbazole
90. 3-(Dimethylamino)-8-[4-(2-chloro-4-methoxyphenyl)-1-piperazinyl]methyl-1,2,3,4-tetrahydrocarbazole
91. 3-(Dimethylamino)-6-[4-(4-tolyl)-1-piperazinyl]-methyl-1,2,3,4-tetrahydrocarbazole.

By following a procedure similar to that described in Example 3 and substituting for p-methoxyphenylhydrazine hydrochloride an equivalent amount of the hydrochlorides of:
4-hydrazino-4'-methoxybiphenyl
2-hydrazino-4'-fluorobiphenyl
2-hydrazino-4'-methylbiphenyl
2-hydrazino-3'-trifluoromethylbiphenyl
(2-phenoxyphenyl)hydrazine
[4-(4-chlorophenoxy)phenyl]hydrazine
[2-(3-trifluoromethylphenoxy)phenyl]hydrazine
[4-(4-tolyloxy)phenyl]hydrazine
there are obtained respectively:
92. 3-(Dimethylamino)-6-(4-methoxyphenyl)-1,2,3,4-tetrahydrocarbazole
93. 3-(Dimethylamino)-8-(4-fluorophenyl)-1,2,3,4-tetrahydrocarbazole
94. 3-(Dimethylamino)-8-(4-tolyl)-1,2,3,4-tetrahydrocarbazole
95. 3-(Dimethylamino)-8-(3-trifluoromethylphenyl)-1,2,3,4-tetrahydrocarbazole
96. 3-(Dimethylamino)-8-phenoxy-1,2,3,4-tetrahydrocarbazole
97. 3-(Dimethylamino)-6-(4-chlorophenoxy)-1,2,3,4-tetrahydrocarbazole
98. 3-(Dimethylamino)-8-(3-trifluoromethylphenoxy)-1,2,3,4-tetrahydrocarbazole
99. 3-(Dimethylamino)-6-(4-tolyloxy)-1,2,3,4-tetrahydrocarbazole Following a procedure similar to that given in Example 21 and substituting for 4-benzoyloxycyclohexanone an equivalent amount of the following 4-benzoyloxycyclohexanones (prepared in a conventional manner from 4-hydroxycyclohexanone and the appropriate benzoyl chlorides): 4-(4-methoxybenzoyloxy)cyclohexanone, 4-(3,4,5-trimethoxybenzoyloxy)cyclohexanone, 4-(4-methylbenzoyloxy)cyclohexanone, 4-(2-chloro-4-nitrobenzoyloxy)-cyclohexanone, 4-(3-trifluoromethylbenzoyloxy)cyclohexanone, 4-(4-hexylbenzoyloxy)cyclohexanone, 4-(4-isopropylbenzoyloxy)-cyclohexanone, 4-(2-fluorobenzoyloxy)cyclohexanone, 4-(2-ethoxybenzoyloxy)cyclohexanone, 4-(2-nitro-4-methoxybenzoyloxy)cyclohexanone, 4-(4-iodobenzoyloxy)cyclohexanone, 4-(4-bromobenzoyloxy)cyclohexanone and 4-(4-pentyloxybenzoyloxy)cyclohexanone; and substituting for p-tolylhydrazine an equivalent amount of 2-ethylphenylhydrazine, 4-benzylhydrazine, 5-ethoxy-2-nitrophenylhydrazine, 4-propoxyphenylhydrazine, 4-methylthiophenylhydrazine, 4-methylsulfinylphenylhydrazine, 4-methylsulfonylphenylhydrazine, 4-chloro-2-(trifluoromethyl)phenylhydrazine, 4-(diethylamino)phenylhydrazine, 4-acetamidophenylhydrazine, 2-benzyloxyphenylhydrazine, 2-chloro-5-methoxyphenylhydrazine, and 5-chloro-4-methyl-2-nitrophenylhydrazine, there are obtained respectively:
100. 3-(4-Methoxybenzoyloxy)-8-ethyl-1,2,3,4-tetrahydrocarbazole
101. 3-(3,4,5-Trimethoxybenzoyloxy)-6-benzyl-1,2,3,4-tetrahydrocarbazole
102. 3-(4-Methylbenzoyloxy)-5-ethoxy-8-nitro-1,2,3,4-tetrahydrocarbazole
103. 3-(2-Chloro-4-nitrobenzoyloxy)-6-propoxy-1,2,3,4-tetrahydrocarbazole
104. 3-(3-Trifluoromethylbenzoyloxy)-6-methylthio-1,2,3,4-tetrahydrocarbazole
105. 3-(4-Hexylbenzoyloxy)-6-methylsulfinyl-1,2,3,4-tetrahydrocarbazole
106. 3-(4-Isopropylbenzoyloxy)-6-methylsulfonyl-1,2,3,4-tetrahydrocarbazole
107. 3-(2-Fluorobenzoyloxy)-6-chloro-8-(trifluoromethyl)-1,2,3,4-tetrahydrocarbazole
108. 3-(2-Ethoxybenzoyloxy)-6-(diethylamino)-1,2,3,4-tetrahydrocarbazole
109. 3-(2-Nitro-4-methoxybenzoyloxy)-6-acetamido-1,2,3,4-tetrahydrocarbazole
110. 3-(4-Iodobenzoyloxy)-8-benzyloxy-1,2,3,4-tetrahydrocarbazole
111. 3-(4-Bromobenzoyloxy)-8-chloro-5-methoxy-1,2,3,4-tetrahydrocarbazole
112. 3-(4-Pentyloxybenzoyloxy)-5-chloro-6-methyl-8-nitro-1,2,3,4-tetrahydrocarbazole.

Following a procedure similar to that given in Example 21, using 4-benzoyloxycyclohexanone and substituting for p-tolylhydrazine an equivalent amount of:
2-hydrazinobiphenyl, 4-hydrazino-4'-methoxybiphenyl, 2-hydrazino-4'-fluorobiphenyl, 2-hydrazino-4'-methylbiphenyl, 2-hydrazino-3'-trifluoromethylbiphenyl, (2-phenoxyphenyl)-hydrazine, [4-(4-chlorophenoxy)phenyl]hydrazine, [2-(3-trifluoromethylphenoxy)phenyl]hydrazine and [4-(4-tolyloxy)-phenyl]hydrazine there are obtained respectively:
113. 3-(Benzoyloxy)-8-phenyl-1,2,3,4-tetrahydrocarbazole
114. 3-(Benzoyloxy)-6-(4-methoxyphenyl)-1,2,3,4-tetrahydrocarbazole
115. 3-(Benzoyloxy)-8-(4-fluorophenyl)-1,2,3,4-tetrahydrocarbazole
116. 3-(Benzoyloxy)-8-(4-tolyl)-1,2,3,4-tetrahydrocarbazole
117. 3-(Benzoyloxy)-8-(3-trifluoromethylphenyl)-1,2,3,4-tetrahydracarbazole
118. 3-(Benzoyloxy)-8-phenoxy-1,2,3,4-tetrahydrocarbazole
119. 3-(Benzoyloxy)-6-(4-chlorophenoxy)-1,2,3,4-tetrahydrocarbazole
120. 3-(Benzoyloxy)-8-(3-trifluoromethylphenoxy)-1,2,3,4-tetrahydrocarbazole 121. 3-(Benzoyloxy)-6-(4-tolyloxy)-1,2,3,4-tetrahydrocarbazole By following a procedure similar to that described in Example 11, substituting for 3-benzoyloxy-1,2,3,4-tetrahydrocarbazole an equivalent amount of compounds 100 to 115 inclusive and for p-chlorobenzyl chloride an equivalent amount of n-hexyl chloride, 2-phenethyl chloride, 3,3,-dimethylallyl bromide, 2-dimethylaminopropyl chloride, 2-(4-morpholinyl)ethyl chloride, 2-(4-thiomorpholinyl)ethyl chloride, 2-(1-piperidinyl)ethyl chloride, 2-(1-pyrrolidinyl)ethyl chloride, 2-(1-piperazinyl)ethyl chloride, 2-(4-methyl-1-piperazinyl)ethyl chloride, 2-(4-phenyl-1-piperazinyl)ethyl chloride, 3,4-difluorobenzyl chloride, 2,6-dichlorobenzyl bromide, 1-bromo-3-(3-methoxyphenyl)propane, 4-methylbenzyl bromide, and 2,5-dimethylbenzyl chloride, there are obtained respectively:

122. 3-(4-Methoxybenzoyloxy)-8-ethyl-9-(n-hexyl)-1,2,3,4-tetrahydrocarbazole
123. 3-(3,4,5-Trimethoxybenzoyloxy)-6-benzyl-9-(2-phenethyl)-1,2,3,4-tetrahydrocarbazole
124. 3-(4-Methylbenzoyloxy)-5-ethoxy-8-nitro-9-(3,3-dimethylallyl)-1,2,3,4-tetrahydrocarbazole
125. 3-(2-Chloro-4-nitrobenzoyloxy)-6-propoxy-9-(2-dimethylaminopropyl)-1,2,3,4-tetrahydrcarbazole
126. 3-(3-Trifluoromethylbenzoyloxy)-6-methylthio-9-[2-(4-morpholinyl)ethyl]-1,2,3,4-tetrahydracarbozole
127. 3-(4-Hexylbenzoyloxy)-6-methylsulfinyl-9-[2-(4-thiomorpholinyl)ethyl]-1,2,3,4-tetrahydrocarbazole
128. 3-(4-Isopropylbenzoyloxy)-6-methylsulfonyl-9-[2-(1-piperidinyl)ethyl]-1,2,3,4-tetrahydrocarbazole
129. 3-(2-Fluorobenzoyloxy)-6-chloro-8-(trifluormethyl)-9-[2-(1-pyrrolidinyl)ethyl]-1,2,3,4-tetrahydrocarbazole
130. 3-(2-Ethoxybenzoyloxy)-6-(diethylamino)-9-[2-(1-piperazinyl)ethyl]-1,2,3,4-tetrahydrocarbazole
131. 3-(2-Nitro-4-methoxybenzoyloxy)-6-acetamido-9-[2-(4-methyl-1-piperazinyl)ethyl]-1,2,3,4-tetrahydrocarbazole
132. 3-(4-Iodobenzoyloxy)-8-benzyloxy-9-[2-(4-phenyl-1-piperazinyl)ethyl]-1,2,3,4-tetrahydrocarbazole
133. 3-(4-Bromobenzoyloxy)-8-chloro-5-methoxy-9-(3,4-difluorobenzyl)-1,2,3,4-tetrahydrocarbazole
134. 3-(4-Pentyloxybenzoyloxy)-5-chloro-6-methyl-8-nitro-9-(2,6-dichorobenzyl)-1,2,3,4-tetrahydrocarbazole
135. 3-(Benzoyloxy)-8-phenyl-9-[3-(3-methoxyphenyl)-1-propyl]-1,2,3,4-tetrahydrocarbazole
136. 3-(Benzoyloxy)-6-(4-methoxyphenyl)-9-(4-methylbenzyl)-1,2,3,4-tetrahydrocarbazole
137. 3-(Benzoyloxy)-8-(4-fluorophenyl)-9-(2,5-dimethylbenzyl)-1,2,3,4-tetrahydrocarbazole By using conventional ester hydrolysis procedures described hereinbefore there are obtained from compounds 116 to 137 inclusive above the following:

138. 3-(Hydroxy)-8-(4-tolyl)-1,2,3,4-tetrahydrocarbazole
139. 3-(Hydroxy)-8-(3-trifluoromethylphenyl)-1,2,3,4-tetrahydrocarbazole
140. 3-(Hydroxy)-8-phenoxy-1,2,3,4-tetrahydrocarbazole
141. 3-(Hydroxy)-6-(4-chlorophenyl)-1,2,3,4-tetrahydrocarbazole
142. 3-(Hydroxy)-8-(3-trifluoromethylphenoxy)-1,2,3,4-tetrahydrocarbazole
143. 3-(Hydroxy)-6-(4-tolyloxy)-1,2,3,4-tetrahydrocarbazole
144. 3-(Hydroxy)-8-ethyl-9-(n-hexyl)-1,2,3,4-tetrahydrocarbazole
145. 3-(Hydroxy)-6-benzyl-9-(2-phenethyl)-1,2,3,4-tetrahydrocarbazole
146. 3-(Hydroxy)-5-ethoxy-8-nitro-9-(3,3-dimethylallyl)-1,2,3,4-tetrahydrocarbazole
148. 3-(Hydroxy)-6-propoxy-9-(2-dimethylaminopropyl)-1,2,3,4-tetrahydrocarbazole
147. 3-(Hydroxy)-6-methylthio-9-[2-(4-morpholinyl)ethyl]-1,2,3,4-tetrahydrocarbazole
149. 3-(Hydroxy)-6-methylsulfinyl-9-[2-(4-thiomorpholinyl)-ethyl)]1,2,3,4-tetrahydrocarbazole
150. 3-(Hydroxy)-6-methylsulfonyl-9-[2-(1-piperidinyl)ethyl]-1,2,3,4-tetrahydrocarbazole
151. 3-(Hydroxy)-6-chloro-8-(trifluormethyl)-9-[2-(1-pyrrolidinyl)ethyl]-1,2,3,4-tetrahydrocarbazole
152. 3-(Hydroxy)-6-(diethylamino)-9-[2-(1-piperazinyl)ethyl]-1,2,3,4-tetrahydrocarbazole
153. 3-(Hydroxy)-6-acetamido-9-[2-(4-methyl-1-piperazinyl)-ethyl]-1,2,3,4-tetrahydrocarbazole
154. 3-(Hydroxy)-8-benzyloxy-9-[2-(4-phenyl-piperazinyl)-ethyl]-1,2,3,4-tetrahydrocarbazole
155. 3-(Hydroxy)-8-chloro-5-methoxy-9-(3,4-difluorobenzyl)-1,2,3,4-tetrahydrocarbazole
156. 3-(Hydroxy)-5-chloro-6-methyl-8-nitro-9-(2,6-dichlorobenzyl)-1,2,3,4-tetrahydrocarbazole
157. 3-(Hydroxy)-8-phenyl-9-[3-(3-methoxyphenyl)-1-propyl]-1,2,3,4-tetrahydrocarbazole
158. 3-(Hydroxy)-6-(4-methoxyphenyl)-9-(4-methbenzyl)-1,2,3,4-tetrahydrocarbazole
159. 3-(Hydroxy)-8-(4-fluorophenyl)-9-(2,5-dimethylbenzyl)-1,2,3,4-tetrahydrocarbazole Following the conventional procedure given hereinbefore for preparing 3-sulfonyloxy-1,2,3,4-tetrahydrocarbazoles from the corresponding 3-hydroxy compounds there are obtained from compounds 138 to 150 inclusive on reaction with benzenesulfonyl chloride, methylsulfonyl chloride, hexanesulfonyl chloride, benzylsulfonyl chloride, 4-methoxybenzylsulfonyl chloride, 4-fluorobenzylsulfonyl chloride, 4-nitrobenzylsulfonyl chloride, 3,4,5-trimethoxybenzenesulfonyl chloride, 3-(trifluoromethyl)benzenesulfonyl chloride, 4-chlorobenzenesulfonyl chloride, 4-nitrobenzenesulfonyl chloride, 2-chlorobenzenesulfonyl chloride and 2-bromo-4-nitrobenzenesulfonyl chloride and from compounds 151 to 159 inclusive on reaction with 4-toluenesulfonyl chloride respectively the following:

160. 3-(Benzenesulfonyloxy)-8-(4-tolyl)-1,2,3,4-tetrahydrocarbazole
161. 3-(Methylsulfonyloxy)-8-(3-trifluoromethylphenyl)-1,2,3,4-tetrahydrocarbazole
162. 3-(Hexanesulfonyloxy)-8-phenoxy-1,2,3,4-tetrahydrocarbazole
163. 3-(Benzylsulfonyloxy)-6-(4-chlorophenoxy)-1,2,3,4-tetrahydrocarbazole
164. 3-(4-Methoxybenzylsulfonyloxy)-8-(3-trifluoromethylphenoxy)-1,2,3,4-tetrahydrocarbazole
165. 3-(4-Fluorobenzylsulfonyloxy)-6-(4-tolyloxy)-1,2,3,4-tetrahydrocarbazole
166. 3-(4-Nitrobenzylsulfonyloxy)-8-ethyl-9-(n-hexyl)-1,2,3,4-tetrahydrocarbazole
167. 3-(3,4,5-Trimethoxybenzenesulfonyloxy)-6-benzyl-9-(2-phenethyl)-1,2,3,4-tetrahydrocarbazole 168. 3-[3-(Trifluoromethyl)benzenesulfonyloxy]-5-ethoxy-8-nitro-9-(3,3-dimethylallyl)-1,2,3,4-tetrahydrocarbazole
169. 3-(4-Chlorobenzenesulfonyloxy)-6-propoxy-9-(2-dimethylaminopropyl)-1,2,3,4-tetrahydrocarbazole
170. 3-(4-Nitrobenzenesulfonyloxy)-6-methylthio-9-[2-(4-morpholinyl)-ethyl]-1,2,3,4-tetrahydrocarbazole
171. 3-(2-Chlorobenzenesulfonyloxy)-6-methylsulfinyl-9-[2-(4-thiomorpholinyl)ethyl]-1,2,3,4-tetrahydrocarbazole
172. 3-(2-Bromo-4-nitrobenzenesulfonyloxy)-6-methylsulfonyl-9-[2-(1-piperidinyl)ethyl]-1,2,3,4-tetrahydrocarbazole
173. 3-(4-Toluenesulfonyloxy)-6-chloro-8-(trifluoromethyl)-9-[2-(1-pyrrolidinyl)ethyl]-1,2,3,4-tetrahydrocarbazole
174. 3-(4-Toluenesulfonyloxy)-6-(diethylamino)-9-[2-(1-piperazinyl)ethyl]-1,2,3,4-tetrahydrocarbazole
175. 3-(4-Toluenesulfonyloxy)-6-acetamido-9-[2-(4-methyl-1-piperazinyl)ethyl]-1,2,3,4-tetrahydrocarbazole
176. 3-(4-Toluenesulfonyloxy)-8-benzyloxy-9-[2-(4-phenyl-1-piperazinyl)ethyl]-1,2,3,4-tetrahydrocarbazole
177. 3-(4-Toluenesulfonyloxy)-8-chloro-5-methoxy-9-(3,4-difluorobenzyl)-1,2,3,4-tetrahydrocarbazole
178. 3-(4-Toluenesulfonyloxy)-5-chloro-6-methyl-8-nitro-9-(2,6-dichlorobenzyl)-1,2,3,4-tetrahydrocarbazole
179. 3-(4-Toluenesulfonyloxy)-8-phenyl-9-[3-(3-methoxyphenyl)-1-propyl]-1,2,3,4-tetrahydrocarbazole
180. 3-(4-Toluenesulfonyloxy)-6-(4-methoxyphenyl)-9-(4-methylbenzyl)-1,2,3,4-tetrahydrocarbazole
181. 3-(4-Toluenesulfonyloxy)-8-(4-fluorophenyl)-9-(2,5-dimethylbenzyl)-1,2,3,4-tetrahydrocarbazole Following a procedure similar to that described in Example 18 and substituting for n-butylamine an equivalent amount of dimethylamine and for 3-(p-toluenesulfonyloxy)-1,2,3,4-tetrahydrocarbazole an equivalent amount of compounds 160 to 172 there are obtained respectively:

182. 3-(Dimethylamino)-8-(4-tolyl)-1,2,3,4-tetrahydrocarbazole
183. 3-(Dimethylamino)-8-(3-trifluoromethylphenyl)-1,2,3,4-tetrahydrocarbazole
184. 3-(Dimethylamino)-8-phenoxy-1,2,3,4-tetrahydrocarbazole
185. 3-(Dimethylamino)-6-(4-chlorophenoxy)-1,2,3,4-tetrahydrocarbazole
186. 3-(Dimethylamino)-8-(3-trifluoromethylphenoxy)-1,2,3,4-tetrahydrocarbazole
187. 3-(Dimethylamino)-6-(4-tolyloxy)-1,2,3,4-tetrahydrocarbazole
188. 3-(Dimethylamino)-8-ethyl-9-(n-hexyl)-1,2,3,4-tetrahydrocarbazole
189. 3-(Dimethylamino)-6-benzyl-9-(2-phenethyl)-1,2,3,4-tetrahydrocarbazole
190. 3-(Dimethylamino)-5-ethoxy-8-nitro-9-(3,3-dimethylallyl)-1,2,3,4-tetrahydrocarbazole
191. 3-(Dimethylamino)-6-propoxy-9-(2-dimethylaminopropyl)-1,2,3,4-tetrahydrocarbazole
192. 3-(Dimethylamino)-6-methylthio-9-[2-(4-morpholinyl)-ethyl]-1,2,3,4-tetrahydrocarbazole
193. 3-(Dimethylamino)-6-methylsulfinyl-9-[2-(4-thiomorpholinyl)-ethyl]-1,2,3,4-tetrahydrocarbazole
194. 3-(Dimethylamino)-6-methylsulfonyl-9-[2-(1-piperidinyl)-ethyl]-1,2,3,4-tetrahydrocarbazole Following a procedure similar to that described in Example 18 and substituting for 3-(p-toluenesulfonyloxy)-1,2,3,4-tetrahydrocarbazole an equivalent amount of compounds 173 to 181 inclusive and substituting for n-butylamine the following amines:
4-(3-Trifluoromethylphenyl)piperazine
4-(4-Chlorophenyl)piperazine
4-(4-Nitrophenyl)piperazine
4-(2-Chloro-4-methoxyphenyl)piperazine
4-(3,4,5-Trimethoxyphenyl)piperazine
4-(4-Tolyl)piperazine
4-(4-Bromophenyl)piperazine
4-(2-Chloro-4-nitrophenyl)piperazine
4-(4-Isopropylphenyl)piperazine there are obtained respectively:

195. 3-[4-(3-Trifluoromethylphenyl)-1-piperazinyl]-6-chloro-8-(trifluoromethyl)-9-[2-(1-pyrrolidinyl)ethyl]-1,2,3,4-tetrahydrocarbazole
196. 3-[4-(4-Chlorophenyl)-1-piperazinyl]-6-(diethylamino)-9-[2-(1-piperazinyl)ethyl]-1,2,3,4-tetrahydrocarbazole
197. 3-[4-(4-Nitrophenyl)-1-piperazinyl]-6-acetamido-9-[2-(4-methyl-1-piperazinyl)ethyl]-1,2,3,4-tetrahydrocarbazole
198. 3-[4-(2-Chloro-4-methoxyphenyl)-1-piperazinyl]-8-benzyloxy-9-[2-(4-phenyl-1-piperazinyl)ethyl]-1,2,3,4-tetrahydrocarbazole
199. 3-[4-(3,4,5-Trimethoxyphenyl)-1-piperazinyl]-8-chloro-5-methoxy-9-(3,4-difluorobenzyl)-1,2,3,4-tetrahydrocarbazole
200. 3-[4-(4-Tolyl)-1-piperazinyl]-5-chloro-6-methyl-8-nitro-9-(2,6-dichlorobenzyl)-1,2,3,4-tetrahydrocarbazole
201. 3-[4-(4-Bromophenyl)-1-piperazinyl]-8-phenyl-9-[3-(3-methoxyphenyl)-1-propyl]-1,2,3,4-tetrahydrocarbazole
202. 3-[4-(2-Chloro-4-nitrophenyl)-1-piperazinyl]-6-(4-methoxyphenyl)-9-(4-methylbenzyl)-1,2,3,4-tetrahydrocarbazole
203. 3-[4-(4-Isopropylphenyl)-1-piperazinyl]-8-(4-fluorophenyl)-9-(2,5-dimethylbenzyl)-1,2,3,4-tetrahydrocarbazole

EXAMPLE 204

3-(Dimethylamino)-6,8-difluoro-1,2,3,4-tetrahydrocarbazole

A mixture of 19.4 g. of 4-dimethylaminocyclohexanone hydrochloride and 18.1 g. of 2,4-difluorophenylhydrazine hydrochloride in 250 ml. of absolute ethyl alcohol was refluxed for four hours, cooled to room temperature and filtered. The filtrate was evaporated to dryness and the crude hydrochloride salt was dissolved in 500 ml. of water, the solution was made alkaline, and the resulting white solid was filtered to give 11.2 g. of 3-(dimethylamino)-6,8-difluoro-1,2,3,4-tetrahydrocarbazole, m.p. 180°–183° C. (ethylene dichloride).

The free base was converted to the hydrochloride salt, m.p. 268°–270° C.

The free base was slurried in isopropyl alcohol and an equivalent amount of methanesulfonic acid was added. The solution was concentrated under reduced pressure, cooled and filtered to give the methanesulfonate salt, m.p. 187°–189° C.

The free base (12.5 g., .05 m.) and dibenzoyl l-tartaric acid hydrate (13.8 g., .05 m.) were dissolved in 300 ml.

of methyl alcohol, and 100 ml. of water was added. An aliquot of this solution was scratched until crystals formed and the main solution was seeded with these crystals and refrigerated overnight. The resulting crystals were filtered and the filtrate was refrigerated for four days and the resulting additional crop of crystals were filtered. Two crops were combined, slurried in 100 ml. of water and treated with 5 ml. of 35% sodium hydroxide and stirred for fifteen minutes. The resulting solid was filtered and recrystallized from benzenehexane to give 2.4 g. of 1-3-(dimethylamino)-6,8-difluoro-1,2,3,4-tetrahydrocarbazole which was converted to the hydrochloride, m.p. 278°–279° C., $[\alpha]_D^{25} = -69.8°$ (2% in H$_2$O). A sample of the hydrochloride salt was converted to the free base, 1-3-(dimethylamino)-6,8-difluoro-1,2,3,4-tetrahydrocarbazole, m.p. 142.5°–143.5° C.

Following a procedure similar to that described in the previous paragraph but substituting for dibenzoyl 1-tartaric acid hydrate the corresponding d-isomer there was obtained d-3-(dimethylamino)-6,8-difluoro-1,2,3,4-tetrahydrocarbazole, m.p. 143°–144° C., $[\alpha]_D^{24} = +86.3°$ (2% in MeOH).

The 2,4-difluorophenylhydrazine hydrochloride (m.p. 244°–246° C.) was prepared from 2,4-difluoroaniline hydrochloride using a procedure similar to that described in Example 5 for the preparation of 4-benzoyloxyphenylhydrazine hydrochloride.

EXAMPLE 205

3-(Dimethylamino)-6-phenoxy-1,2,3,4-tetrahydrocarbazole

To a solution of 14.1 g. of 4-dimethylaminocyclohexanone in 100 ml. of a 6-N solution of hydrogen chloride in absolute ethyl alcohol was added 23.5 g. of 4-phenoxyphenylhydrazine hydrochloride and the mixture was heated at reflux for six hours. The mixture was filtered, the filtrate was made alkaline with 10% potassium hydroxide and extracted with chloroform, and the chloroform extract was washed with water and evaporated to dryness under reduced pressure to give 3-(dimethylamino)-6-phenoxy-1,2,3,4-tetrahydrocarbazole.

The free base was taken up in ether and ethereal hydrogen chloride was added and the resulting solid was filtered to give, on recrystallization from isopropyl alcohol, 25 g. of 3-(dimethylamino)-6-phenoxy-1,2,3,4-tetrahydrocarbazole hydrochloride, m.p. 235°–240° C.

EXAMPLES 206–233

By following the manipulative procedure described above in Example 205, substituting for the 4-phenoxyphenylhydrazine hydrochloride used therein equivalent amounts of the phenylhydrazines listed in Table II below, the respective 3-(N=B)-9-R-1,2,3,4-tetrahydrocarbazoles of formula I (where N=B is dimethylamino and R is hydrogen) listed below in Table I were prepared.

Table I 3-(Dimethylamino)-Q$_{1-4}$-1,2,3,4-tetrahydrocarbazole

| Example | Q$_{1-4}$ (other than hydrogen) | Salt | M.P. (° C.) |
|---|---|---|---|
| 206 | 7,8-dimethyl | HCl | 318–322 |
| 207 | 6,7-difluoro | HCl | 257–260 |
| 208 | 5,8-dimethyl | — | 138–148 |
| 209 | 6,8-dichloro | — | 192–193.5 |
| 210 | 7,8-dichloro | — | 181–182 |
| 211 | 8-bromo | — | 136–137 |
|  |  | HCl | 273–275 |
| 212 | 8-(trifluoromethyl) | — | 77–80 |

Table I-continued 3-(Dimethylamino)-Q$_{1-4}$-1,2,3,4-tetrahydrocarbazole

| Example | Q$_{1-4}$ (other than hydrogen) | Salt | M.P. (° C.) |
|---|---|---|---|
| 213 | 5-chloro-8-methoxy | HCl | 304–307 |
| 214 | 8-methoxy | — | 194–195 |
| 215 | 8-methylthio | — | 136–139 |
| 216 | 8-methylsulfonyl | HCl | 274–275 |
| 217 | 8-iodo | HCl | 265–266 |
| 218 | 8-chloro-5-methyl | — | 167–169 |
| 219 | 8-bromo-5-fluoro | — | 162–163 |
| 220 | 8-bromo-5-chloro | — | 175–181 |
| 221 | 5,7-dimethyl | — | 124–128 |
| 222 | 5,8-difluoro | HCl | >260 |
| 223 | 5,6,7,8-tetrafluoro | — | 219–222 |
| 224 | 8-fluoro-5-methyl | HCl | 182–184 |
| 225 | 8-chloro-5-(trifluoromethyl) | HCl | 291–293 |
| 226 | 7,8-difluoro | — | 200–202 |
| 227 | 8-chloro-7-methyl | HCl | 280–282 |
| 228 | 5-fluoro-8-(4-fluorophenyl) | — | 163–166 |
| 229 | 8-phenyl | — | 131–134 |
| 230 | 6-acetamido | HCl | 304–306 |
| 231 | 8-(benzyloxy) | HCl | 252–253 |
| 232 | 8-propyl | HCl | 242–244 |
| 233 | 8-bromo-5-methyl | — | 149–150 |

The phenylhydrazines of formula IVA (where R is hydrogen), listed in Table II below, used in the preparation of the compounds of Examples 206–233 above were prepared from the corresponding anilines using a procedure similar to that described in Example 5. The phenylhydrazines were isolated either in the free base form or as the hydrochloride salts. In some cases the products were used directly in the next step without recrystallization.

Table II (Q$_{1-4}$)-Phenylhydrazine

| Q$_{1-4}$ (other than hydrogen) | Salt | M.P. (° C.) |
|---|---|---|
| 2,3-dimethyl | HCl | 218–220 |
| 3,4-difluoro | HCl |  |
| 2,5-dimethyl | HCl |  |
| 2,4-dichloro | — | 91–94 |
| 2,3-dichloro | — | 111–114 |
| 2-bromo | HCl | 197–198 |
| 2-(trifluoromethyl) | — | 61–63 |
| 2-methoxy-5-chloro | HCl |  |
| 2-methoxy | HCl |  |
| 2-methylthio | HCl | 142–144 |
| 2-methylsulfonyl | HCl |  |
| 2-iodo | HCl | 175 (dec.) |
| 2-chloro-5-methyl | HCl |  |
| 2-bromo-5-fluoro | HCl | 174–175 |
| 2-bromo-5-chloro | HCl |  |
| 3,5-dimethyl | HCl | 155–157 |
| 2,5-difluoro | HCl |  |
| 2,3,4,5-tetrafluoro | HCl | 207 (dec.) |
| 2-fluoro-5-methyl | HCl | 195–197 |
| 2-chloro-5-(trifluoromethyl) | — |  |
| 2,3-difluoro | HCl | 81–84 |
| 2-chloro-3-methyl | — | 217 (dec.) |
| 5-fluoro-2-(4-fluorophenyl) | — | 105–115 |
| 2-phenyl | HCl |  |
| 4-acetamido | HCl | 173 (dec.) |
| 2-benzyloxy | HCl | 153–155 |
| 2-propyl | HCl |  |
| 2-bromo-5-methyl | HCl | 188–190 |

EXAMPLE 234

3-(Dimethylamino)-5-(trifluoromethyl)-1,2,3,4-tetrahydrocarbazole

To a solution of 4 g. of 3-(dimethylamino)-8-chloro-5-(trifluoromethyl)-1,2,3,4-tetrahydrocarbazole (Example 225) in 200 ml. of ethyl alcohol was added 1.4 g. of potassium hydroxide and 1 g. of 10% palladium on charcoal and the mixture was subjected to a hydrogen atmosphere at room temperature and 50 psig. When approximately an equimolar amount of hydrogen had reacted the mixture was acidified with 10% hydrochloric acid, diluted with 50 ml. of water, filtered, made alkaline with 10% sodium hydroxide and concentrated to a small volume under reduced pressure. The resulting precipitate was collected by filtration and washed with water to give 3.6 g. of 3-(dimethylamino)-5-(trifluoromethyl)-1,2,3,4-tetrahydrocarbazole, m.p. 222°–225° C.

EXAMPLE 235

3-(Dimethylamino)-5-fluoro-1,2,3,4-tetrahydrocarbazole

Following a procedure similar to that described in Example 234 but using 2 g. of 3-(dimethylamino)-8-bromo-5-fluoro-1,2,3,4-tetrahydrocarbazole (Example 219), in 100 ml. of methyl alcohol, 1 g. of 10% palladium on charcoal and 1 g. of potassium hydroxide in 2 ml. of water there was obtained, after recrystallization from benzene, 1.3 g. of 3-(dimethylamino)-5-fluoro-1,2,3,4-tetrahydrocarbazole, m.p. 166°–168° C.

EXAMPLE 236

3-(Dimethylamino)-5-chloro-1,2,3,4-tetrahydrocarbazole

To a solution of 14.8 g. of 3-(dimethylamino)-8-bromo-5-chloro-1,2,3,4-tetrahydrocarbazole (Example 220) in 200 ml. of methyl alcohol was added a slurry of 2 g. of 10% palladium on charcoal in 100 ml. of ethyl alcohol. The mixture was subjected to a hydrogen atmosphere at about 60 psig at room temperature. When an equimolar amount of hydrogen had reacted (about 10 minutes), the uptake of hydrogen ceased. The mixture was filtered, the filtrate was evaporated to dryness, the residue was dissolved in water and the resulting solution was made alkaline with dilute sodium hydroxide. The resulting solids were collected by filtration and recrystallized from ethyl alcohol to give 6.2 g. of 3-(dimethylamino)-5-chloro-1,2,3,4-tetrahydrocarbazole, m.p. 212°–214° C.

When 4 g. of 3-(dimethylamino)-8-bromo-5-fluoro-1,2,3,4-tetrahydrocarbazole was subjected to a procedure similar to that described in Example 234, that is, in the presence of 1 g. of potassium hydroxide, there was obtained 3-(dimethylamino)-1,2,3,4-tetrahydrocarbazole (Example 1) which was converted to 1.2 g. of the hydrochloride salt.

EXAMPLE 237

3-(Dimethylamino)-8-chloro-5-ethoxycarbonyl-1,2,3,4-tetrahydrocarbazole

Following a procedure similar to that described in Example 43 and using 14.2 g. of 4-dimethylaminocyclohexanone hydrochloride and 13.6 g. of 2-chloro-5-carboxyphenylhydrazine [m.p. 198° C. (dec.)] in 250 ml. of 4-N hydrogen chloride in ethyl alcohol there was obtained on evaporation of the reaction mixture to dryness, followed by recrystallization of the residue from ethyl alcohol, 6.1 g. of 3-(dimethylamino)-8-chloro-5-ethoxycarbonyl-1,2,3,4-tetrahydrocarbazole hydrochloride, m.p. 236°–237° C.

EXAMPLE 238

3-(Dimethylamino)-7-fluoro-1,2,3,4-tetrahydrocarbazole

A solution of 35.5 g. of dimethylaminocyclohexanone hydrochloride and 34.5 g. of 3-fluorophenylhydrazine hydrochloride in 500 ml. of absolute ethyl alcohol was heated at reflux for twenty hours and then cooled in an ice bath. The resulting crystals were collected by filtration, suspended in chloroform, and treated with dilute potassium hydroxide. The chloroform layer was separated and evaporated to dryness under reduced pressure to give, after recrystallization from isopropyl alcohol, 31.5 g. of 3-(dimethylamino)-7-fluoro-1,2,3,4-tetrahydrocarbazole, m.p. 174°–176° C.

EXAMPLE 239

3-(Dimethylamino)-7-(benzyloxy)-1,2,3,4-tetrahydrocarbazole

A solution of 15.8 g. of 4-dimethylaminocyclohexanone hydrochloride and 20.3 g. of 3-benzyloxyphenylhydrazine hydrochloride (m.p. 165°–168° C.) in 225 ml. of absolute ethyl alcohol was heated under reflux for three hours, cooled to room temperature, and diluted with 50 ml. of water. After standing for three hours the resulting crystals were collected by filtration and washed with ethyl alcohol to give, after recrystallization from ethyl alcohol, 6.1 g. of 3-(dimethylamino)-7-(benzyloxy)-1,2,3,4-tetrahydrocarbazole hydrochloride, m.p. 237°–239° C.

EXAMPLE 240

3-(Dimethylamino)-7-methoxy-1,2,3,4-tetrahydrocarbazole

A solution of 7 g. of dimethylaminocyclohexanone and 8.4 g. of 3-methoxyphenylhydrazine hydrochloride in 40 ml. of absolute ethyl alcohol and 12 ml. of 4-N hydrogen chloride in ethyl alcohol was heated under reflux for two hours. The reaction mixture was allowed to stand for sixteen hours, filtered, and the filtrate was evaporated to dryness under reduced pressure. The residue was taken up in water, made alkaline with dilute sodium hydroxide and extracted with ether. The ether extract was washed with water, dried, ethereal hydrogen chloride was added, and the resulting oily precipitate was collected by decantation, recrystallized twice from isopropyl alcohol, suspended in chloroform and treated with dilute sodium hydroxide. The chloroform extract was evaporated to dryness under reduced pressure to give 3-(dimethylamino)-7-methoxy-1,2,3,4-tetrahydrocarbazole, m.p. 100°–105° C.

EXAMPLE 241

3-(Dimethylamino)-5-ethyl-1,2,3,4-tetrahydrocarbazole

A solution of 21.2 g. of 4-dimethylaminocyclohexanone hydrochloride and 20.7 g. of 3-ethylphenylhydrazine hydrochloride (m.p. 205°–207° C.) in 200 ml. of absolute ethyl alcohol was heated under reflux for two hours, filtered, and evaporated to dryness. The residual oil was taken up in ether, filtered, and the filtrate was treated with dilute sodium hydroxide, separated, dried, allowed to stand for sixteen hours, and the resulting crystals were collected by filtration. The ether filtrate was extracted six times with warm cyclohexane. The cyclohexane was evaporated to dryness and the residue recrystallized from ether-hexane. The resulting crystals were collected by filtration, combined with the crystals previously obtained above and recrystallized from cyclohexane to give 4.1 g. of 3-(dimethylamino)-5-ethyl-1,2,3,4-tetrahydrocarbazole, m.p. 157°–161° C.

EXAMPLE 242

3-(Dimethylamino)-6,7-dimethyl-1,2,3,4-tetrahydrocarbazole

A solution of 11.5 g. of 4-dimethylaminocyclohexanone hydrochloride and 11 g. of 3,4-dimethylphenylhydrazine hydrochloride in 200 ml. of absolute ethyl alcohol was heated under reflux for 6 hours, cooled, filtered, and the filtrate was diluted with ether. The oily precipitate, which was collected by decantation and solidified on standing, was suspended in boiling isopropyl alcohol, filtered and dissolved in methyl alcohol. This solution was diluted with isopropyl alcohol and the methyl alcohol was removed by distillation. The cooled mixture was filtered to give 9.2 g. of a solid which was suspended in ether and treated with dilute potassium hydroxide. The ether extract was evaporated to dryness and the residue was suspended and boiled in hexane and filtered to give 3.2 g. of 3-(dimethylamino)-6,7-dimethyl-1,2,3,4-tetrahydrocarbazole, m.p. 183°–187° C.

EXAMPLE 243

A.
3-(Dimethylamino)-7-chloro-5-methyl-1,2,3,4-tetrahydrocarbazole and (B)
3-(Dimethylamino)-5-chloro-7-methyl-1,2,3,4-tetrahydrocarbazole A solution of 20 g. of 4-dimethylaminocyclohexanone hydrochloride and 19 g. of 3-chloro-5-methylphenylhydrazine hydrochloride in 250 ml. of absolute ethyl alcohol and 25 ml. of 4-N hydrogen chloride in absolute ethyl alcohol was heated under reflux for eight hours. The cooled reaction mixture was filtered and the solids were suspended in chloroform and treated with 10% potassium hydroxide solution. The chloroform extract was evaporated to dryness under reduced pressure, the residue was triturated with ether and the resulting solids were collected by filtration and dissolved in a large volume of ether and treated with ethereal hydrogen chloride. The ether was evaporated and the residue was recrystallized from water. The resulting crystals were suspended in ether treated with dilute potassium hydroxide and the ether extract was dried and evaporated to dryness to give 3.2 g. of 3-(dimethylamino)-7-chloro-5-methyl-1,2,3,4-tetrahydrocarbazole, m.p. 192°–196° C. The reaction mixture ethyl alcohol filtrate from above was evaporated to dryness, the residue was triturated in ether and the resulting solid was collected by filtration and recrystallized from benzene and then from ethyl acetate to give 3.3 g. of a solid which was dissolved in ether and treated with ethereal hydrogen chloride. The resulting crystals were collected by filtration and dissolved in water. This aqueous mixture was filtered to remove insoluble material and the filtrate was made alkaline with dilute potassium hydroxide and extracted with ether. The ether was evaporated to dryness to give, after recrystallization from ethyl acetate, 1.3 g. of 3-(dimethylamino)-5-chloro-7-methyl-1,2,3,4-tetrahydrocarbazole, m.p. 179°–183° C. which contained about 6% of the 7-chloro-5-methyl isomer (A) as determined by gas chromatographic analysis.

EXAMPLE 244

A.
3-(Dimethylamino)-6-fluoro-5-methyl-1,2,3,4-tetrahydrocarbazole and (B)
3-(Dimethylamino)-6-fluoro-7-methyl-1,2,3,4-tetrahydrocarbazole A solution of 16.5 g. of 4-dimethylaminocyclohexanone and 17.7 g. of 4-fluoro-3-methylphenylhydrazine hydrochloride in 200 ml. of absolute ethyl alcohol and 60 ml. of 5-N hydrogen chloride in absolute ethyl alcohol was heated under reflux for two hours, cooled, filtered and evaporated to dryness under reduced pressure. The residue was dissolved in water, the solution was made alkaline with dilute sodium hydroxide solution and extracted with ether. The ether-water combination was filtered to yield 4.3 g. of crystals, m.p. 202°–206° C. The ether layer was separated and dried and on standing yielded an additional crop of crystals, m.p. 202°–206° C. The ether was evaporated to dryness under reduced pressure and the residue was dissolved in benzene and a small amount of undissolved solids were collected by filtration and combined with the above two crops. The combined crops were slurried in hot cyclohexane, the mixture was filtered, and the resulting solid was dissolved in ethyl alcohol and treated with hydrogen chloride in ethyl alcohol. The resulting crystals were filtered to give 4.6 g. of 3-(dimethylamino)-6-fluoro-5-methyl-1,2,3,4-tetrahydrocarbazole hydrochloride, m.p. 228°–230° C. The benzene filtrate from above was evaporated to dryness and the semisolid residue was recrystallized two times from cyclohexane to give 12.3 g. of crystals, m.p. 118°–119° C. A solution in absolute ethyl alcohol was treated with hydrogen chloride in absolute ethyl alcohol to give 10 g. of 3-(dimethylamino)-6-fluoro-7-methyl-1,2,3,4-tetrahydrocarbazole hydrochloride, m.p. 279°–281° C.

EXAMPLE 245

A.
3-(Dimethylamino)-5-methyl-1,2,3,4-tetrahydrocarbazole and B.
3-(Dimethylamino)-7-methyl-1,2,3,4-tetrahydrocarbazole A solution of 28.2 g. of 4-dimethylaminocyclohexanone and 31.7 g. of 3-methylphenylhydrazine hydrochloride in 150 ml. of absolute ethyl alcohol and 150 ml. of 6-N hydrogen chloride in ethyl alcohol was heated under reflux for three hours, cooled and filtered. The solid was suspended in ether and treated with dilute potassium hydroxide and the ether extract was evaporated to dryness to give an oil which crystallized on scratching in ether. These crystals were collected by filtration and triturated successively in fresh portions of ether. The crystalline material so obtained was dissolved in hot xylene and adsorbed on a column of aluminum oxide, 30 cm. by 25 mm., which was eluted with chloroform. The combined chloroform eluates were evaporated to dryness to give, after recrystallization from xylene, 6.4 g. of 3-(dimethylamino)-5-methyl-1,2,3,4-tetrahydrocarbazole, m.p. 203°–204° C. The combined ether solutions, resulting from the triturations above, were evaporated to dryness to give 18.4 g. of crystals, m.p. 130°–140° C., which were dissolved in hot xylene and adsorbed on a column of aluminum oxide, 30 cm. by 25 mm., which was eluted with ether. The combined eluates were evaporated to dryness to give, after recrystallization from ether, 12.5 g. of 3-(dimethylamino)-7-methyl-1,2,3,4-tetrahydrocarbazole, m.p. 134°-138° C.

Alternatively the 5-methyl isomer (A) was prepared both from the 8-bromo-5-methyl- and 8-chloro-5-methyl-3-(dimethylamino)-1,2,3,4-tetrahydrocarbazoles (Examples 233 and 218 respectively) following a reductive procedure similar to that described in Example 234 above.

The phenylhydrazines used in the preparations of the compounds of Examples 234–245 above were prepared from the corresponding anilines using a procedure similar to that described in Example 5.

EXAMPLE 246

3-(Dimethylamino)-8-nitro-1,2,3,4-tetrahydrocarbazole

Following a procedure similar to that described in Example 39 and using 14.1 g. of 4-dimethylaminocyclohexanone and 19 g. of 2-nitrophenylhydrazine hydrochloride in 150 ml. of absolute ethyl alcohol there was obtained 27.8 g. of 4-dimethylaminocyclohexanone 2-nitrophenylhydrazone hydrochloride. Following a procedure similar to that of Example 39 and using 43.3 g. of 4-dimethylaminocyclohexanone 2-nitrophenylhydrazone hydrochloride in 250 ml. of 2% hydrogen chloride in acetic acid there was obtained, after recrystallization from isopropyl alcohol, 12.2 g. of 3-(dimethylamino)-8-nitro-1,2,3,4-tetrahydrocarbazole, m.p. 173°-174° C.

EXAMPLE 247

3-(1-Piperidyl)-6,8-difluoro-1,2,3,4-tetrahydrocarbazole

A solution of 10.2 g. of 4-(1-piperidyl)-cyclohexanone, 8.1 g. of 2,4-difluorophenylhydrazine, and 11 g. of methanesulfonic acid in 100 ml. of absolute ethyl alcohol was heated under reflux for 12 hours, cooled, filtered, and the filtrate was evaporated to dryness under reduced pressure. The residue was treated in ether with 10% potassium hydroxide solution and the ether extract was washed with water, dried, and treated with hydrogen chloride in ethyl alcohol (excess HCl was avoided). The resulting gummy precipitate was separated by decantation and suspended in boiling isopropyl alcohol. The hot mixture was filtered to give, after recrystallization from absolute ethyl alcohol, 4.5 g. of 3-(1-piperidyl)-6,8-difluoro-1,2,3,4-tetrahydrocarbazole hydrochloride, m.p. > 290° C.

PREPARATION OF 4-(1-PIPERIDYL)-CYCLOHEXANONE

A solution of 17 g. of piperidine and 43.6 g. of 4-benzoyloxycyclohexanone in 200 m. of toluene was heated under reflux and the water formed in the reaction was collected by means of a water-trap. When the stoichiometric amount of water had formed the solution was evaporated to dryness under reduced pressure. The resulting enamine was dissolved in 200 ml. of absolute ethyl alcohol, 3 g. of 10% palladium on charcoal was added and the mixture was subjected to a hydrogen atmosphere at about 30 psig until hydrogen uptake ceased. The catalyst was removed by filtration, and the solution was evaporated to dryness under reduced pressure. The resulting oil was dissolved in 200 ml. of ethyl alcohol, a solution of 11.2 g. of potassium hydroxide in 200 ml. of water was added and the solution was heated under reflux for six hours. The alcohol was evaporated under reduced pressure, and the aqueous mixture was extracted with chloroform to give, on evaporation to dryness, 37 g. of 4-(1-piperidyl)-cyclohexanol as an oil. To a solution of this oil in 100 ml. of acetic acid at 15° C. was added a solution of 20 g. of chromium trioxide in 35 ml. of water and 75 ml. of acetic acid and the resulting solution was stirred at room temperature for 4 hours, allowed to stand for eighteen hours, and poured into 1 liter of dilute ammonium hydroxide. This strongly alkaline solution was extracted with ether and then chloroform. The extracts were evaporated to dryness and the resulting oil was distilled to give 24.2 g. of 4-(1-piperidyl)-cyclohexanone, b.p. 143°-155° C (10 mm.), which contained approximately 25% of the unoxidized alcohol. This material was then used without further purification in the above procedure.

EXAMPLE 248

A.

3-(Methylamino)-7-methyl-1,2,3,4-tetrahydrocarbazole and B.

3-(Methylamino)-5-methyl-1,2,3,4-tetrahydrocarbazole

A solution of 15 g. of 4-methylaminocyclohexanone and 18.4 g. of 3-methylhydrazine hydrochloride in 200 ml. of absolute ethyl alcohol and 50 ml. of 4-N hydrogen chloride in absolute ethyl alcohol was heated under reflux for six hours, cooled, and filtered to give 12.3 g. of solids which were slurried in 50 ml. of water. The slurry was cooled, the solids were collected by filtration, suspended in ether-chloroform, and the suspension was treated with dilute potassium hydroxide. The ether-chloroform extract was evaporated to dryness under reduced pressure to give 7.6 g. of 3-(methylamino)-7-methyl-1,2,3,4-tetrahydrocarbazole, m.p. 163°-166° C. The alcoholic reaction mixture filtrate was evaporated to dryness under reduced pressure, the residue was boiled in isopropyl alcohol, and the insoluble material was collected by filtration, dissolved in water and the resulting solution was made alkaline with dilute potassium hydroxide. The resulting solids were collected by filtration to give, after recrystallization from ethyl acetate, 3.6 g. of 3-(methylamino)-5-methyl-1,2,3,4-tetrahydrocarbazole, m.p. 187°-190° C., which contained about 6% of the 7-methyl isomer as determined by gas chromatographic analysis.

EXAMPLE 249

3-(Methylamino)-6,8-difluoro-1,2,3,4-tetrahydrocarbazole

A solution of 3.5 g. of 4-methylaminocyclohexanone, 5.1 g. of 2,4-difluorophenylhydrazine hydrochloride, and 4 g. of methanesulfonic acid in 50 ml. of absolute ethyl alcohol was heated under reflux for four hours, cooled, and filtered. The resulting solids were washed with isopropanol and treated in chloroform with 10% potassium hydroxide solution. The chloroform extract was evaporated to dryness to give 3-(methylamino)-6,8-difluoro-1,2,3,4-tetrahydrocarbazole, m.p. 135°-138° C., which was converted to the hydrochloride salt, m.p. > 280° C.

EXAMPLE 250

3-(Dimethylamino)-8-aminocarbonyl-1,2,3,4-tetrahydrocarbazole

To a cooled slurry of 14 g. of 3-(dimethylamino)-8-carboxy-1,2,3,4-tetrahydrocarbazole (Example 39) in 500 ml. of dry benzene was added 17.7 ml. of thionyl chloride and the mixture was heated under reflux for three hours, cooled, and filtered. The resulting carboxylic acid chloride was added to 100 ml. of concentrated ammonium hydroxide and the mixture was stirred for one-half hour, filtered, and the solids were washed with water and isopropyl alcohol to give, after recrystallization from dimethylformamide, 9.1 g. of 3-(dimethylamino)-8-aminocarbonyl-1,2,3,4-tetrahydrocarbazole, m.p. 252°–254° C.

EXAMPLE 251

3-(Dimethylamino)-8-cyano-1,2,3,4-tetrahydrocarbazole 3-(Dimethylamino)-8-bromo-1,2,3,4-tetrahydrocarbazole (18.8 g.)(Example 211) and 17.5 g. of cuprous cyanide in 150 ml. of dimethylformamide was heated under reflux for four hours. The warm reaction mixture was poured into a solution of 200 ml. of ethylenediamine in 400 ml. of water. This was mixed thoroughly and extracted several times with chloroform. The chloroform layer was separated and washed with a dilute solution of ethylenediamine, water, saturated salt solution, and evaporated to dryness to give, after recrystallization from benzene, 6.9 g. of 3-(dimethylamino)-8-cyano-1,2,3,4-tetrahydrocarbazole, m.p. 177°–179° C.

EXAMPLE 252

3-(1-Pyrrolidinyl)-8-methyl-1,2,3,4-tetrahydrocarbazole

To a solution of 87.3 g. of 4-benzoyloxycyclohexanone in 350 ml. of acetic acid was added 63.4 g. of 2-tolylhydrazine hydrochloride and the solution was heated under reflux for one hour, cooled, and filtered. The resulting solids were treated with 1.5 liters of boiling methyl alcohol and the undissolved solids were collected by filtration and recrystallized from 1 liter of methyl alcohol to give 32.5 g. of crystals, m.p. 159°–163° C. The first methyl alcohol filtrate on cooling yielded 29.1 g. of crystals, m.p. 159°–169° C. The first crop was recrystallized from 300 ml. of acetic acid, the second crop was slurried in water and filtered, and the resulting solids were combined to yield 54 g. of 3-(benzoyloxy)-8-methyl-1,2,3,4-tetrahydrocarbazole, m.p. 159°–163° C. The 3-(benzoyloxy)-8-methyl-1,2,3,4-tetrahydrocarbazole (62 g.) was converted to 23.9 g. of 3-(hydroxy)-8-methyl-1,2,3,4-tetrahydrocarbazole, m.p. 201°–204° C., following a procedure similar to that described in Example 3 for the preparation of 3-(hydroxy)-6-methoxy-1,2,3,4-tetrahydrocarbazole, 21.9 g. of which was converted to 32.6 g. of 3-(p-toluenesulfonyloxy)-8-methyl-1,2,3,4-tetrahydrocarbazole, m.p. 130°–132° C., by following a procedure similar to that described in Example 18 for the preparation of 3-(p-toluenesulfonyloxy)-1,2,3,4-tetrahydrocarbazole. A mixture of 26.9 g. of 3-(p-toluenesulfonyloxy)-8-methyl-1,2,3,4-tetrahydrocarbazole and 75 ml. of pyrrolidine was heated under reflux for one and one-half hours in a nitrogen atmosphere and the solution was evaporated to dryness under reduced pressure. The residue was recrystallized from isopropyl alcohol and the resulting 8.5 g. of crystals were dissolved in ether and treated with hydrogen chloride in ethyl alcohol to give, after recrystallization from methyl alcohol, 6.8 g. of 3-(1-pyrrolidinyl)-8-methyl-1,2,3,4-tetrahydrocarbazole, m.p. > 300° C.

EXAMPLE 253

3-(Dimethylamino)-5,9-dimethyl-1,2,3,4-tetrahydrocarbazole

To a slurry of 1 g. of sodium hydride in 20 ml. of dimethylformamide was added 9.5 g. of 3-(dimethylamino)-5-methyl-1,2,3,4-tetrahydrocarbazole (Example 245A) in 100 ml. of dimethylformamide. The mixture was stirred for one hour, 5.9 g. of methyl iodide was added to the resulting clear solution in one portion, and the solution was heated for two hours on a steam bath, stirred at room temperature for one hour, diluted in 300 ml. of water and left stand for eighteen hours. The resulting solids were filtered, the filtrate was extracted with ether, the ether extract was washed with water and dried over magnesium sulfate and evaporated to dryness. The residue was combined with the solids, dissolved in ether and treated with hydrogen chloride in ethyl alcohol to give, on recrystallization from water, 3.5 g. of 3-(dimethylamino)-5,9-dimethyl-1,2,3,4-tetrahydrocarbazole hydrochloride, m.p. 318°–320° C.

EXAMPLE 254

3-(Dimethylamino)-5,7,9-trimethyl-1,2,3,4-tetrahydrocarbazole

Following a procedure similar to that described in Example 253 and using 10.3 g. of 3-(dimethylamino)-5,7-dimethyl-1,2,3,4-tetrahydrocarbazole (Example 221), 7.02 g. of sodium hydride, 6.65 g. of methyl iodide, and 70 ml. of dimethylformamide there was obtained 5.4 g. of 3-(dimethylamino)-5,7,9-trimethyl-1,2,3,4-tetrahydrocarbazole hydrochloride, m.p. 320°–322° C.

EXAMPLE 255

3-(Dimethylamino)-9-carboxymethyl-1,2,3,4-tetrahydrocarbazole

A mixture of 9.9 g. of 9-carbethoxymethyl-3-(dimethylamino)-1,2,3,4-tetrahydrocarbazole hydrochloride (Example 14) in 50 ml. of 6-N hydrochloric acid was heated on a steam bath for one and one-half hours, cooled, and the resulting solids were collected by filtration to give, after recrystallization from ethyl alcohol-water, 6.26 g. of 3-(dimethylamino)-9-carboxymethyl-1,2,3,4-tetrahydrocarbazole hydrochloride, m.p. 316°–319° C.

EXAMPLE 256

3-(Dimethylamino)-1,2,3,4-tetrahydrocarbazole-9-propionic acid

To a solution of 17.1 g. of 3-(dimethylamino)-1,2,3,4-tetrahydrocarbazole in 150 ml. of benzene was added 10.6 g. of acrylonitrile followed by 1 ml. of 35% benzyltrimethylammonium hydroxide in methyl alcohol. The solution was heated under reflux for one hour and fifteen minutes, cooled to room temperature, filtered, and evaporated to dryness. The residue was treated with hot hexane and then hot heptane (total volume 3.3 liters), both solutions being decanted from insoluble gum. The combined hexane-heptane solution was cooled and filtered to give a solid which, on recrystallization from hexane, yielded 8.6 g. of 3-(dimethylamino)-9-(2-cyanoethyl)-1,2,3,4-tetrahydrocarbazole, m.p. 106°–108° C. A solution of 13 g. of 3-(dimethylamino)-9-(2-cyanoethyl)-1,2,3,4-tetrahydrocarbazole in 125 ml. of ethyl alcohol and 150 ml. of 10% potassium hydroxide solution was heated under reflux for 3 hours, cooled, and the ethyl alcohol was removed under reduced pressure. The resulting aqueous solution was extracted with benzene, and the aqueous layer was separated and treated with acid to pH 7, cooled, and filtered to give 5.6 g. of solid material. The filtrate was acidified to pH 6 and the resulting crystals were collected by filtration. The filtrate was evaporated to dryness under reduced pressure and the solid residue was slurried in water and collected by filtration. The above three crops of solids were combined, dissolved in ethyl alcohol and treated with hydrogen chloride in ethyl alcohol to give, on filtration and recrystallization from ethyl alcohol, 11.4 g. of 3-(dimethylamino)-1,2,3,4-tetrahydrocarbazole-9-propionic acid hydrochloride, m.p. 304°–305° C.

EXAMPLE 257

Ethyl 3-(dimethylamino)-1,2,3,4-tetrahydrocarbazole-9-propionate

Following a procedure similar to that described in Example 256 and using 20 g. of 3-(dimethylamino)-1,2,3,4-tetrahydrocarbazole, 20 g. of ethyl acrylate, 1 ml. of 35% benzyltrimethylammonium hydroxide in methyl alcohol and 150 ml. of benzene and increasing the reflux time to three hours, there was obtained, on the evaporation of the reaction mixture to dryness, an oil, a solution of which in ethyl alcohol was treated with hydrogen chloride in ethyl alcohol. The resulting solids were filtered to give, after recrystallization from aqueous ethyl alcohol, 20.5 g. of ethyl 3-(dimethylamino)-1,2,3,4-tetrahydrocarbazole-9-propionate hydrochloride, m.p. 259°–261° C.

EXAMPLE 258

3-(Dimethylamino)-8-hydroxy-1,2,3,4-tetrahydrocarbazole

To a solution of 14 g. of 3-(dimethylamino)-8-benzyloxy-1,2,3,4-tetrahydrocarbazole hydrochloride (Example 231) in aqueous ethyl alcohol (1:1) was added 1 g. of 10% palladium on charcoal and the mixture was subjected to a hydrogen atmosphere at about 60 psig until hydrogen uptake ceased. The mixture was filtered and the filtrate was evaporated to dryness to give 9.7 g. of 3-(dimethylamino)-8-hydroxy-1,2,3,4-tetrahydrocarbazole hydrochloride, m.p. 315°–318° C.

EXAMPLE 259

3-(Dimethylamino)-7-hydroxy-1,2,3,4-tetrahydrocarbazole

Following a procedure similar to that described in Example 258 and using 12 g. of 3-(dimethylamino)-7-benzyloxy-1,2,3,4-tetrahydrocarbazole hydrochloride (Example 239) in 200 ml. of aqueous ethyl alcohol (1:1) and 2 g. of 10% palladium on charcoal, there was obtained 10 g. of 3-(dimethylamino)-7-hydroxy-1,2,3,4-tetrahydrocarbazole hydrochloride, m.p. 286°–288° C.

EXAMPLE 260

3-(Benzylmethylamino)-6,8-difluoro-1,2,3,4-tetrahydrocarbazole 4-(N-methylbenzamido)-cyclohexanol A stirred solution of 12.9 g. of 4-methylaminocyclohexanol in 100 ml. of water and 50 ml. of 10% sodium hydroxide solution was cooled in an ice bath and 15.5 g. of benzoyl chloride was added dropwise and stirring was continued for thirty minutes. The resulting precipitate was collected by filtration and washed with water to give 18.2 g. of 4-(N-methylbenzamido)-cyclohexanol, m.p. 159°–164° C.

4-(N-methylbenzamido)-cyclohexanone

A solution of 17 g. of 4-(N-methylbenzamido)-cyclohexanol in 500 ml. of aqueous acetone (1:1) was heated under reflux and a solution of 8-N chromium trioxide in aqueous sulfuric acid (prepared by adding 26.7 g. of chromium trioxide to 40 ml. of water followed by the addition of 23 ml. of concentrated sulfuric acid and dilution to 100 ml.) was added dropwise until no starting material remained (as determined by thin layer chromatography). The mixture was cooled, made neutral by the addition of solid sodium bicarbonate, and the acetone was evaporated under reduced pressure. The mixture was filtered and the solids were washed several times with chloroform. The chloroform washes were used to extract the aqueous filtrate, dried, and evaporated to dryness to give 7 g. of 4-(N-methylbenzamido)-cyclohexanone, m.p. 126°–128° C.

3-(N-methylbenzamido)-6,8-difluoro-1,2,3,4-tetrahydrocarbazole

A solution of 16.2 g. of 4-(N-methylbenzamido)-cyclohexanone, 9.6 g. of 2,4-difluorophenylhydrazine, and 13.4 g. of methanesulfonic acid in 200 ml. of absolute ethyl alcohol was heated under reflux for 2 hours, cooled, and filtered. The resulting solid was taken up in chloroform, filtered from undissolved solids and evaporated to dryness to give, after recrystallization from isopropyl alcohol, 9 g. of 3-(N-methylbenzamido)-6,8-difluoro-1,2,3,4-tetrahydrocarbazole, m.p. 212°–214° C.

To a slurry of 1.2 g. of lithium aluminum hydride in 60 ml. of dry tetrahydrofuran was added dropwise a solution of 4.6 g. of 3-(N-methylbenzamido)-6,8-difluoro-1,2,3,4-tetrahydrocarbazole in 60 ml. of dry tetrahydrofuran, and when addition was complete, the mixture was refluxed for forty minutes. Ethyl acetate (15 ml.) was added, followed by 10 ml. of wet ether and, finally 5 ml. of water. The mixture was filtered and the filtrate was evaporated to dryness to give, after recrystallizations from cyclohexane and then isopropyl alcohol, 2.9 g. of 3-(benzylmethylamino)-6,8-difluoro-1,2,3,4-tetrahydrocarbazole, m.p. 137°–139° C. A solution of 0.85 g. of this free base was treated in acetonitrile with 0.11 ml. of methyl iodide, and the solution was warmed on a steam bath for fifteen minutes, cooled, and the resulting crystals were collected by filtration to give 0.65 g. of 3-(benzylmethylamino)-6,8-difluoro-1,2,3,4-tetrahydrocarbazole methiodide, m.p. 235°–236° C.

EXAMPLE 261

3-[(4-Fluorobenzyl)methylamino]-8-fluoro-1,2,3,4-tetrahydrocarbazole

Following procedures similar to those described in Example 260 there was obtained from 64.6 g. of 4-methylaminocyclohexanol, on reaction with 87.2 g. of 4-fluorobenzoyl chloride, 100.6 g. of 4-(N-methyl-4-fluorobenzamido)-cyclohexanol, m.p. 120°–130° C., 25.1 g. of which were oxidized to give 22.3 g. of 4-(N-methyl-4-fluorobenzamido)-cyclohexanone, m.p. 132°–136° C.

3-(N-methyl-4-fluorobenzamido)-8-fluoro-1,2,3,4-tetrahydrocarbazole

A solution of 21.8 g. of 4-(N-methyl-4-fluorobenzamido)-cyclohexanone and 10.1 g. of 2-fluorophenylhydrazine in 200 ml. of absolute ethyl alcohol and 80 ml. of 5-N hydrogen chloride in absolute ethyl alcohol was heated under reflux for three and one-half hours, cooled, and filtered. The solids were slurried in water, filtered, and recrystallized from dimethylformamide to give 9.1 g. of 3-(N-methyl-4-fluorobenzamido)-8-fluoro-1,2,3,4-tetrahydrocarbazole, m.p. 276°–278° C.

By following a procedure similar to that described in Example 260 and using 6 g. of 3-(N-methyl-4-fluorobenzamido)-8-fluoro-1,2,3,4-tetrahydrocarbazole in 500 ml. of dry tetrahydrofuran and 3 g. of lithium aluminum hydride in 60 ml. of dry tetrahydrofuran, there was obtained crude base as a yellow oil, a solution of which in ethyl alcohol was treated with 10 ml. of 5-N hydrogen chloride in ethyl alcohol to give, on filtration of the resulting solid, 5.1 g. of 3-[(4-fluorobenzyl)methylamino]-8-fluoro-1,2,3,4-tetrahydrocarbazole hydrochloride, m.p. 262°–264° C.

EXAMPLE 262

3-(Ethylamino)-8-fluoro-1,2,3,4-tetrahydrocarbazole
3-Acetamido-8-fluoro-1,2,3,4-tetrahydrocarbazole A solution of 7.8 g. of 4-acetamidocyclohexanone and 8.1 g. of 2-fluorophenylhydrazine hydrochloride in 75 ml. of absolute ethyl alcohol and 25 ml. of 5-N hydrogen chloride in absolute ethyl alcohol was heated under reflux for two hours, cooled, filtered, and the filtrate was evaporated to dryness. The residue was dissolved in chloroform and adsorbed on a column of aluminum oxide. Dilution with ether yielded first a small amount of side-product followed by the desired product which was recrystallized by dissolving in methyl alcohol, adding toluene and evaporation of the methyl alcohol, to give 10.5 g. of 3-acetamido-8-fluoro-1,2,3,4-tetrahydrocarbazole, m.p. 202°–204° C.

Following a reductive procedure similar to that described in Example 260 but substituting for 3-(N-methylbenzamido)-6,8-difluoro-1,2,3,4-tetrahydrocarbazole an equivalent amount of 3-acetamido-8-fluoro-1,2,3,4-tetrahydrocarbazole there can be obtained 3-(ethylamino)-8-fluoro-1,2,3,4-tetrahydrocarbazole.

EXAMPLE 263

3-(Isobutylamino)-6,8-difluoro-1,2,3,4-tetrahydrocarbazole 3-(Acetamido)-6,8-difluoro-1,2,3,4-tetrahydrocarbazole A solution of 15.5 g. of 4-acetamidocyclohexanone, 18 g. of 2,4-difluorophenylhydrazine hydrochloride and 10 g. of methanesulfonic acid in 200 ml. of absolute ethyl alcohol was heated under reflux for two hours, cooled, filtered, and the filtrate was evaporated to dryness under reduced pressure. The residual oil was triturated with water and the resulting solid was collected by filtration, triturated with ether, and recrystallized by dissolving in methanol, adding toluene, and evaporating the methanol to give 8.5 g. of 3-(acetamido)-6,8-difluoro-1,2,3,4-tetrahydrocarbazole, m.p. 179°–183° C.

3-Amino-6,8-difluoro-1,2,3,4-tetrahydrocarbazole

A suspension of 6 g. of 3-(acetamido)-6,8-difluoro-1,2,3,4-tetrahydrocarbazole in 200 ml. of 20% aqueous sulfuric acid was heated under reflux for forty hours and the resulting solution was cooled, filtered, made alkaline with dilute potassium hydroxide, and extracted with ether. The ether extract was washed with water, dried and ethereal hydrogen chloride was added to give on filtration 4.9 g. of 3-amino-6,8-difluoro-1,2,3,4-tetrahydrocarbazole hydrochloride, m.p. > 300° C. This compound was found to have psychotrophic activity when tested in mice and is indicated for use as an antianxiety and antipsychotic agent.

Following the acylation procedure similar to that described in Example 260 for the preparation of N-methyl benzamidocyclohexanol, there is obtained from 3-amino-6,8-difluoro-1,2,3,4-tetrahydrocarbazole and isobutyryl chloride, 3-isobutyramido-6,8-difluoro-1,2,3,4-tetrahydrocarbazole, which by following the lithium aluminum hydride reductive procedure described in Example 260, can be converted to 3-(isobutylamino)-6,8-difluoro-1,2,3,4-tetrahydrocarbazole.

By following the lithium aluminum hydride reductive procedure described in Example 260 but using 3-(acetamido)-6,8-difluoro-1,2,3,4-tetrahydrocarbazole there is obtained 264. 3-(Ethylamino)-6,8-difluoro-1,2,3,4-tetrahydrocarbazole.

EXAMPLE 265

3-(Dimethylamino)-6-fluoro-9-(4-fluorophenyl)-1,2,3,4-tetrahydrocarbazole

A solution 7.8 g. of 4-dimethylaminocyclohexanone and 11 g. of 1,1-bis(4-fluorophenyl)hydrazine in 350 ml. of absolute ethyl alcohol and 90 ml. of 5-N hydrogen chloride in absolute ethyl alcohol was heated under reflux for five hours, cooled, and filtered. The solids were suspended in ether and treated with dilute sodium hydroxide solution and the ether extract was separated, dried and evaporated to dryness. The resulting oil was dissolved in ethyl alcohol, treated with hydrogen chloride in ethyl alcohol and the solution was concentrated and cooled. The resulting solids were collected by filtration to give, after recrystallization from ethyl alcohol, 5.6 g. of 3-(dimethylamino)-6-fluoro-9-(4-fluorophenyl)-1,2,3,4-tetrahydrocarbazole hydrochloride, m.p. 283°–285° C.

EXAMPLES 266–271

By following an acylation procedure similar to that described in Example 260 for the preparation of 4-(N-methyl benzamido)-cyclohexanol but substituting for 4-methylaminocyclohexanol an equivalent amount of
3-(methylamino)-5,6,7,8-tetrafluoro-1,2,3,4-tetrahydrocarbazole,
3-(dimethylamino)-6-amino-1,2,3,4-tetrahydrocarbazole (Example 38), or
3-[2-(diethylamino)ethylamino]-1,2,3,4-tetrahydrocarbazole (Example 31)
and, in each case, for benzoyl chloride an equivalent amount of isobutyryl chloride or hexanoyl chloride there are obtained, respectively,
3-(N-methylisobutyramido)-5,6,7,8-tetrafluoro-1,2,3,4-tetrahydrocarbazole,
3-(N-methylhexanamido)-5,6,7,8-tetrafluoro-1,2,3,4-tetrahydrocarbazole,
3-(dimethylamino)-6-isobutyramido-1,2,3,4-tetrahydrocarbazole,
3-(dimethylamino)-6-hexanamido-1,2,3,4-tetrahydrocarbazole,
3-{N-[2-(diethylamino)ethyl]isobutyramido}-1,2,3,4-tetrahydrocarbazole, and
3-{N-[2-(diethylamino)ethyl]hexanamido}-1,2,3,4-tetrahydrocarbazole.

By following a lithium aluminum hydride reduction procedure similar to that described in Example 260 there are obtained from the above amides, respectively, 266. 3-(Methylisobutylamino)-5,6,7,8-tetrafluoro-1,2,3,4-tetrahydrocarbazole,
267. 3-(Methylhexylamino)-5,6,7,8-tetrafluoro-1,2,3,4-tetrahydrocarbazole,
268. 3-(Dimethylamino)-6-isobutylamino-1,2,3,4-tetrahydrocarbazole,
269. 3-(Dimethylamino)-6-hexylamino-1,2,3,4-tetrahydrocarbazole,
270. 3-{Isobutyl-[2-(diethylamino)ethyl]amino}-1,2,3,4-tetrahydrocarbazole, and
271. 3-{Hexyl-[2-(diethylamino)ethyl]amino}-1,2,3,4-tetrahydrocarbazole.

The 3-(methylamino)-5,6,7,8-tetrafluoro-1,2,3,4-tetrahydrocarbazole above can be prepared by following a procedure similar to that described in Example 205 but substituting for 4-phenoxyphenylhydrazine hydrochloride and 4-dimethylaminocyclohexanone equivalent amounts of 2,3,4,5-tetrafluorophenylhydrazine hydrochloride and 4-methylaminocyclohexanone respectively.

EXAMPLES 272–273

By heating a solution of 3-(dimethylamino)-6-amino-1,2,3,4-tetrahydrocarbazole or 3-[2-(diethylamino)ethylamino]-1,2,3,4-tetrahydrocarbazole in formamide for several hours there can be obtained, after isolation by standard procedures, respectively, 3-(dimethylamino)-6-formamido-1,2,3,4-tetrahydrocarbazole and 3-{N-[2-(diethylamino)ethyl]formamido}-1,2,3,4-tetrahydrocarbazole, which can be reduced with lithium aluminum hydride, following a procedure similar to that described in Example 260, to give, respectively, 272. 3-(Dimethylamino)-6-methylamino-1,2,3,4-tetrahydrocarbazole and
273. 3-{Methyl-[2-(diethylamino)ethyl]amino}-1,2,3,4-tetrahydrocarbazole.

EXAMPLES 274–281

By following an acylation procedure similar to that described in Example 260 for the preparation of 4-N-(methylbenzamido)-cyclohexanol but substituting for 4-methylaminocyclohexanol an equivalent amount of 3-(methylamino)-6,8-difluoro-1,2,3,4-tetrahydrocarbazole (Example 249) and for benzoyl chloride and equivalent amount of the benzoyl chlorides substituted as follows: 3,4,5-trimethoxy, 4-methyl,2-chloro-4-nitro, 3-trifluoromethyl, 4-hexyl, 4-isopropyl, 4-fluoro and 4-pentyloxy, there are obtained, respectively, 3-(N-methyl-3,4,5-trimethoxybenzamido)-6,8-difluoro-1,2,3,4-tetrahydrocarbazole,
3-(N-methyl-4-methylbenzamido)-6,8-difluoro-1,2,3,4-tetrahydrocarbazole,
3-(N-methyl-2-chloro-4-nitrobenzamido)-6,8-difluoro-1,2,3,4-tetrahydrocarbazole,
3-[N-methyl-3-(trifluoromethyl)benzamido]-6,8-difluoro-1,2,3,4-tetrahydrocarbazole,
3-(N-methyl-4-hexylbenzamido)-6,8-difluoro-1,2,3,4-tetrahydrocarbazole,
3-(N-methyl-4-isopropylbenzamido)-6,8-difluoro-1,2,3,4-tetrahydrocarbazole,
3-(N-methyl-4-fluorobenzamido)-6,8-difluoro-1,2,3,4-tetrahydrocarbazole, and
3-(N-methyl-4-pentyloxybenzamido)-6,8-difluoro-1,2,3,4-tetrahydrocarbazole.

By following a lithium aluminum hydride reduction procedure similar to that described in Example 260 there are obtained from the above benzamides, respectively, 274. 3-[(3,4,5-Trimethoxybenzyl)methylamino]-6,8-difluoro-1,2,3,4-tetrahydrocarbazole,
275. 3-[(4-Methylbenzyl)methylamino]-6,8-difluoro-1,2,3,4-tetrahydrocarbazole,
276. 3-[(2-Chloro-4-nitrobenzyl)methylamino]-6,8-difluoro-1,2,3,4-tetrahydrocarbazole,
277. 3-{[3-(Trifluoromethyl)benzyl]methylamino}-6,8-difluoro-1,2,3,4-tetrahydrocarbazole,
278. 3-[(4-Hexylbenzyl)methylamino]-6,8-difluoro-1,2,3,4-tetrahydrocarbazole,
279. 3-[(4-Isopropylbenzyl)methylamino]-6,8-difluoro-1,2,3,4-tetrahydrocarbazole,
280. 3-[(4-Fluorobenzyl)methylamino]-6,8-difluoro-1,2,3,4-tetrahydrocarbazole, and
281. 3-[(4-Pentyloxybenzyl)methylamino]-6,8-difluoro-1,2,3,4-tetrahydrocarbazole.

The following compounds (Example numbers given in parenthesis) were found to have antihistaminic activity when tested according to test procedure 7, described hereinbefore, in the dose range of 1 to 30 mg./kg. (as base):

3-(dimethylamino)-8-fluoro-1,2,3,4-tetrahydrocarbazole (37),
3-(dimethylamino)-6,8-difluoro-1,2,3,4-tetrahydrocarbazole (204),
3-(dimethylamino)-5,8-difluoro-1,2,3,4-tetrahydrocarbazole (222), and
3-(dimethylamino)-8-fluoro-5-methyl-1,2,3,4-tetrahydrocarbazole (224).

By following the conventional procedures described hereinbefore for the preparation of acid-addition salts by reaction of the corresponding free bases with the appropriate acid there were obtained from the title compounds of Examples 37, 239 and 240 respectively the following:

37A. 3-(dimethylamino)-8-fluoro-1,2,3,4-tetrahydrocarbazole methane sulfonate; m.p. 174°–176° C.(acetone);
239A. 3-(dimethylamino)-7-(benzyloxy)-1,2,3,4-tetrahydrocarbazole methane sulfonate; m.p. 190°–193° C.(acetone-ether); and
240A. 3-(dimethylamino)-7-methoxy-1,2,3,4-tetrahydrocarbazole hydrochloride; m.p. 250°–255° C.(ethyl alcohol).

EXAMPLE 209A

A mixture of racemic 3-(dimethylamino)-6,8-dichloro-1,2,3,4-tetrahydrocarbazole (Example 209)(52g)and (-)-2,3: 4,6-di-O-isopropylidene-2-keto-L-gulonic acid hydrate (l -diacetone-2-keto-L-gulonic acid hydrate)(53.8g) in 550 ml. of water was stirred and warmed to 45° C. The resulting solution was filtered and allowed to stand at room temperature for 65 hours. The resulting crystals were filtered (filtrate A), washed with water, dried (yield 38g.) and recrystallized from ethyl alcohol (67ml)-water(136ml)and dried to give 35.5g. of d-3-(dimethylamino)-6,8-dichloro-1,2,3,4-tetrahydrocarbazole l-diacetone-2-keto-L-gulonate; m.p. 140°–150° C., which was converted to the free base (26g.) on treatment with aqueous sodium hydroxide and extraction with chloroform. The free base was recrystallized from benzene to give 16g. of di-3-(dimethylamino)-6,8-dichloro-1,2,3,4-tetrahydrocarbazole, m.p. 164°–166° C., $[\alpha]_D^{25}=+89.6°$ (1% in CHCl$_3$), of which 14.7g. was treated with 4.3ml. of concentrated hydrochloric acid in 300ml. isopropyl alcohol to give the corresponding hydrochloride salt, m.p. 297°–299° C.(dec.), $[\alpha]_D^{25}=+71.7°$ (1% in H$_2$O). Filtrate A (Above) was treated with sodium hydroxide until alkaline and extracted with chloroform and the extract was evaporated to dryness. The resulting residue was slurried in 200ml. of boiling isopropyl acetate and the mixture was cooled and filtered to give 15.5g. of the racemic base starting material. The isopropyl acetate filtrate was evaporated to dryness and the residue was triturated in boiling hexane and filtered to give 15.0g. of crystals (m.p. 164°–167° C.) which were recrystallized from 68ml. of benzene to tive 13.6g. of l-3-(dimethylamino)-6,8-dichloro-1,2,3,4-tetrahydrocarbazole, m.p. 163°–165° C., $[\alpha]_D^{25}=-89.3°$ (1% in CHCl$_3$), of which 12.5g. were treated with 3.6ml. of concentrated hydrochloric acid in isopropyl alcohol by heating at reflux for ten minutes to give, on cooling and filtration, 13.9 g. of the corresponding hydrochloride salt, m.p. 296°–298° C., $[\alpha]_D^{25}=-71.7°$ (1% in H$_2$O).

EXAMPLE 239AA

A solution of 3-(dimethylamino)-7-(benzyloxy)-1,2,3,4-tetrahydrocarbazole (Example 239)(201g.) and 228g. of dibenzoyl l-tartaric acid hydrate in 8.58 liters of methyl alcohol were stirred at room temperature for 45 hours. The resulting crystals were filtered (filtrate A), washed with 150ml. of methyl alcohol three times, then ether and dried to give, after recrystallization from methyl alcohol (5 l) 98g. of l-3-(dimethylamino)-7-(benzyloxy)-1,2,3,4-tetrahydrocarbazole dibenzoyl l-bitartrate, m.p. 163° C.(dec.), $[\alpha]_D^{25}=-102.3°$ (1% in acetic acid), which was converted to the free base by treatment with ammonium hydroxide to give, on extraction with chloroform and recrystallization from isopropyl acetate, 43.5g. of l-3-(dimethylamino)-7-(benzyloxy)-1,2,3,4-tetrahydrocarbazole, m.p. 128°–130° C. Filtrate A (above) was concentrated to 400ml. and made alkaline with ammonium hydroxide and extracted with chloroform. The chloroform extract was washed once with water, dried and evaporated to dryness and the resulting 170g. of residue was crystallized from 360ml. of isopropyl acetate to give 130g. of the racemic starting material and the filtrate, on standing, yielded 20g. of d-3-(dimethylamino)-7-(benzyloxy) 1,2,3,4-tetrahydrocarbazole, m.p. 128°–129° C.,$[\alpha]_D^{25}=+74.3°$ (1% in CHCl$_3$).

EXAMPLE 259A

To a solution of 20.5g. of d-3-(dimethylamino)-7-(benzyloxy)-1,2,3,4-tetrahydrocarbazole (Example 239AA)in 300ml. of aqueous ethyl alcohol (1:1) containing 5.5ml. of concentrated hydrochloric acid was added 2.5g. of 10% palladium on charcoal and the mixture was subjected to a hydrogen atmosphere at about 60psig until hydrogen utake ceased. The mixture was filtered and the filtrate was evaporated to dryness and the residue was crystallized from ethyl alcohol to give 14g. of d-3-(dimethylamino)-7-hydroxy-1,2,3,4-tetrahydrocarbazole hydrochloride, m.p. 300°–303° C. (dec.), $[\alpha]_D^{25}=+71.1°$ (1% in H$_2$O).

In a like manner 42g. of l-3-(dimethylamino)-7-(benzyloxy)-1,2,3,4-tetrahydrocarbazole (Example 239AA) was converted to 31g. of l-3-(dimethylamino)-7-hydroxy-1,2,3,4-tetrahydrocarbazole hydrochloride, m.p. 303°–305° C.(dec.), $[\alpha]_D^{25}=-70.4°$ (1% in H$_2$O).

EXAMPLE 239AB

3-(Dimethylamino)-5-(benzyloxy)-1,2,3,4-tetrahydrocarbazole

A solution of 3-benzyloxyphenylhydrazine hydrochloride (140g.) and 4-dimethylaminocyclohexanone hydrochloride (100g.) in 3 liters of ethyl alochol was refluxed for six hours and evaporated to dryness. The solid was suspended in 1 liter of water and filtered to give 119g. of 3-(dimethylamino)-7-(benzyloxy)-1,2,3,4-tetrahydrocarbazole hydrochloride (Example 239). The water filtrate deposited a solid which was recrystallized from ethyl alcohol to give 38g. of 3-(dimethylamino)-5-(benzyloxy)-1,2,3,4-tetrahydrocarbazole hydrochloride, m.p. 207°–209° C.

EXAMPLE 282

A.
3-(Dimethylamino)-5-(benzyloxy)-9-methyl-1,2,3,4-tetrahydrocarbazole and (B)
3-(Dimethylamino)-7-(benzyloxy)-9-methyl-1,2,3,4-tetrahydrocarbazole.

A solution of 1-methyl-1-(benzyloxyphenyl)-hydrazine hydrochloride (31.0g.), prepared in a conventional manner from N-methyl-3-benzyloxyaniline by nitrosation and reduction with lithium aluminum hydride, and 4-dimethylaminocyclohexanone hydrochloride (21.5g.) in 200ml. of absolute ethyl alcohol was heated at reflux for 45 minutes. The mixture was chilled and filtered and the collected solid was washed with 100 ml. of ethyl alcohol-water (1:1) and triturated with 100ml. of water and filtered to give 33.5g. of solid material. The aqueous ethyl alcohol reaction mother liquors were evaporated to dryness to give 13g. of an oil. The solid material (33g.) was slurried in 200ml. of hot ethyl alcohol and the slurry was cooled and filtered. Slurrying was repeated in 500ml. of ethyl alcohol and the resulting solid was dried to give 25g. of 3-(dimethylamino)-7(benzyloxy)-9-methyl-1,2,3,4-tetrahydrocarbazole hydrochloride, m.p. >280° C. The filtrate from the 500ml. ethyl alcohol slurry, on chilling, deposited 3.1g. of 3-(dimethylamino)-5-(benzyloxy)-9-methyl-1,2,3,4-tetrahydrocarbazole hydrochloride, m.p. 198°–201° C.

By reaction of the appropriate phenylhydrazine with 4-acetamido-, appropriate 4-substituted-amino-, or 4-benzoyloxycyclohexanone, following procedures described hereinbefore, there were obtained the following compounds:

283. 3-Acetamido-6,7-dimethoxy-1,2,3,4-tetrahydrocarbazole, m.p. 180°–183° C.,
284. 3-Acetamido-5,7-dichloro-1,2,3,4-tetrahydrocarbazole, m.p. 223°–224° C.,
285. 3-Acetamido-6,8-dichloro-1,2,3,4-tetrahydrocarbazole, m.p. 247°–250° C.,
286. 3-(Dimethylamino)-5-methoxy-8-chloro-1,2,3,4-tetrahydrocarbazole, m.p. 147°–149° C.,
287. 3-(Dimethylamino)-6,8-dibromo-1,2,3,4-tetrahydrocarbazole hydrochloride, m.p. 275°–277° C.,
288. 3-(Ethylamino)-6,8-dichloro-1,2,3,4-tetrahydrocarbazole, m.p. 152°–154° C.,
289. 3-(Methylamino)-6,8-dichloro-1,2,3,4-tetrahydrocarbazole, m.p. 151°–153° C.,
290. 3-(Dimethylamino)-5,7-dichloro-1,2,3,4-tetrahydrocarbazole, m.p. 223°–225° C., 291. 3-(Dimethylamino)-7-(benzyloxy)-6-methyl-1,2,3,4-tetrahydrocarbazole hydrochloride, m.p. 240°-243° C., and 292. 3-(Benzoyloxy)-6,8-dichloro-1,2,3,4-tetrahydrocarbazole, m.p. 155°-160° C.

By subjecting the compounds of Examples 283, 284 and 285 to a lithium aluminum hydride reductive procedure similar to that described in Example 260, there are obtained respectively:

283A. 3-(ethylamino-6,7-dimethoxy-1,2,3,4-tetrahydrocarbazole, 284A. 3-(ethylamino)-5,7-dichloro-1,2,3,4-tetrahydrocarbazole, and 3-(ethylamino)-6,8-dichloro-1,2,3,4-tetrahydrocarbazole (Example 288).

Following procedures similar to those described in Example 252 there are obtained starting from 3-(benzoyloxy)-6,8-dichloro-1,2,3,4-tetrahydrocarbazole (Example 292) the following:

292A. 3-hydroxy-6,8-dichloro-1,2,3,4-tetrahydrocarbazole, m.p. 153°-156° C., 292B. 3-(p-toluenesulfonyloxy)-6,8-dichloro-1,2,3,4-tetrahydrocarbazole, and 292C. 3-(1-pyrrolidinyl)-6,8-dichloro-1,2,3,4-tetrahydrocarbazole.

Following a hydrogenation procedure similar to that described in Example 258 there was obtained from the hydrochloride salts of the compounds of Examples 293AB, 282A, 282B and 291 respectively:

293. 3-(Dimethylamino)-5-hydroxy-1,2,3,4-tetrahydrocarbazole hydrochloride, m.p. >300° C., 294. 3-(Dimethylamino)-5-hydroxy-9-methyl-1,2,3,4-tetrahydrocarbazole hydrochloride, m.p. 255°-258° C.(dec.), 295. 3-(Dimethylamino)-7-hydroxy-9-methyl-1,2,3,4-tetrahydrocarbazole hydrochloride, m.p. 295° C.(dec.), methane sulfonate salt, m.p. 227°-230° C., and 296. 3-(Dimethylamino)-7-hydroxy-6-methyl-1,2,3,4-tetrahydrocarbazole hydrochloride, m.p. 299°-301° C., methane sulfonate salt, m.p. 259°-261° C.

EXAMPLE 297

3-(Dimethylamino)-5-methoxy-1,2,3,4-tetrahydrocarbazole

Following a procedure similar to that described in Example 234 there was obtained from 12.1 g. of 3-(dimethylamino)-5-methoxy-8-chloro-1,2,3,4-tetrahydrocarbazole (Example 286), 8.7 g. of the title compound, m.p. 185°-189° C.

I claim:

1. A 3-(OZ)-9-R$_4$-1,2,3,4-tetrahydrocarbazole having the formula

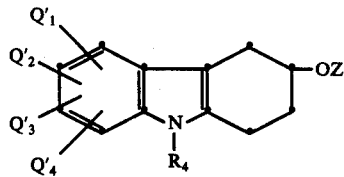

where Z is hydrogen or

R$_4$ is hydrogen, lower-alkyl, Ar-lower-alkyl, carboxy-lower-alkyl or lower-alkoxy-carbonyl-lower-alkyl, or R$_4$ is Y-NR'R", where R' and R" are lower-alkyl and Y is lower-alkylene;

Q'$_1$ is selected from hydrogen, lower-alkoxy and halo;

Q'$_2$ is selected from hydrogen, non-tertiary-lower-alkyl, lower-alkoxy and halo;

Q'$_3$ and Q'$_4$ each are hydrogen; and

Ar is phenyl or phenyl mono-substituted by lower-alkyl or halo;

where lower-alkyl and lower-alkoxy, every occurrence, have from one to six carbon atoms and lower-alkylene has from two to four carbon atoms;

provided that when Z is hydrogen then R$_4$ cannot be lower-alkoxycarbonyl-lower-alkyl, and when R$_4$ is hydrogen or lower-alkyl at least one of Q'$_1$ and Q'$_2$ is other than hydrogen or lower-alkyl.

2. A compound according to claim 1 where Z is hydrogen.

3. A compound according to claim 1 where Z is

4. A compound according to claim 2 selected from:
a. 3-hydroxy-9-(p-chlorobenzyl)-1,2,3,4-tetrahydrocarbazole,
b. 3-hydroxy-6,7-dimethoxy-1,2,3,4-tetrahydrocarbazole,
c. 3-hydroxy-9-[3-(dimethylamino)propyl]-1,2,3,4-tetrahydrocarbazole,
d. 3-hydroxy-6-ethoxy-1,2,3,4-tetrahydrocarbazole,
e. 3-hydroxy-6-methoxy-1,2,3,4-tetrahydrocarbazole
and f. 3-hydroxy-6,8-dichloro-1,2,3,4-tetrahydrocarbazole.

5. A compound according to claim 3 selected from:
a. 3-benzoyloxy-9-(p-chlorobenzyl)-1,2,3,4-tetrahydrocarbazole,
b. 3-benzoyloxy-9-[2-(dimethylamino)ethyl]-1,2,3,4-tetrahydrocarbazole,
c. 3-benzoyloxy-9-[3-(dimethylamino)propyl]-1,2,3,4-tetrahydrocarbazole,
d. 3-benzoyloxy-6,7-dimethoxy-1,2,3,4-tetrahydrocarbazole,
e. 3-benzoyloxy-6-ethoxy-1,2,3,4-tetrahydrocarbazole
and f. 3-benzoyloxy-6,7-dimethyloxy-9-carbethoxymethyl-1,2,3,4-tetrahydrocarbazole.

6. A 3-(OZ$_1$)-9-R'$_4$-1,2,3,4-tetrahydrocarbazole having the formula

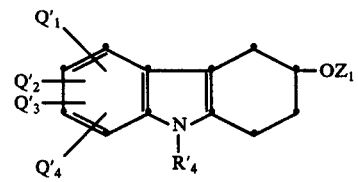

where Z$_1$ is Ar-SO$_2$-;

R'$_4$ is hydrogen, lower-alkyl, Ar-lower-alkyl or carboxy-lower-alkyl, or R'$_4$ is Y-NR'R", where R' and R" are lower-alkyl and Y is lower-alkylene;

Q'$_1$ is selected from hydrogen, lower alkoxy and halo;

Q'$_2$ is selected from hydrogen, non-tertiary lower-alkyl, lower-alkoxy and halo;

$Q'_3$ and $Q'_4$ each are hydrogen; and Ar is phenyl or phenyl mono-substituted by lower-alkyl or halo; where lower-alkyl and lower-alkoxy, every occurrence, have from one to six carbon atoms and lower-alkylene has from two to four carbon atoms.

7. A compound according to claim 6 where $R'_4$ is hydrogen.

8. 3-(p-Toluenesulfonyloxy)-1,2,3,4-tetrahydrocarbazole according to claim 7.

* * * * *

UNITED STATES PATENT AND TRADEMARK OFFICE
CERTIFICATE OF CORRECTION

PATENT NO. : 4,062,864

DATED : December 13, 1977

INVENTOR(S) : Aram Mooradian

It is certified that error appears in the above-identified patent and that said Letters Patent are hereby corrected as shown below:

Column 1, line 12, "739,545" should read -- 793,545 --.

Column 1, line 36, "AR" should read -- Ar --.

Column 1, line 63, "AR" should read -- Ar --.

Column 5, line 50, "or" should read -- to --.

Column 8, line 61, "along" should read -- alone --.

Column 11, line 15, "CL" should read -- Cl --.

Column 17, line 9, "phychomotor" should read -- psychomotor --.

Column 17, line 36, "Pentylanetetrazol" should read -- Pentylenetetrazol --.

Column 62, Claim 5, line 49, "dimethyloxy" should read -- dimethoxy --.

Signed and Sealed this

Eleventh Day of December 1979

[SEAL]

Attest:

SIDNEY A. DIAMOND

Attesting Officer

Commissioner of Patents and Trademarks